US012774303B2

(12) United States Patent
Myung et al.

(10) Patent No.: US 12,774,303 B2
(45) Date of Patent: Oct. 27, 2026

(54) COMPOSITIONS AND METHODS FOR IN SITU-FORMING GELS FOR WOUND HEALING AND TISSUE REGENERATION

(71) Applicants: The Board of Trustees of the Leland Stanford Junior University, Stanford, CA (US); The United States Government as Represented by The Department of Veterans Affairs, NW Washington, DC (US)

(72) Inventors: David Myung, Saratoga, CA (US); Sei Kwang Hahn, Redwood City, CA (US); Amy C. Madl, Los Altos, CA (US)

(73) Assignees: The Board of Trustees of the Leland Stanford Junior University, Stanford, CA (US); The United States Government as Represented by The Department of Veterans Affairs, NW Washington, DC (US)

( * ) Notice: Subject to any disclaimer, the term of this patent is extended or adjusted under 35 U.S.C. 154(b) by 961 days.

(21) Appl. No.: 17/760,083

(22) PCT Filed: Feb. 24, 2021

(86) PCT No.: PCT/US2021/019450
§ 371 (c)(1),
(2) Date: Aug. 3, 2022

(87) PCT Pub. No.: WO2021/173698
PCT Pub. Date: Sep. 2, 2021

(65) Prior Publication Data

US 2023/0040418 A1 Feb. 9, 2023

Related U.S. Application Data

(60) Provisional application No. 63/005,013, filed on Apr. 3, 2020, provisional application No. 62/980,851, filed on Feb. 24, 2020.

(51) Int. Cl.

| | |
|---|---|
| ***C07K 5/107*** | (2006.01) |
| ***A61F 2/14*** | (2006.01) |
| ***A61K 31/25*** | (2006.01) |
| ***A61K 31/728*** | (2006.01) |
| ***A61K 35/30*** | (2015.01) |

(52) U.S. Cl.
CPC ............ *C07K 5/1016* (2013.01); *A61F 2/145* (2013.01); *A61K 31/25* (2013.01); *A61K 31/728* (2013.01); *A61K 35/30* (2013.01)

(58) Field of Classification Search
CPC ....... C07K 5/1016; A61F 2/145; A61K 31/25; A61K 31/728; A61K 35/30
See application file for complete search history.

(56) References Cited

U.S. PATENT DOCUMENTS

| | | | | |
|---|---|---|---|---|
| 2015/0111834 | A1 | 4/2015 | Ko et al. | |
| 2016/0279868 | A1 | 9/2016 | Highley et al. | |
| 2017/0185981 | A1* | 6/2017 | Emmerson ........... | G10H 1/0058 |
| 2017/0319506 | A1 | 11/2017 | Appel | |
| 2018/0280586 | A1 | 10/2018 | Stapleton et al. | |

FOREIGN PATENT DOCUMENTS

WO WO2020006255 1/2020

OTHER PUBLICATIONS

Liu et al. (j. Polymer Sci. Part A: Polymer Chemistry 2017, 55, 3105-3109.*
Kharkar et al. (ACS Biomaterials Sci. and Eng. 2(2) 2016).*
Madl et al. (ACS Macro Lett (2020) 9(40) 619-626).*
Madl. (2020) "Injectable Cucurbit[8]urii-Based Supramolecular Gelatin Hydrogels for Cell Encapsulation" 1-15. American Chemical Society Macro Letter. Online, vol. 9, No. 4. pp. 619--626.

* cited by examiner

*Primary Examiner* — Shirley V Gembeh
(74) *Attorney, Agent, or Firm* — Pamela J. Sherwood; Bozicevic, Field & Francis LLP

(57) ABSTRACT

Compositions and methods are provided for lamellar and defect reconstruction of corneal stromal tissue using supramolecular complexes that form a defined gel structure in situ. Such gels can serve as cellular or acellular matrices with or without certain encapsulated therapeutic factors to facilitate tissue regeneration such as multilayered re-epithelialization of wounded corneal stromal tissue.

15 Claims, 44 Drawing Sheets

Day 4

CEC

C-MSC

Day 10

CEC

C-MSC

Time (days)

Acute Viability

Live/Dead
88.7 ± 4.3% Viable

Day 2 Viability

Live/Dead
93.1 ± 3.8% Viable

Day 7 Viability

Live/Dead
95.9 ± 1.4% Viable

COMPOSITIONS AND METHODS FOR IN SITU-FORMING GELS FOR WOUND HEALING AND TISSUE REGENERATION

CROSS REFERENCE

This application is a U.S. National Stage Application of PCT Application No. PCT/US2021/019450, filed Feb. 24, 2021, which application claims priority to the filing date of U.S. Provisional Application No. 62/980,851, filed Feb. 24, 2020, and U.S. Provisional Application No. 63/005,013, filed Apr. 3, 2020, the disclosure of which application is herein incorporated by reference.

GOVERNMENT SUPPORT

This invention was made with Government support under contract EY028176 and EY026877 awarded by the National Institutes of Health. The Government has certain rights in the invention.

BACKGROUND

Corneal transplantation has evolved substantially in the past two decades, and, depending on the indication, can now be done in a number of different ways. The advent of lamellar and endothelial keratoplasty, where only certain layers of the cornea are replaced, has narrowed the number of cases where a full-thickness penetrating keratoplasty is required. Although these procedures are done through variable thickness cadaveric allograft corneas, the availability of donor tissue remains limited in most parts of the world.

An alternative approach that has garnered interest is the creation of multi-layered graft materials. Decellularized allograft and xenografts have been tested with some success. For instance, a bioengineered cornea comprised of recombinant human collagen type III crosslinked by carbodiimide chemistry for deep anterior lamellar keratoplasty has resulted in long-term remodeling of the cornea and a resulting structure similar to normal corneal tissue.

To date, these approaches require the formation and molding of the replacement button ex vivo, and the placement within a deep anterior lamellar cavity created within the cornea. Yet there remain clinical situations such as a deep ulcer and/or severe thinning where corneal stromal integrity has been severely compromised, and surgical intervention with a tectonic graft remains the only option, albeit of last resort. Pre-formed, bioengineered corneal buttons would be difficult to place within an irregularly shaped corneal stromal ulcer and may not be mechanically stable enough to merit lamellar or full-thickness excision of diseased corneal tissue.

Hydrogels are high water content, biocompatible materials commonly used to mimic the native extracellular matrix (ECM) for 3D cell encapsulation, tissue engineering, regenerative medicine, and drug delivery applications. While the native ECM is highly dynamic, with an ability to relax and dissipate stresses through the reorganization of physical crosslinks, commonly used hydrogel materials rely on covalent crosslinks that yield static, brittle network architectures, hindering cell infiltration, migration, and remodeling. To overcome these limitations, recent efforts to develop adaptable hydrogel biomaterials have incorporated reversible crosslinks that better recapitulate the cellular microenvironment. Because dynamic linkages can break and re-form in response to cellular forces, adaptable hydrogels facilitate the complex cellular functions that occur in living organisms, enabling more rigorous studies of cell-matrix interactions and better functional restoration in tissue engineering applications.

In adaptable hydrogels, cell-instructive bulk properties such as stiffness, viscoelasticity, and macromolecule transport are directly dictated by the binding thermodynamics and kinetics of the dynamic linkages. However, present strategies to incorporate reversible crosslinks in biomimetic scaffolds utilize a relatively small number of dynamic covalent chemical reactions (e.g., hydrazone and Diels-Alder reactions) and host-guest interactions (e.g., cyclodextrin-adamantane motifs). Although adaptable hydrogels comprising these dynamic linkages have shown great promise for cell encapsulation and drug delivery, the crosslink affinity range accessible using these crosslinking chemistries is limited. Illustratively, while supramolecular hydrogels made from polymers with pendant macrocyclic host groups and pendant guest molecules are a promising class of soft materials that exhibit shear-thinning flow, self-healing, and stress relaxation.

There is an unfilled need for effective in-situ forming methodologies and compositions to non-invasively fill, stabilize and regenerate wounds of the eye and in the particular the cornea and ocular surface, and especially in patients where the risks and morbidities associated with penetrating the globe are high. Further development of useful gels is of interest.

SUMMARY

Compositions, kits and methods are provided for use as in-situ forming tissue constructs, also referred to as a defined hydrogel structure, that can be cellularized to aid in wound healing and tissue regeneration, particularly in repair, regeneration, and/or reconstruction of lamellar or partial defects of wounded corneal tissue or the ocular surface (e.g. the conjunctiva). Acellular constructs are also useful in aiding tissue regeneration. The compositions, kits and methods find also use in the repair, regeneration, and/or reconstruction of skin, subcutaneous tissue, nerve, muscle, bone, cartilage, vitreous, tendon, ligament, fat, retinal, conjunctival, scleral, cardiac, adrenal, and other types of tissue.

Provided are flowable biomaterial compositions and hydrogels derived therefrom, comprising a biopolymer such as a structural protein, e.g. various types of collagen or gelatin; polysaccharides, e.g. hyaluronic acid, alginate, cellulose, elastin, chitosan, dextran; PEG, multi-arm PEG, poloxamers, etc., and combinations thereof, which biopolymer has been modified so as to form a defined hydrogel structure at a site of application, e.g. a supramolecular assembly of hyaluronic acid via host-guest interactions. A supramolecular structure may be defined as a well-defined complex of molecules held together by noncovalent interactions, e.g. hydrogen bonds, van der waals forces, electrostatic interactions, and combinations thereof. For such supramolecular structures the flowable biomaterial may be provided as a single, self-healing, shear-thinning mixture, where the single composition can be injected into or onto a wound site without the need for mixing, and it will take on the shape of the cavity without further stimulus or reaction. In some embodiments the biopolymer is gelatin, collagen, hyaluronic acid, or a combination thereof.

A defined hydrogel structure is formed by combining reactants that interact non-covalently to form a supramolecular structure. A flowable biomaterial for this purpose can be a single solution comprising the supramolecular structure, or can be two solutions combined immediately prior to administration, or at the site of administration, wherein the supramolecular complex is formed. In one such embodiment the defined hydrogel structure is formed by host-guest complexation chemistry. Non-limiting examples include biopolymers conjugated to a cyclodextrin (CD) moiety combined with biopolymers conjugated to an adamantane (Ad) moiety; and biopolymers conjugated to Cucurbit[n] urils (CB[n], n=5-8 and 10) combined with biopolymers conjugated to an adamantane (Ad) moiety.

In some embodiments the hydrogel comprises cucurbit [8]uril (CB[8])-based crosslinks that form on demand via thiol-ene reactions between preassembled CB[8]·peptide ternary complexes and grafted norbornenes, which can crosslink through cucurbit[8]uril (CB[8]) homoternary complexes formed by simultaneous inclusion of two guest molecules in one CB[8] cavitand. Light-initiated thiol-ene reactions between the CB[8].FGGC peptide ternary complexes and grafted norbornenes are used to rapidly crosslink the cell-adhesive biopolymer into a supramolecular hydrogel. In some embodiments the biopolymer is a protein, e.g. various types of collagen, gelatin, elastin, etc.; polysaccharides, e.g. hyaluronic acid, chondroitin sulfate, heparan sulfate, dermatan sulfate or related sulfonated glycosaminoglycans, alginate, cellulose, chitosan, dextran; synthetic polymers such as PEG, multi-arm PEG, poloxamers, etc., and combinations thereof, which biopolymer has been modified by in situ conjugation with the pre-assembled CB[8]-guest complexes. In some embodiments the peptide is an PheGlyGlyCys peptide.

In situ conjugation of the pre-assembled CB[8]-guest complexes to the biopolymer backbone overcomes limitations of previous CB[8]-based hydrogels and supramolecular materials by eliminating the need for a second synthetic, chain-growth polymer network while still enabling rapid, on demand gelation. These CB[8]-based hydrogels exhibited favorable optical properties and are injectable in the gelled state. Cells encapsulated in these hydrogels remained highly viable and uniformly distributed throughout the gels for at least seven days in culture.

The flowable biomaterial and hydrogels derived therefrom may comprise cells or therapeutic agents, or both, that aid in treating or reconstructing a surgically incised or wounded area, where the cells or agent are entrapped or encapsulated in the defined hydrogel structure. Cells of interest include regenerative cells, such as a stem cell, including without limitation corneal stem cells. Cells suitable for treating corneal tissue may include, for example, one or more of keratocytes, keratinocytes, limbal corneal epithelial cells, corneal endothelial cells, and corneal stromal stem cells. Mesenchymal stem cells or mesenchymal stromal cells derived from various tissue sources (e.g. bone marrow, adipose tissue, muscle, skin, or cornea) may also be encapsulated within the gel of the present invention. Therapeutic agents that can be included within the hydrogel include but are not limited to steroids, anti-inflammatory agents (e.g. NSAIDs), small-molecule drugs, therapeutic proteins such as antibodies, growth factors, cytokines, and the like; etc. Examples of growth factors include but are not limited to epidermal growth factor (EGF), hepatocyte growth factor (HGF), keratinocyte growth factor (KGF), nerve growth factor (NGF), thymosin beta 4, fibroblast growth factor (FGF) and its subtypes, insulin-like growth factor (IGF) and its subtypes, derivatives (including recombinant forms of these factors) or combinations thereof. A multitude of growth factors can also be included, such as secreted factors harvested from various cells such as mesenchymal stem cells or mesenchymal stromal cells of varying tissue sources including but not limited to the bone marrow or cornea.

In some embodiments, a flowable biomaterial composition for use as an in-situ-forming corneal construct, i.e. a defined hydrogel structure, is provided, which finds use in treating or reconstructing a surgically incised or wounded cornea and/or the conjunctiva. For example, the hydrogel can adhere to wounded tissue and then allow for epithelial re-growth. In another embodiment, the hydrogel is used to treat damage in other parts of the eye or orbit, via injection of the material in a space such as the subretinal space, suprachoroidal space, anterior chamber, subconjunctival space, subtenon's space, periorbital space, orbital space, or vitreous cavity. The biomaterial forms a gel through supramolecular interactions within said space either alone, or with cellular or extracellular additives such as biomolecules or drugs. The gel can be used as a space-occupying material to create space or volume within a potential space, with or without cells or therapeutic agents within it. In some embodiments the flowable biomaterial is applied to an existing cavity or lumen, which can be highly irregular in shape, e.g. a pathologic cavity such as an ulcer. In some embodiments a cavity is debrided to eliminate necrotic material and create fresh wound edges. In some embodiments a cavity is created, e.g. with surgical instruments, or a laser, for example to remove tissue that is scarred, fibrotic, opacified, etc. In other embodiments, the gel is applied to and allowed to coat an entire surface (e.g. the ocular surface) or applied to a space (including a potential space) such as the ocular surface under eyelids, or the pleural space or the viscera where there may be a thin layer of fluid between tissue surfaces. In still other embodiments, the gel is injected directly into a tissue including stromal tissue of the eye, skin, muscle, or other organs.

In yet another aspect, the instant disclosure provides a kit for making a corneal construct for use in treating or reconstructing a surgically incised or wounded corneal area in a mammalian subject. A kit will comprise a flowable biomaterial that forms a defined hydrogel structure at the site under ambient conditions. The defined hydrogel is effective in treating or reconstructing a wounded corneal area. The flowable biomaterial may be provided as a single composition that is injected through a syringe, tube, cannula, port, or needle, or may be provided as two compositions in separate containers.

BRIEF DESCRIPTION OF THE FIGURES

(FIG. 1A) Schematic illustration for the cornea after application of the s-HA hydrogel. (FIG. 1B) Cell viability of hCECs live in green and dead in red encapsulated in s-HA hydrogel before and after passing through a needle (scale bar: 100 μm). (FIG. 1C) Quantification of live/dead staining indicates high viability after injection through 18, 20, 23, 26 and 30 gauge needles (n=3). (FIG. 1D) Quantification for the degradation rate of s-HA hydrogel with and without hyaluronidase (n=3). (FIG. 1E) s-HA hydrogel stained with a magenta dye 1) before and 2) after degradation by the addition of excess CD. (FIG. 1F) Transmittance profile of s-HA hydrogel and PROVISC HA gel at day 0, 1 and 4. (G) SEM images of s-HA hydrogel at day 0, 4 and 10 show increase in pore size over time. (H) Quantification for the pore density change at day 4*p=0.0184 vs. day 0; and day 10***p<0.0001 vs. day 0

Figure 1A:
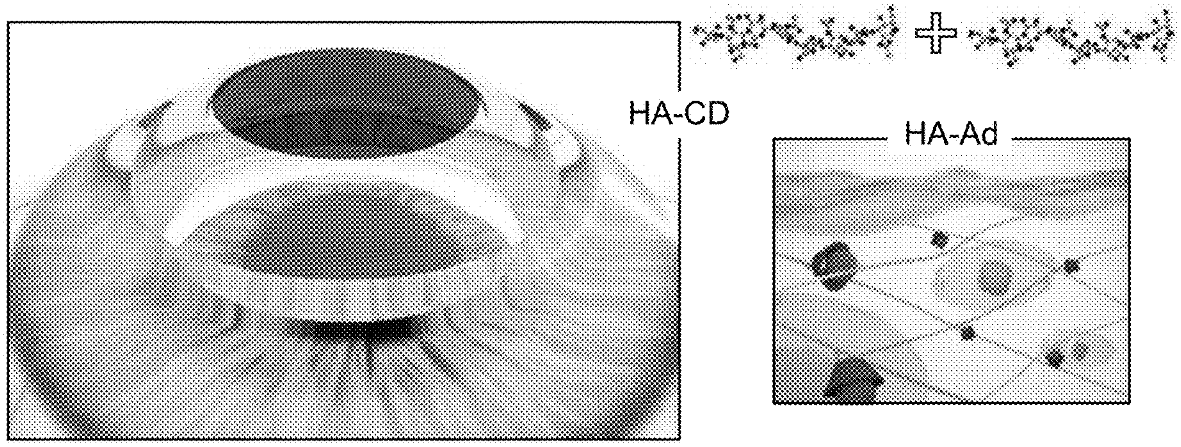
FIG. 1A-1H shows the biophysical properties of supramolecular HA (s-HA) hydrogels.
Figure 1B:
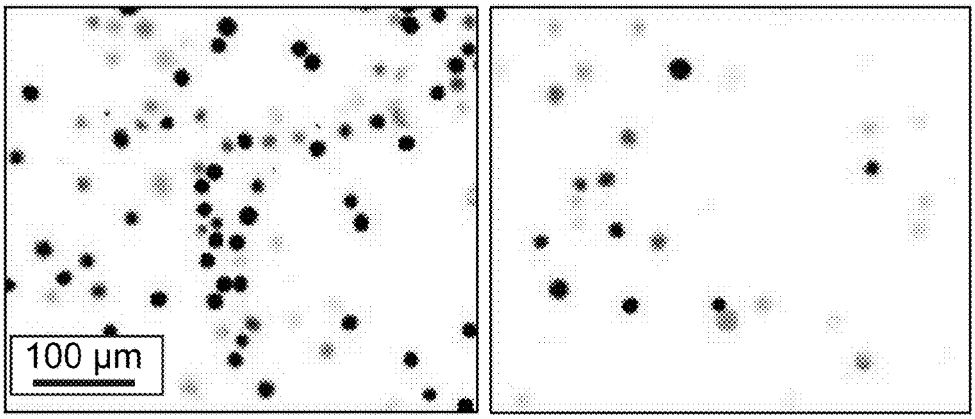
Figure 1C:
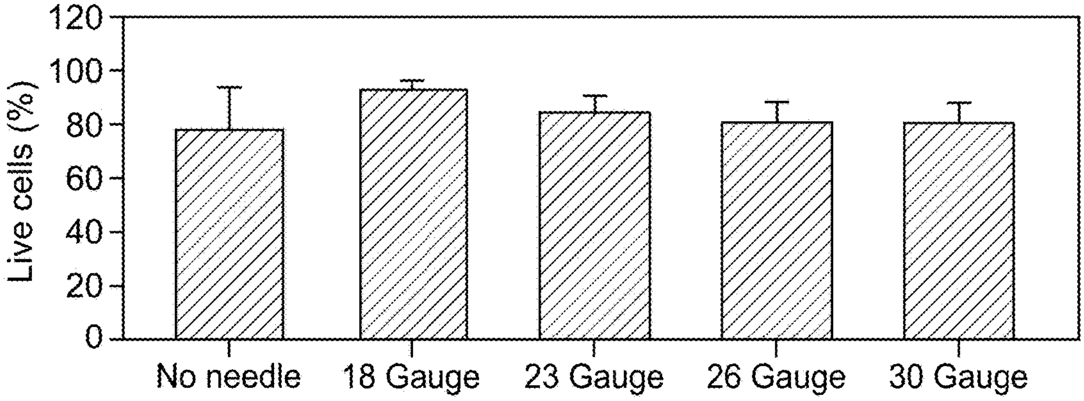
Figure 1D:
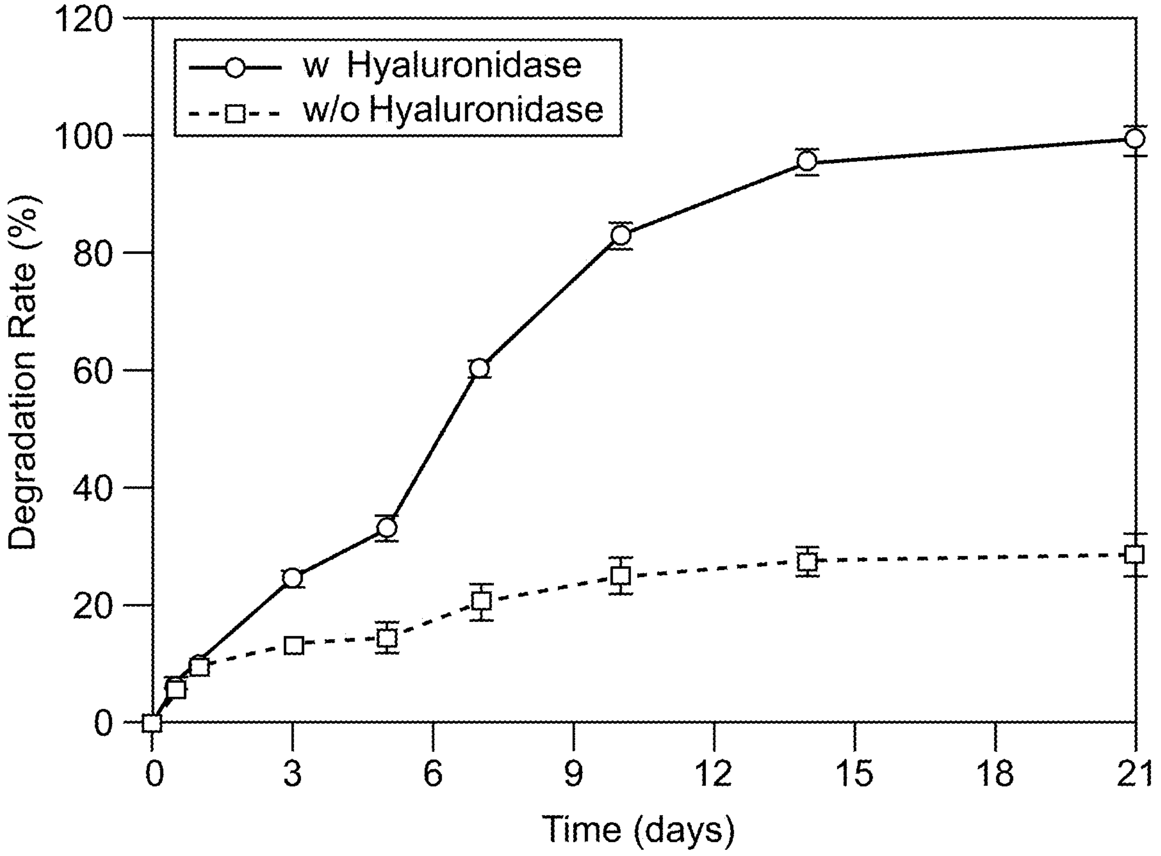
Figure 1E:
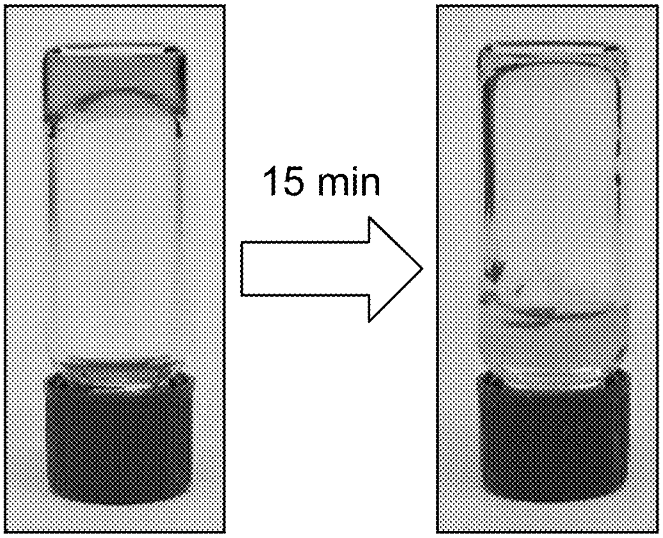
Figure 1F:
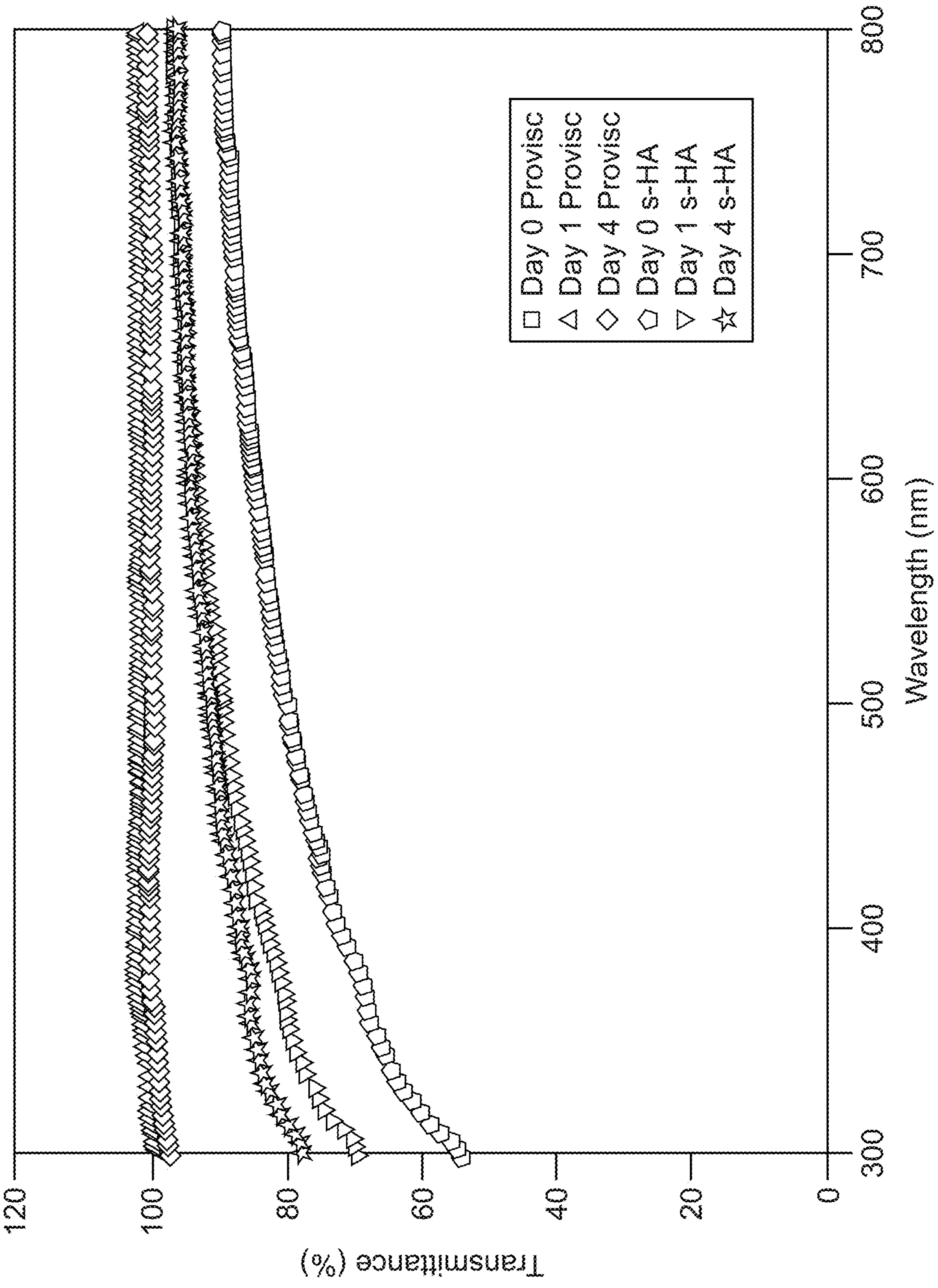
Figure 1G:
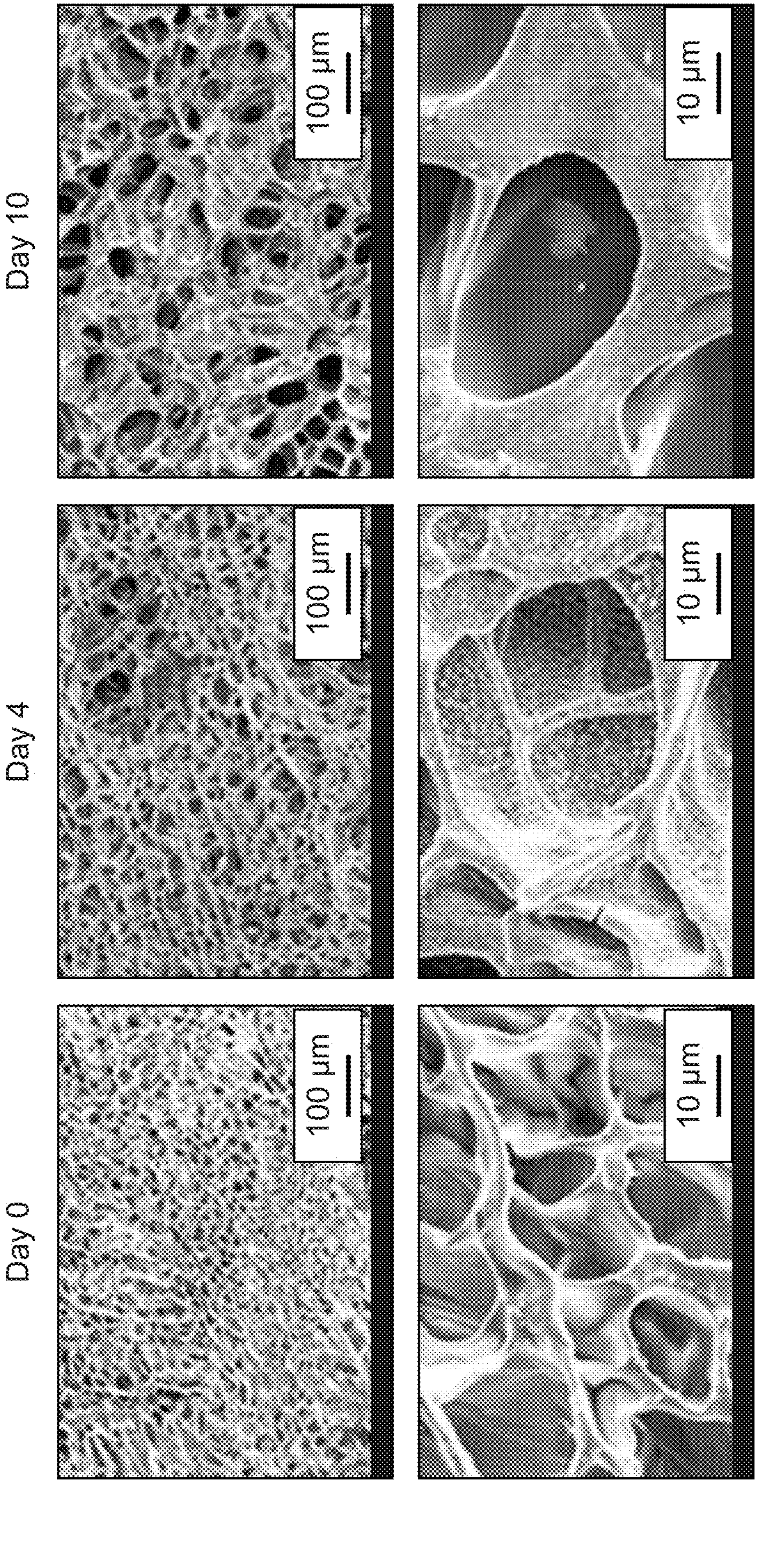
Figure 1H:
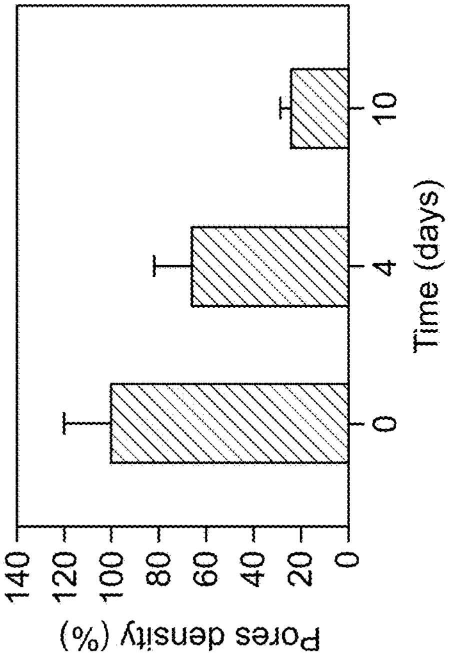
Figure 2A:
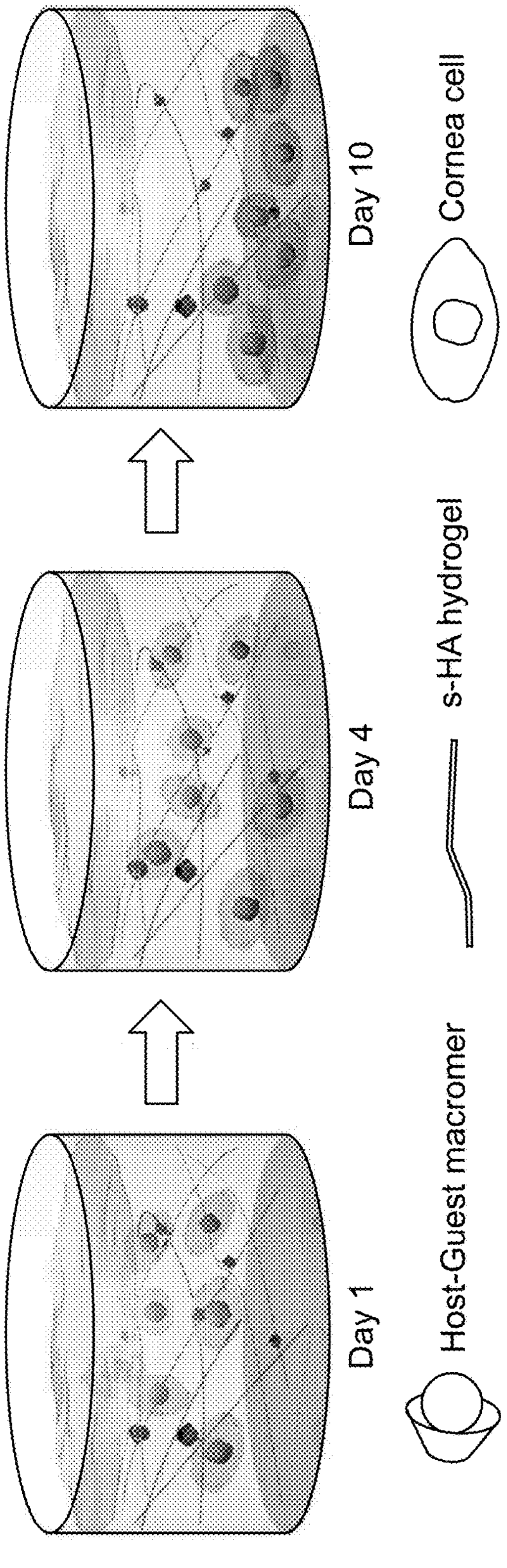
Figure 2B:
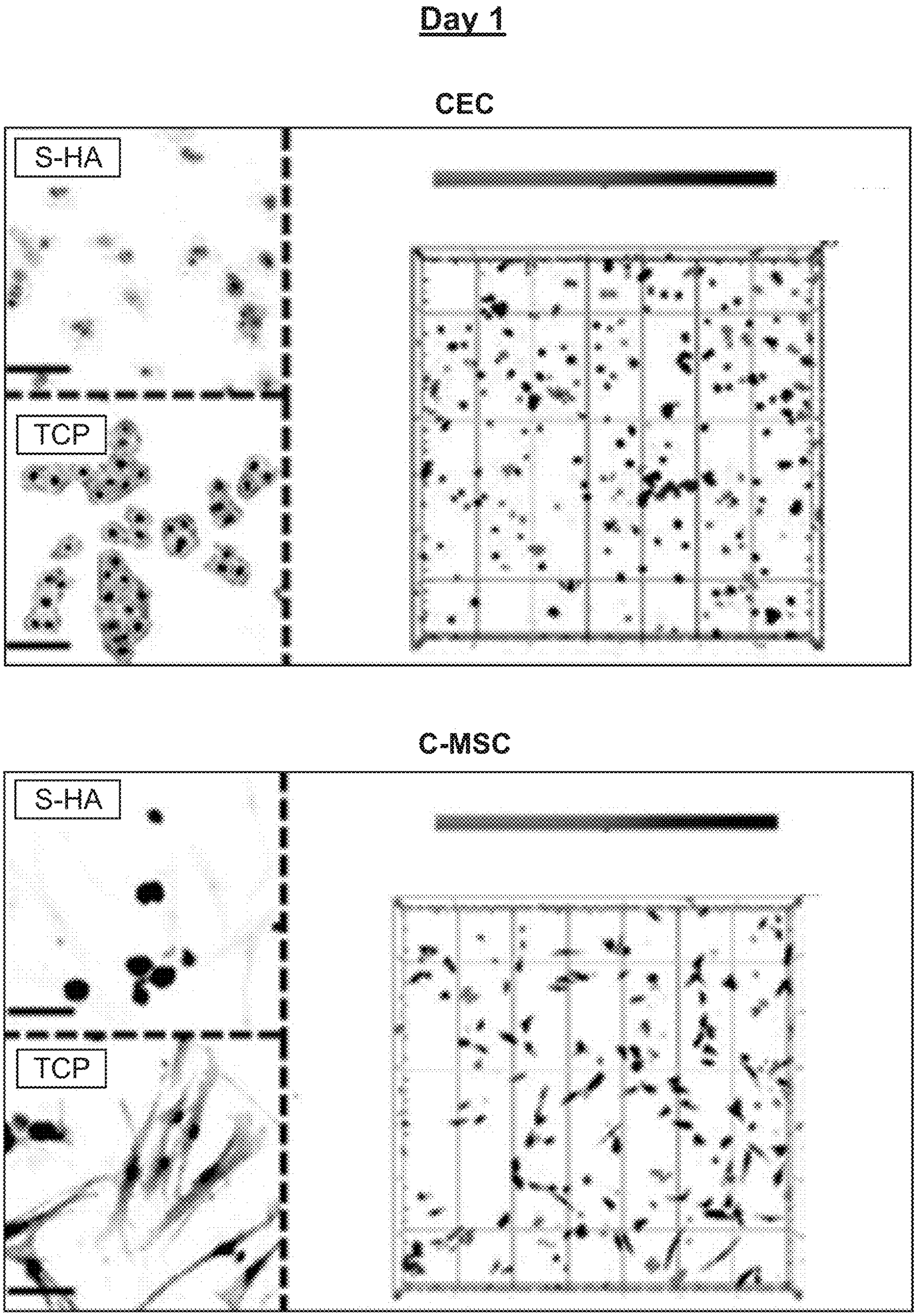
Figure 2B:
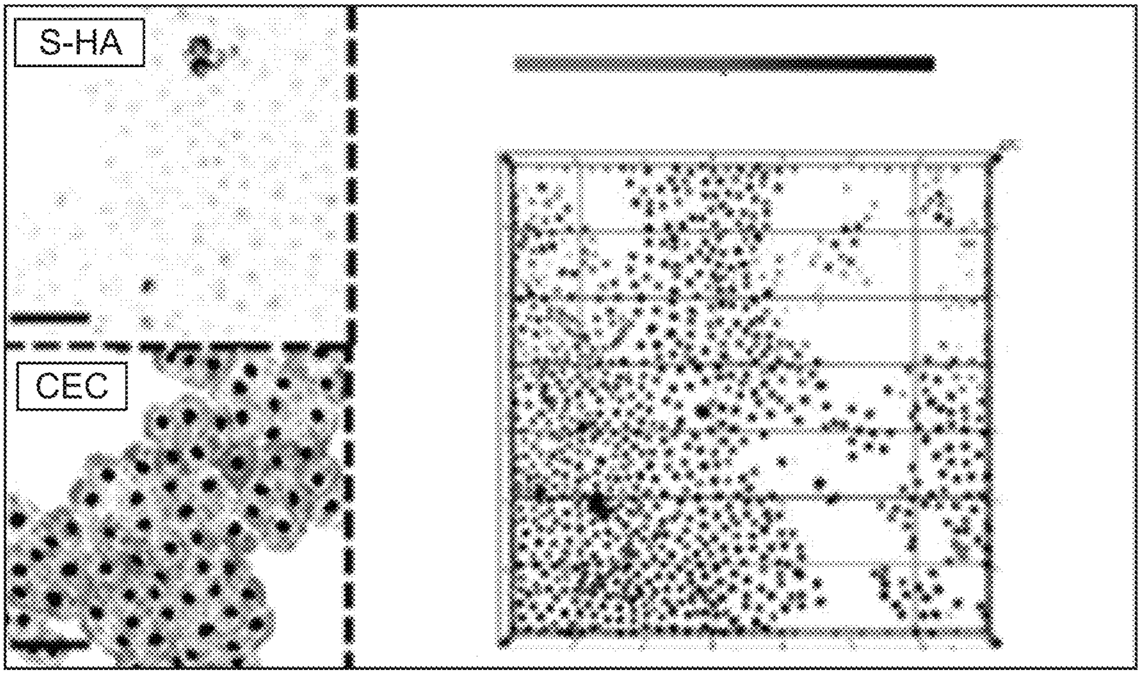
Figure 2B:
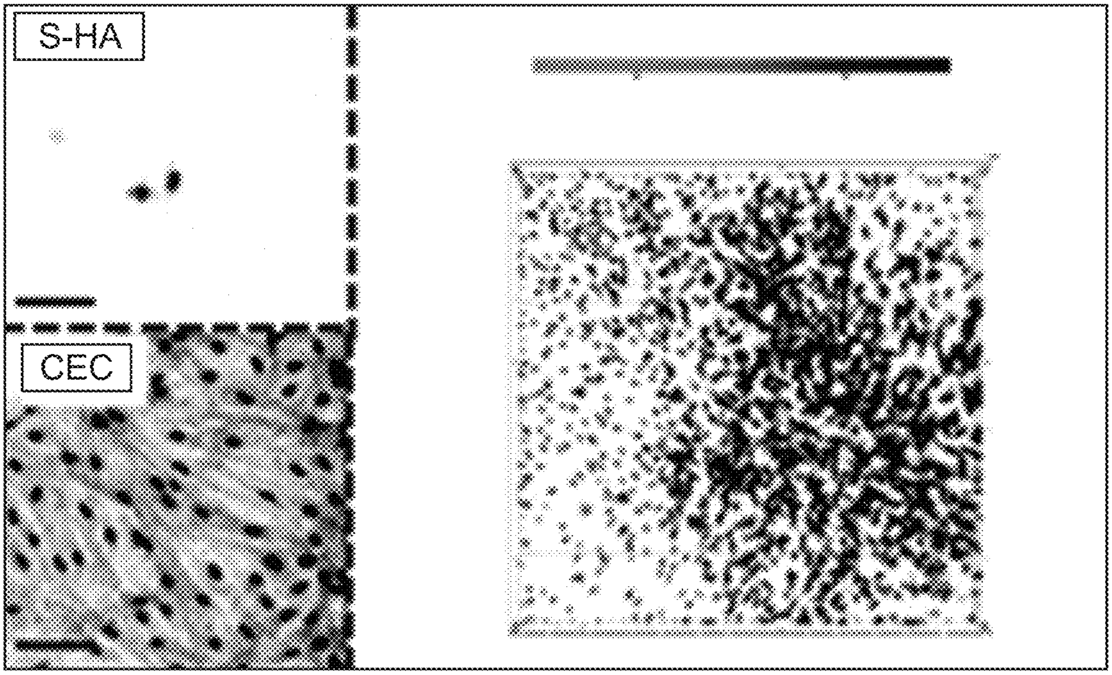
Figure 2B:
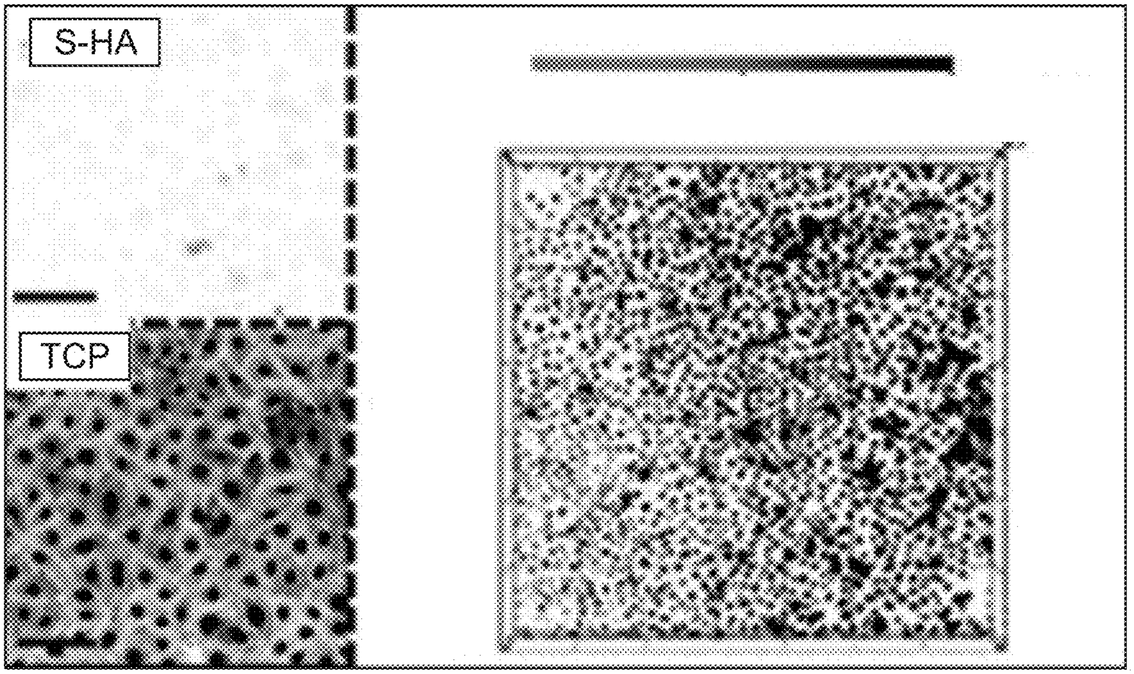
Figure 2B:
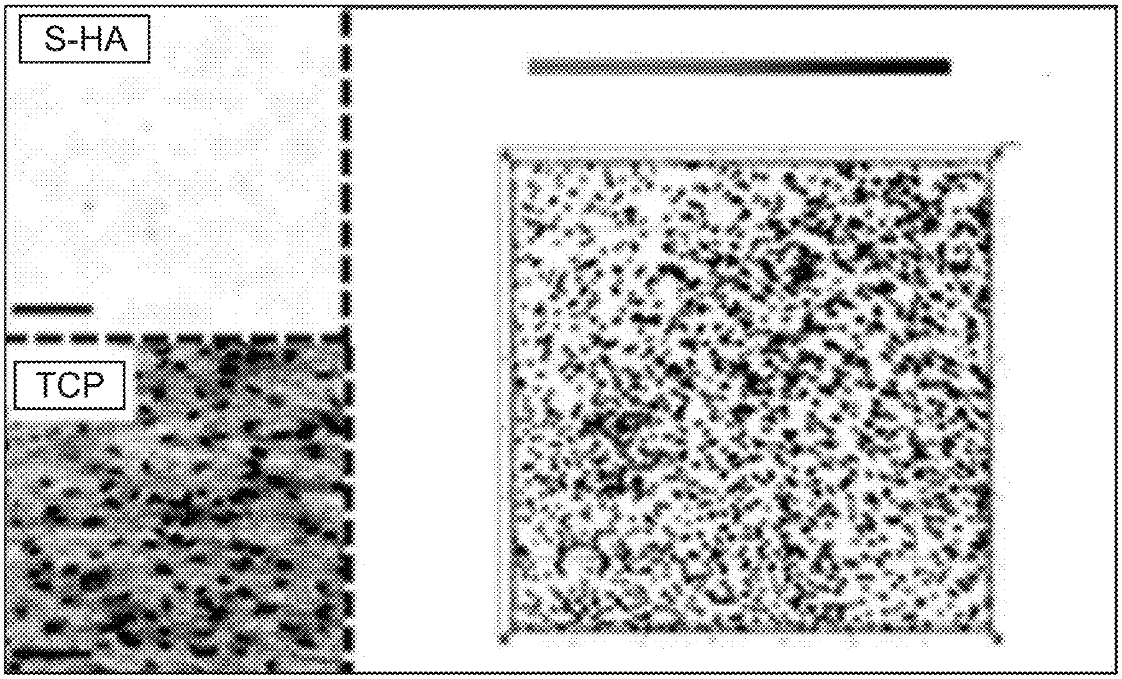
Figure 2C:
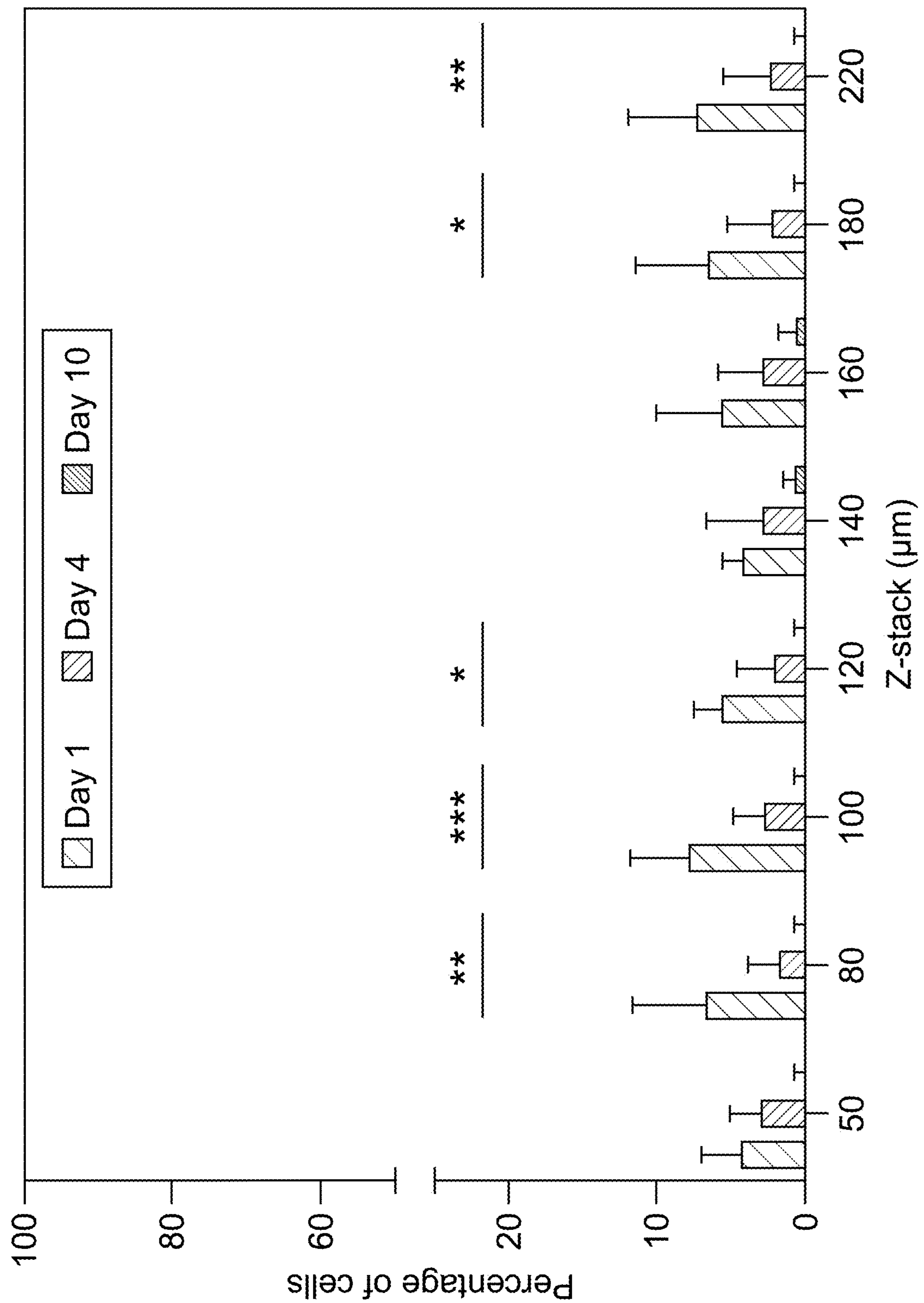
Figure 2D:
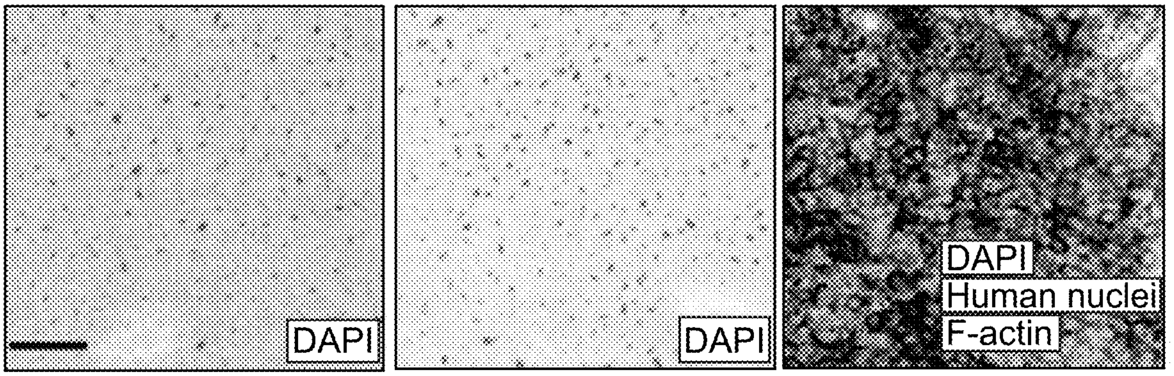
Figure 2E:
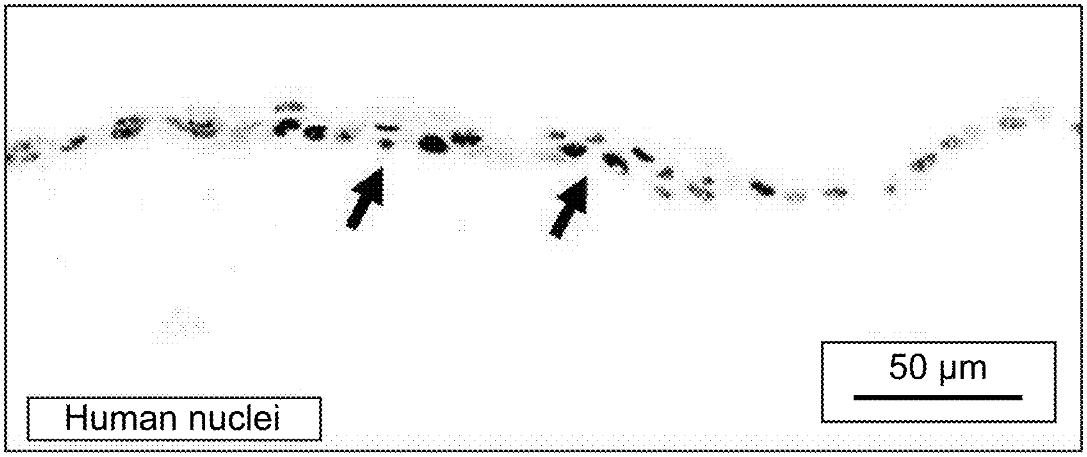
Figure 2F:
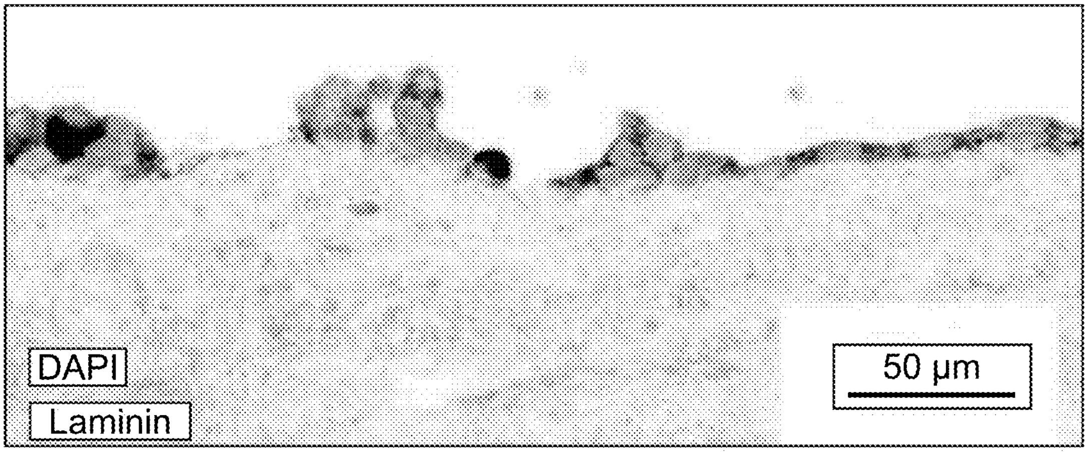
Figure 3A:
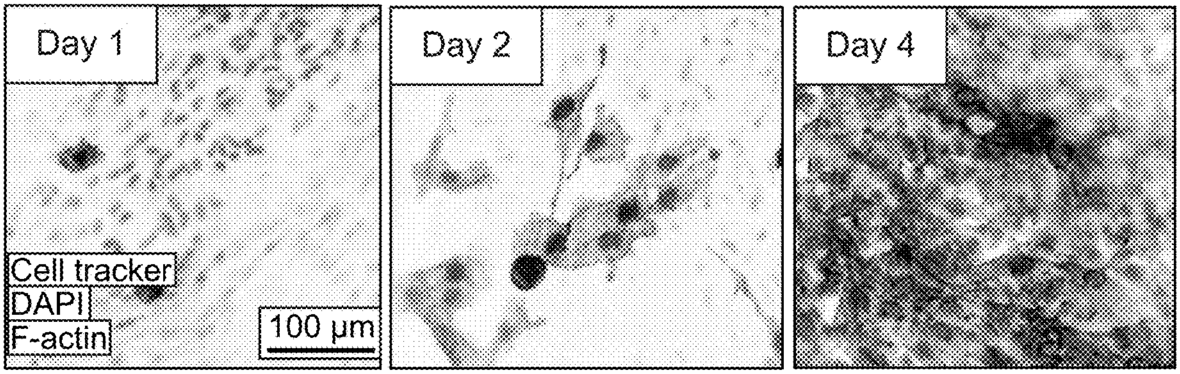
Figure 3B:
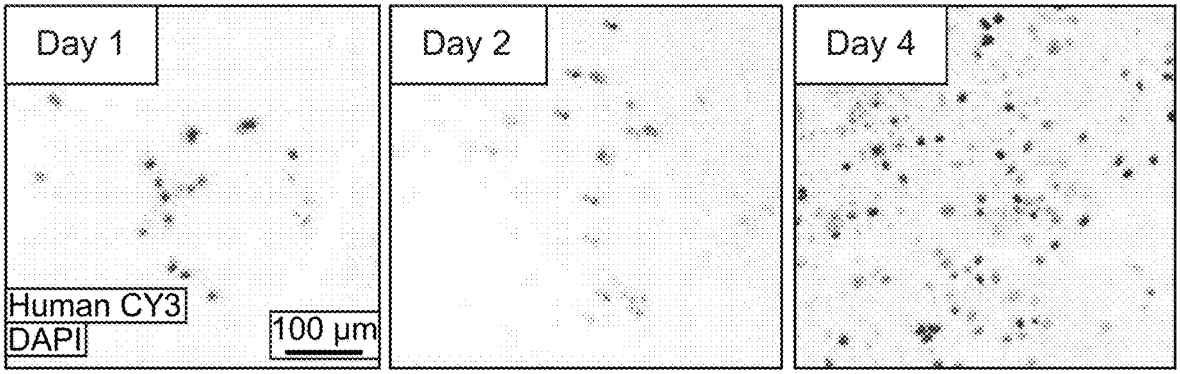
Figure 3C:
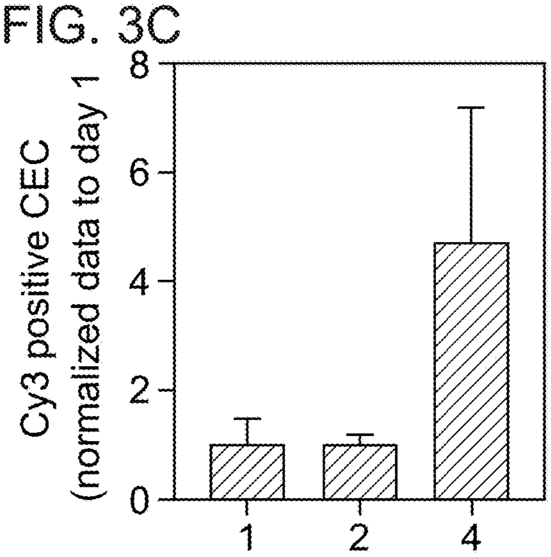
Figure 3D:
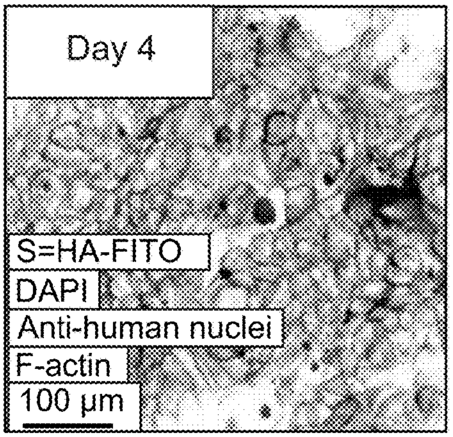

(n=4). Ordinary one-way ANOVA ($p<0.005$) was used to detect statistical differences followed by Dunnett's multiple comparisons test.

FIG. 2A-2F shows the spatio-temporal behavior of corneal cells encapsulated within s-HA hydrogels. (FIG. 2A) Schematic illustration for the behavior of encapsulated corneal cells at day 1, 4 and 10. At day 0 most cornea cells are present throughout s-HA hydrogel layers; at day 4 some cells adhere to the TCP while others continue to be present through the hydrogel layers; at day 10 all cells adhere and spread on the TCP. (FIG. 2B) Confocal images of encapsulated cornea cells in s-HA hydrogel stained with Phalloidin exhibiting F-actin on the TCP and within the hydrogel at day 1, 4 and 10 (green for hCEC; red for C-MSC; blue for DAPI, scale bar: 100 μm). The 3D images show the depth of the cornea cells throughout the hydrogel. The different colors represent the layers where the cells belong; red—0 μm for the most outer layer and blue—220 μm for the 2D TCP. (FIG. 2C) Quantification of the cell distribution within the s-HA hydrogel at day 1, 4 and 10 (n=8); the percentage of cells distributed within the same layer as day 1 statistically decreases at 4 (*$p<0.0001$, $p<0.001$, and *$p=0.03$) and at day 10 a few percentage of cells are observed within the hydrogel (FIG. 2D) Confocal images show that encapsulated hCEC in s-HA adhere to the stromal layer of ex vivo rabbit cornea after 4 days, whereas no hCEC encapsulated in linear HA is able to adhere to the cornea. hCECs are stained with human nuclei cy3 (green), Phalloidin (red) and DAPI (blue). DAPI staining shows stromal nucleus in all the groups (scale bar: 100 μm). Immunostaining of section of the corneas shows that hCEC staining with (FIG. 2E) anti-human nuclei cy3 (green) are able to form a double layer and (FIG. 2F) laminin (red) at day 4.

FIG. 3A-3D shows how s-HA hydrogels allows CEC adhesion on the stromal layer and the number of cells increase over time. (FIG. 3A) Confocal images show the adhesion and spread of hCEC marked with cell tracker in epithelial defect rabbit cornea model at day 1, 2 and 4; Cell tracker (red), F-actin (gray) and blue (DAPI), scale bar 100 μm. (FIG. 3B) Confocal images show the increase in adhesion of hCEC; anti-human nuclei cy3 (green) and DAPI (blue), scale bar: 100 μm. (FIG. 3C) Quantification of cy3 positive cells at day 1, 2 and 4. Cells positive for cy3 significantly increase *$p=0.048$ at day 4 vs. day 1 and 2; n=4 and data is presented as mean±SD, Ordinary one-way ANOVA ($p<0.005$) was used to detect statistical differences followed by Tukey's multiple comparisons test. (FIG. 3D) Confocal image shows the presence of s-HA-FITC and the hCEC in epithelial defect rabbit cornea model at day 4; anti-human nuclei (red), s-HA-FITC (green), F-actin (yellow), and DAPI (blue), scale bar: 100 μm.

Figure 4A:
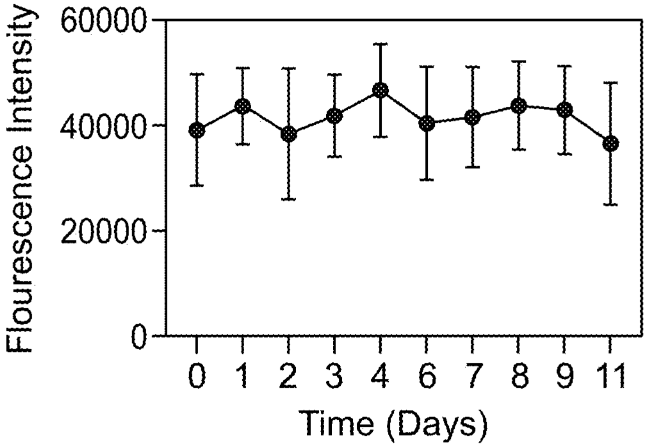
Figure 4C:
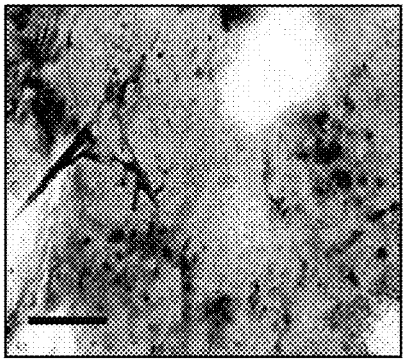
Figure 4B:
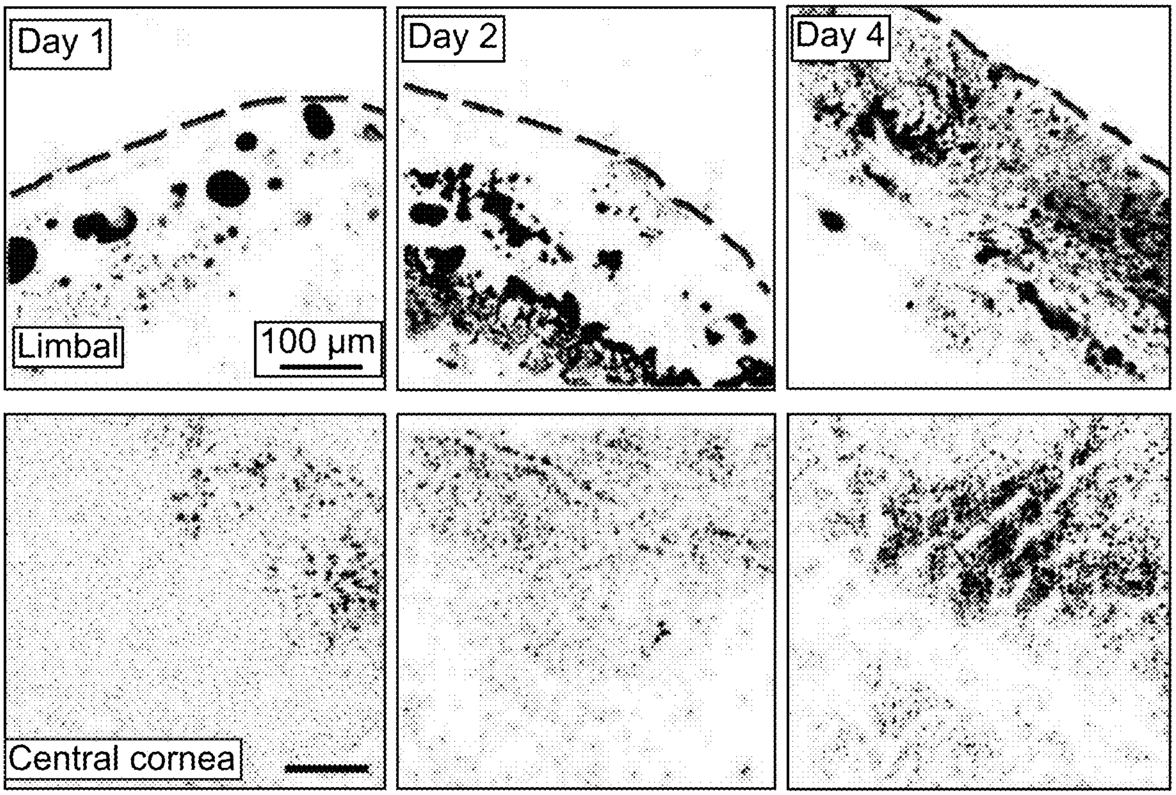
Figure 5B:
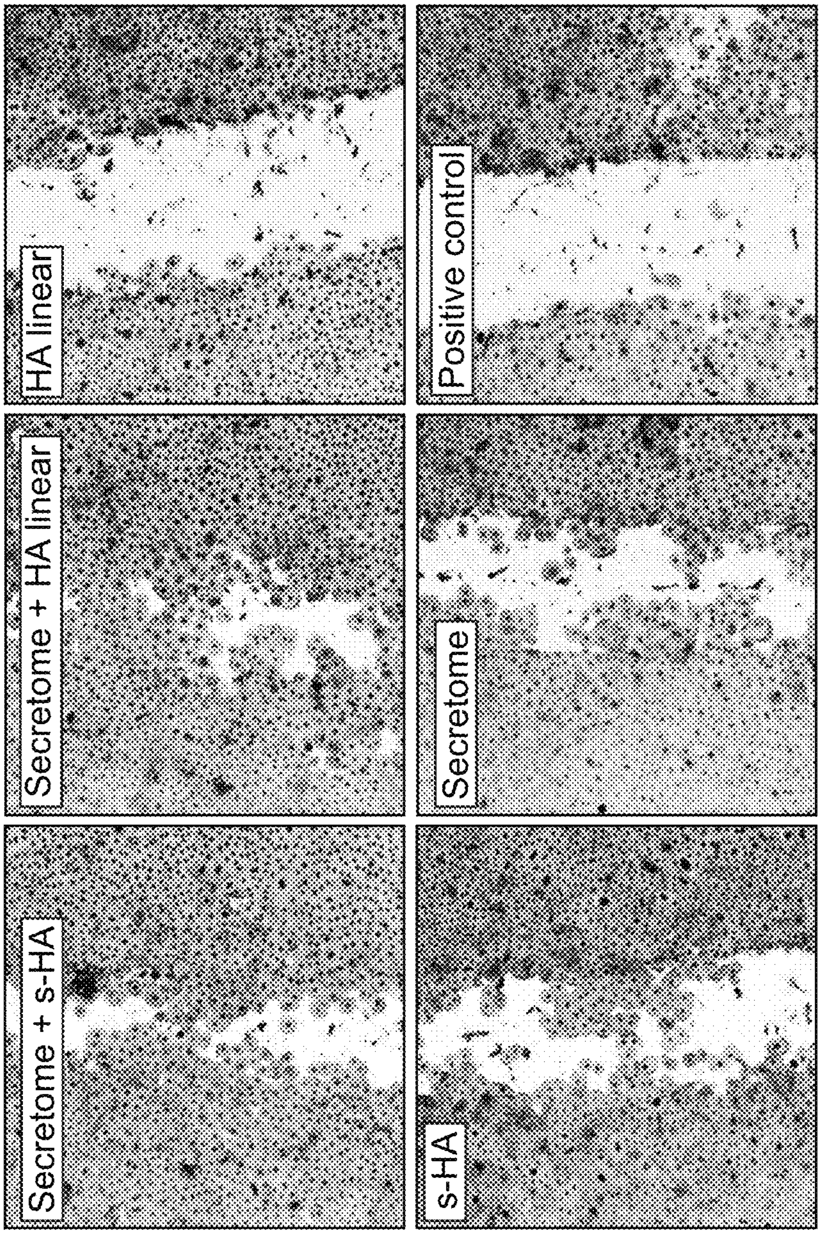
Figure 5A:
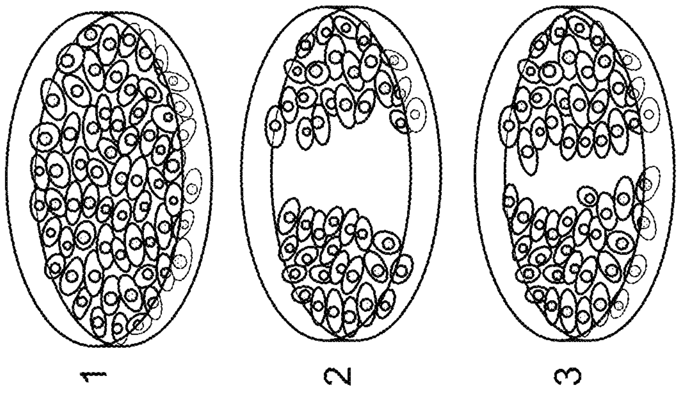
Figure 5C:
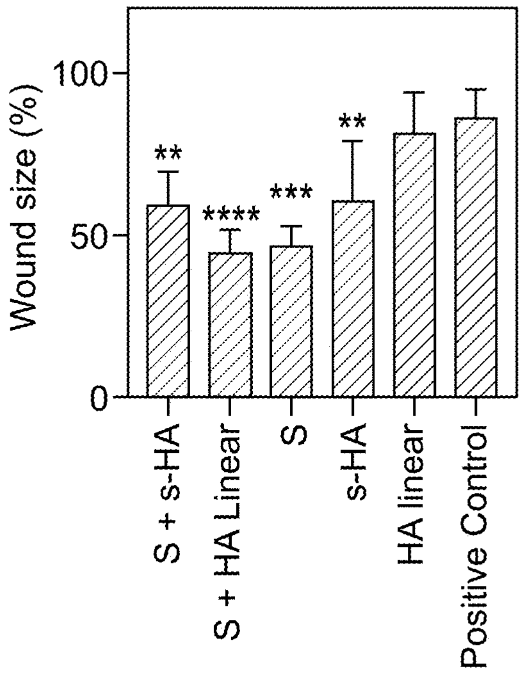
Figure 5D:
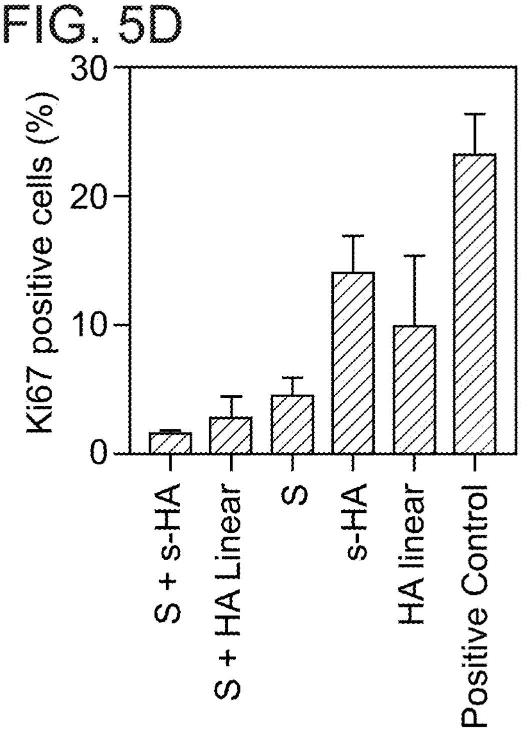
Figure 5E:
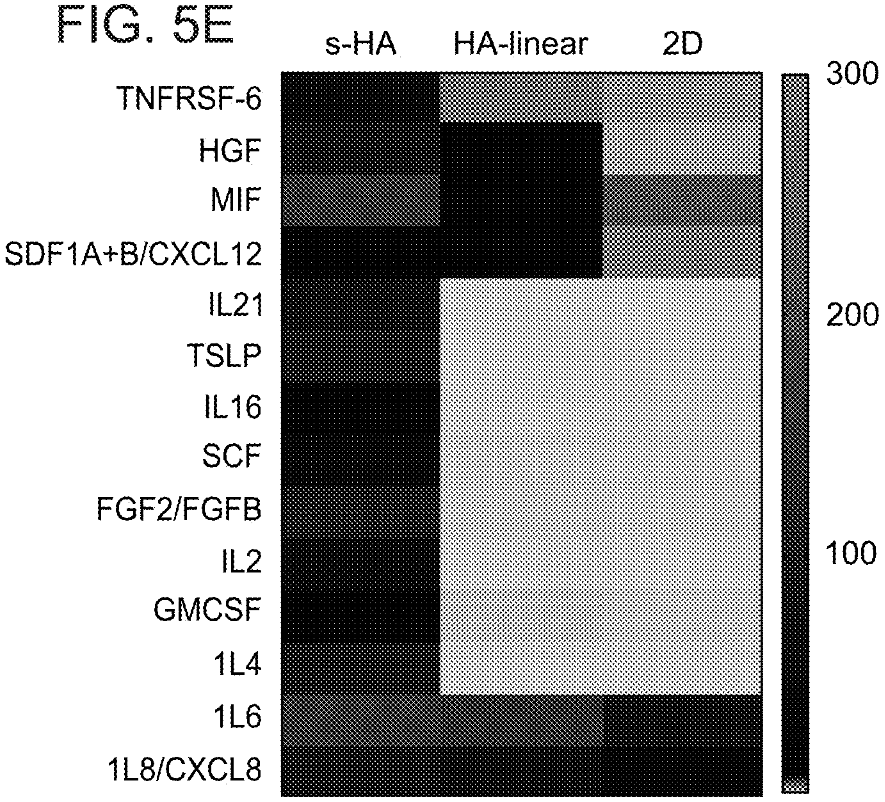
Figure 6A:
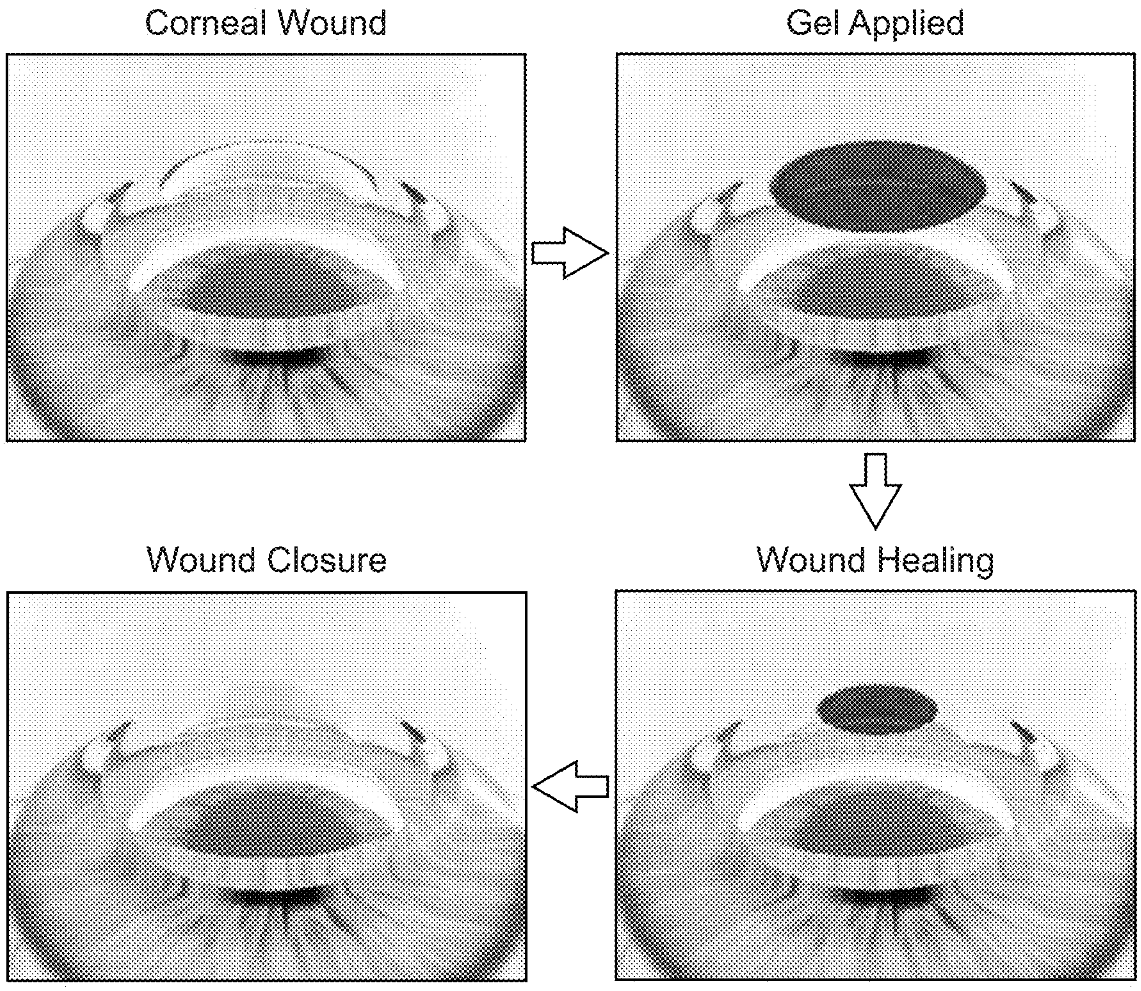
Figure 6B:
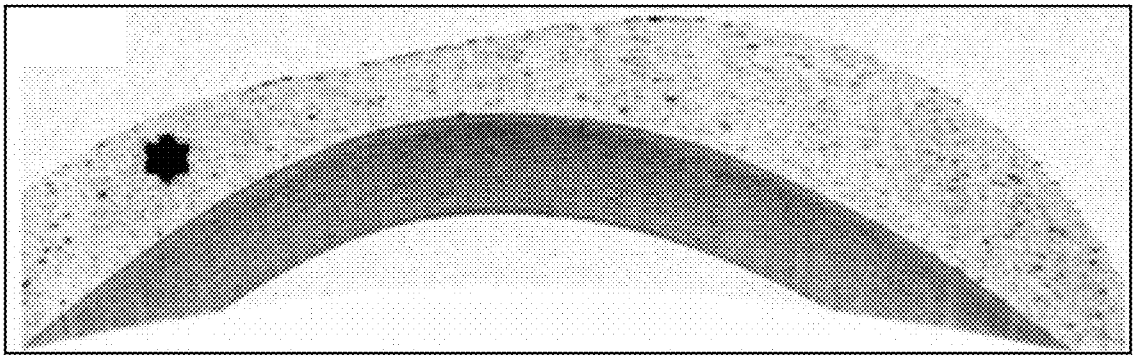
Figure 6C:
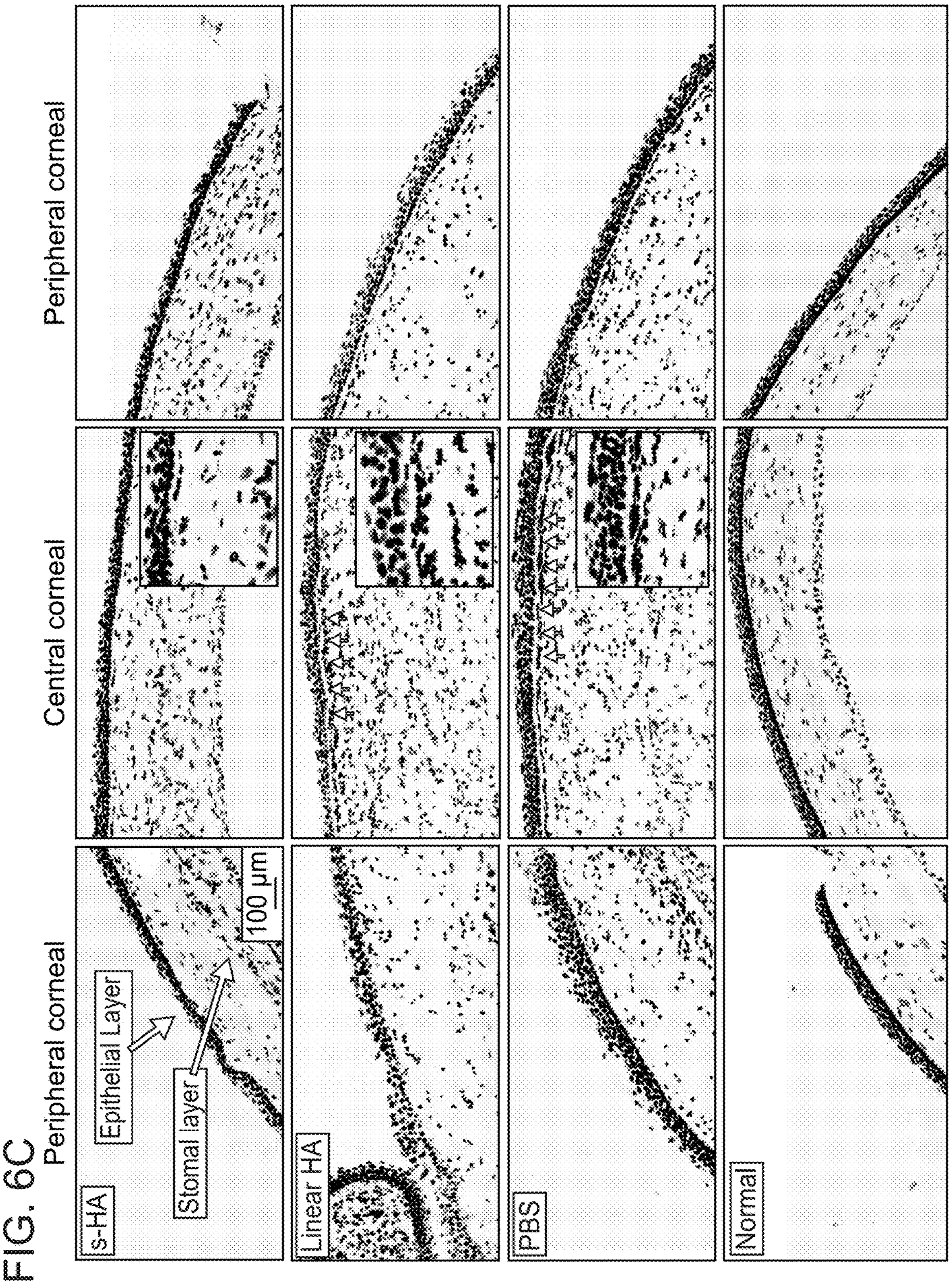
Figure 6D:
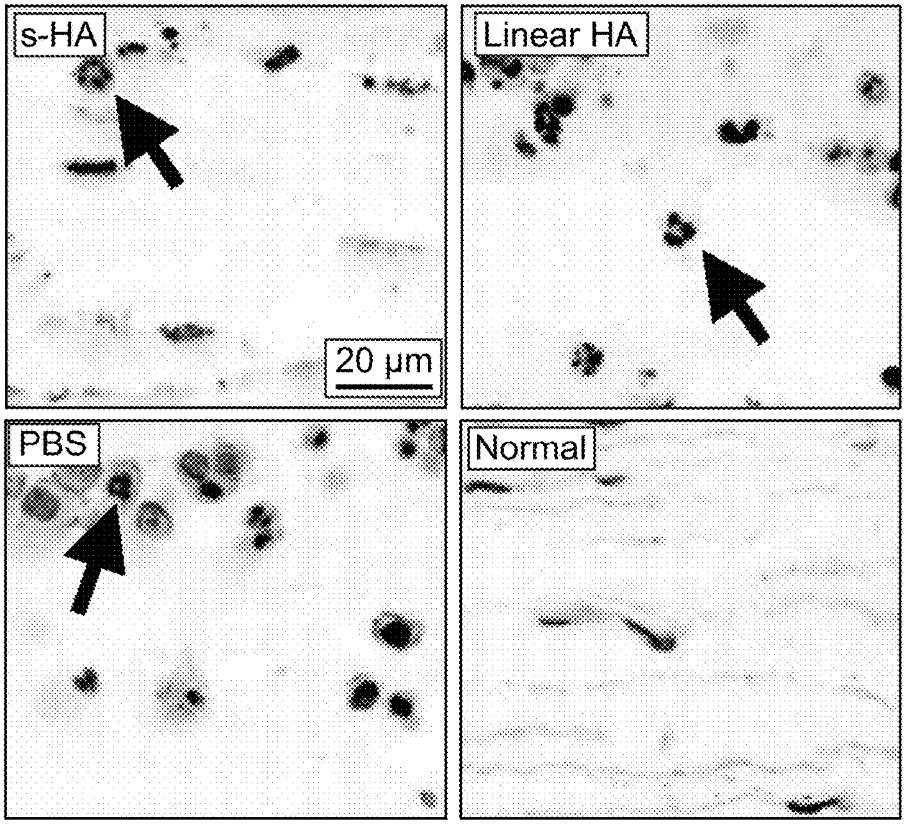
Figure 6E:
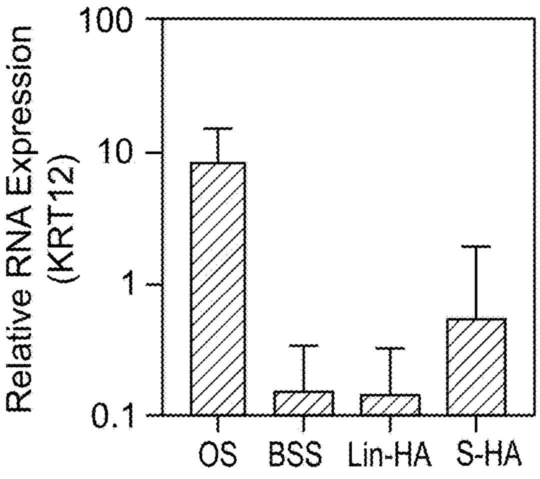
Figure 6F:
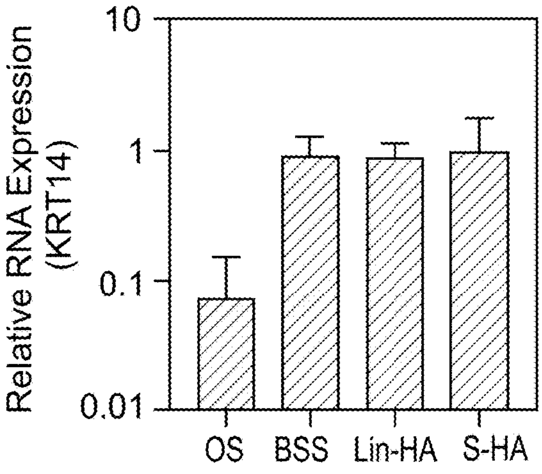
Figure 6G:
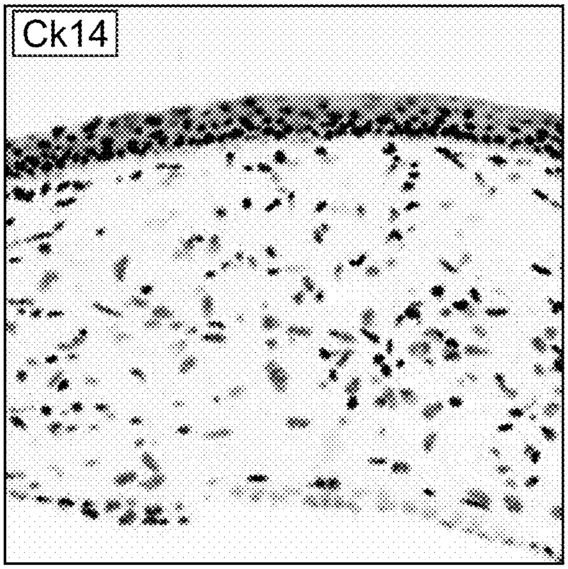
Figure 6H:
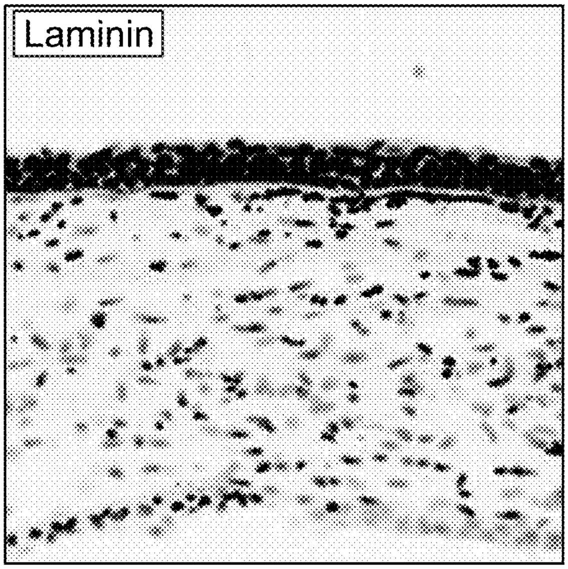
Figure 6I:
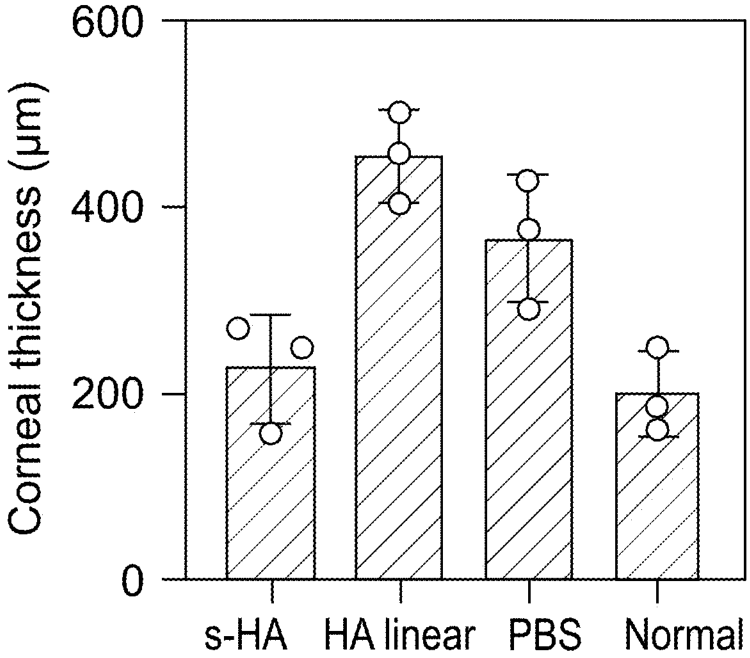
Figure 6J:
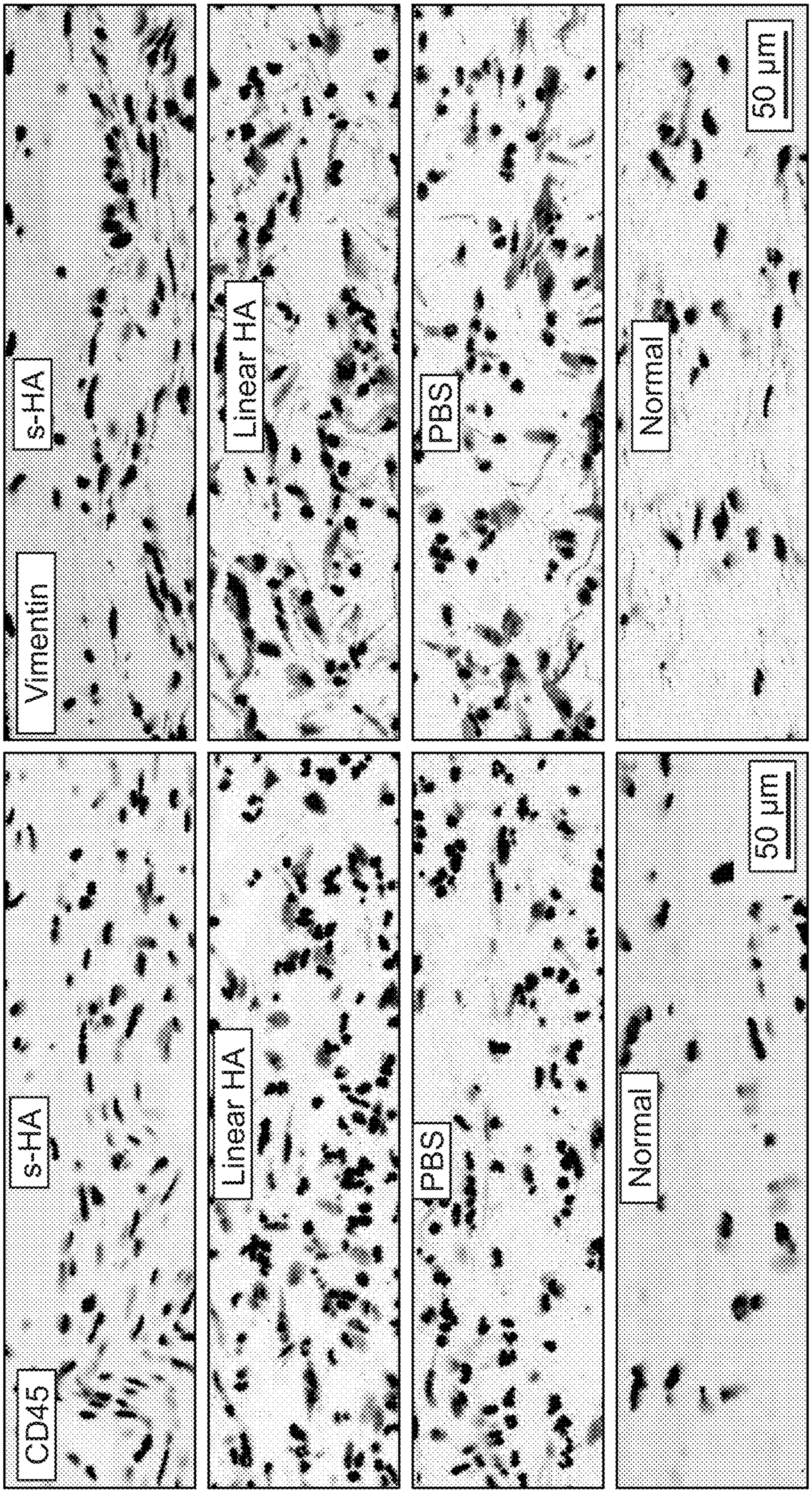
Figure 6K:
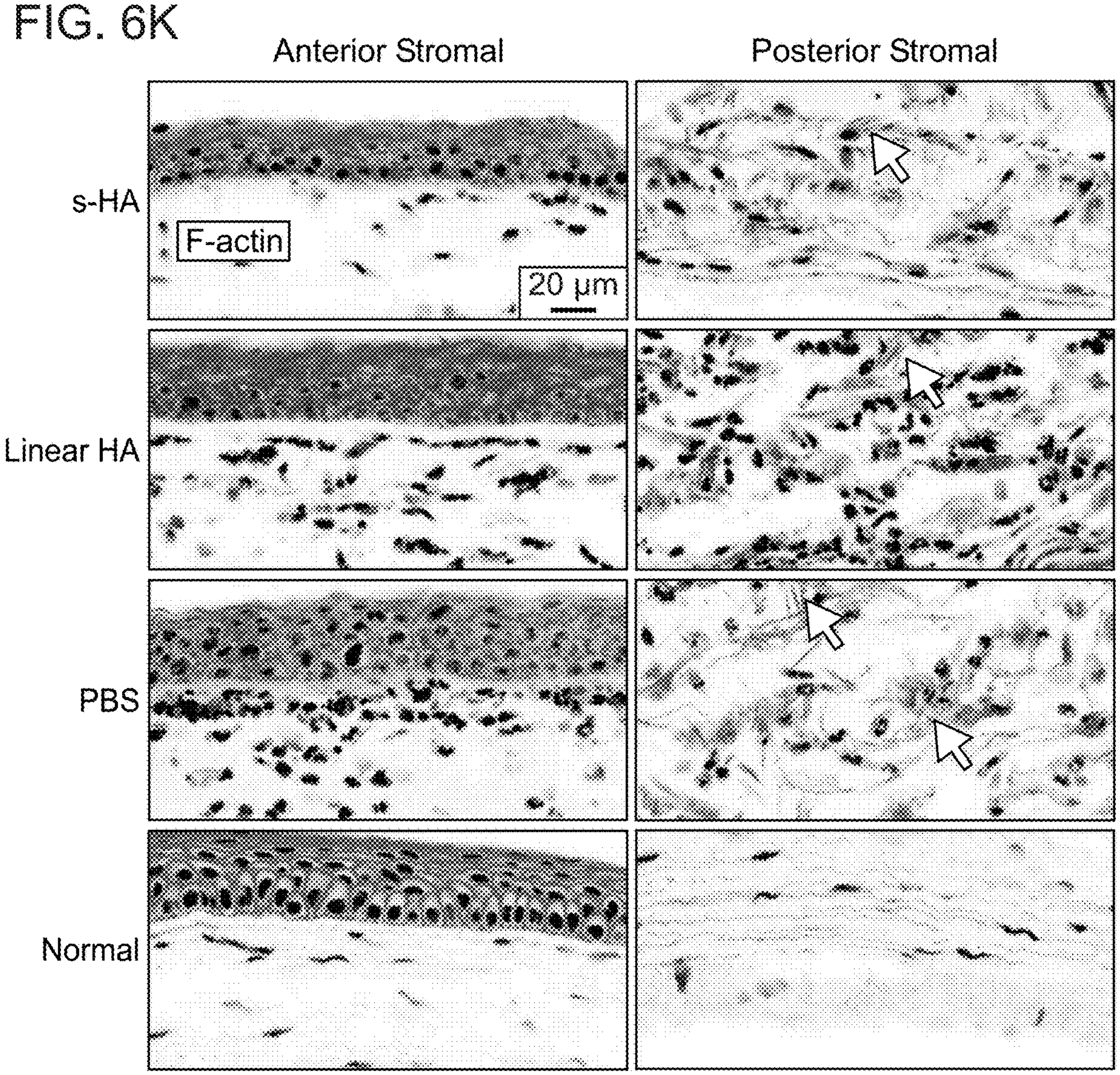

FIG. 4A-4C presents fluorescence data showing s-HA hydrogel application to wounded cornea. (FIG. 4A) Fluorescence intensity of s-HA-FITC after 10 days in PBS. (FIG. 4B) Confocal images showing s-HA-FITC in the limbal and central corneas at day 1, 2 and 4 after epithelial debridement. Scale bar: 100 μm. (FIG. 4C) HA-FTIC (green) adsorbed into the epithelial layer (red) near limbal area.

FIG. 5A-5E shows how s-HA hydrogel modulates in vitro hCEC wound healing and c-MSC secretome profile. (FIG. 5A) Schematic in vitro wound healing model. (FIG. 5B) Ki67 (magenta) and F-actin (green) expression in hCEC treated with s-HA hydrogel plus c-MSCs secretome, linear HA pus c-MSCs secretome, linear HA, s-HA and secretome alone and complete medium (positive control) 72 h after wound (scale bar: 100 pixel). (FIG. 5C) quantification of the wound size (%) 72 hours after wound (n=3). Wound size significantly decreased for the hCEC treated with s-HA and linear HA plus secretome compared to positive control. hCEC wound size also decreased by treating the cells with s-HA alone compared to positive control. Ordinary one-way ANOVA ($p<0.005$) was used to detect statistical differences followed by uncorrected Fisher LSD (**$p<0.0001$, *$p=0.0001$, **$p<0.05$ vs positive control) (FIG. 5D) Quantification of Ki67 positive cells 72 h after wound showing expression of ki67 positive cells for hCEC treated with s-HA and linear HA plus secretome, secretome, s-HA and linear HA alone and complete medium. (FIG. 5E) Heat map showing the different protein expression profiles for c-MSCs treated with s-HA and linear HA and 2D condition.

FIG. 6A-6K shows s-HA hydrogel improves wound healing in in vivo model of corneal epithelial wound healing. (FIG. 6A) Schematic showing s-HA hydrogel application on wounded cornea followed by re-epithelialization. (FIG. 6B) OCT images showing s-HA hydrogel on the surface of cornea after epithelial debridement (FIG. 6C) Central and peripheral cornea stained with DAPI, 72 hours after mechanical injury (scale bars represent 100 μm). Arrows show increased number of cells in the anterior stromal. Inset presents a magnified view of the region underneath the epithelial layer showing the accumulation of cells for the different groups compared to the normal cornea. (FIG. 6D) High magnification image stained with DAPI and phalloidin (green) confirms the infiltrated of neutrofilis cells (arrows) for the mechanical injured groups, 72 hours post injury (scale bars 20 μm). (FIG. 6E) Relative RNA expression of CK12 decreased for the mechanical injured groups while the expression of (FIG. 6F) CK14 increased compared to normal cornea, 72 hours post-injury. (FIG. 6G) Immunostaining confirms the presence of immature epithelial layer stained with CK14 (red, scale bar: 100 μm). (FIG. 6H) All groups were able to form a basement membrane stained with laminin (magenta, scale bar: 100 μm). (FIG. 6I) Quantification of central corneal thickness (n=3) shows increased thickness values for the corneas treated with linear HA and PBS groups compared to normal cornea. Corneas treated with s-HA showed similar corneal thickness compared to normal cornea. (FIG. 6J) Immunostaining images showing the stromal layer stained with CD45 (red) and vimentin (green) for the different groups, 72 hours post-injury (scale bar 50 μm). (FIG. 6K) Images showing the anterior and posterior stromal layer stained with phalloidin (orange) for the corneas treated with s-HA, linear HA, PBS and normal corneas, 72 hours post-injury (scale bar: 20 μm).

Figure 7A:
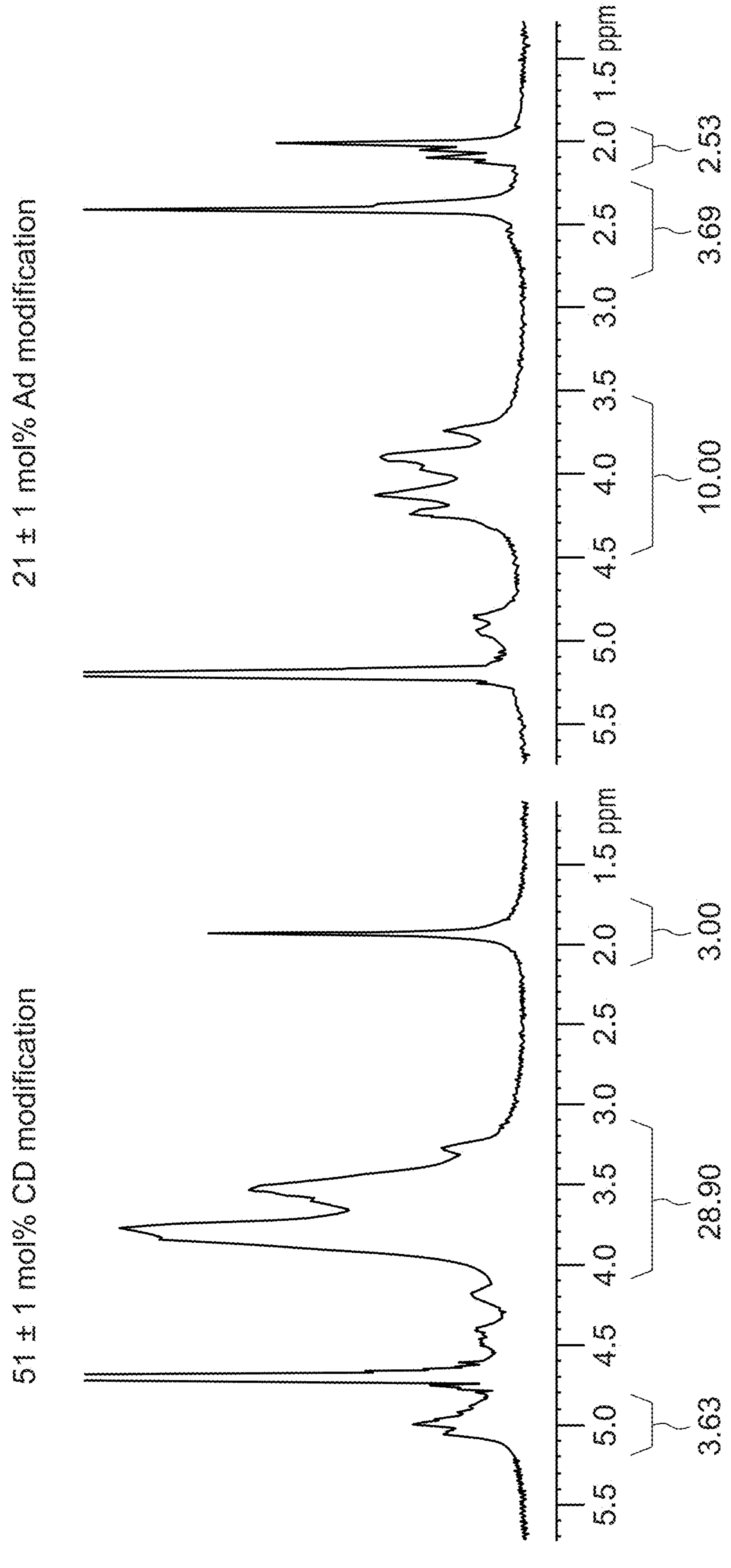
Figure 7B:
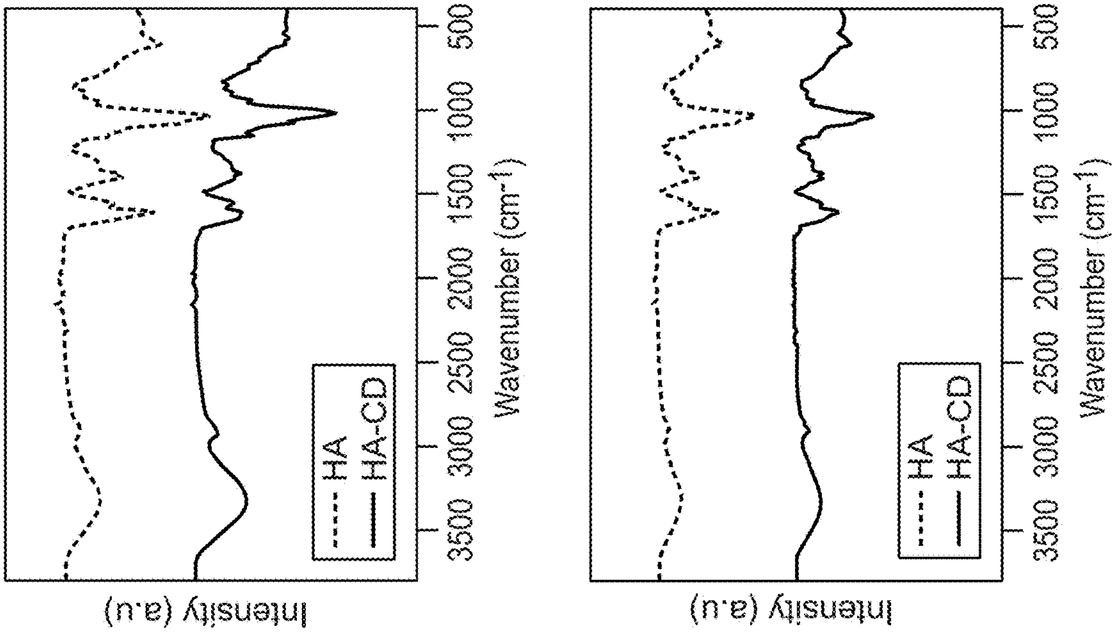
Figure 7C:
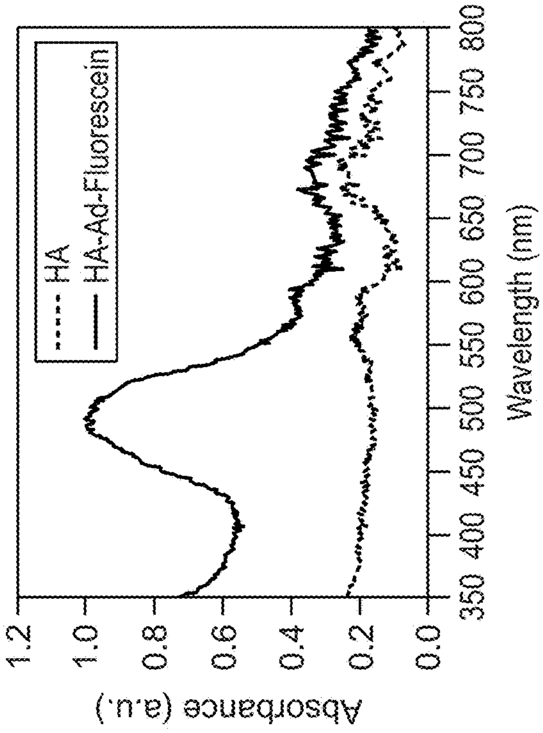

FIGS. 7A-7C shows the characterization of HA macromers. (FIG. 7A) 1H NMR spectrum shows 21±1 mol % Ad modification and 51±1 mol % CD modification on HA backbone. (FIG. 7B) FT-IR spectrum for the analysis of amide and ester linkage formation in HA-CD and HA-Ad. (FIG. 7C) The absorbance of HA-Ad-Fluorescein observed at 496 nm.

Figure 8A:
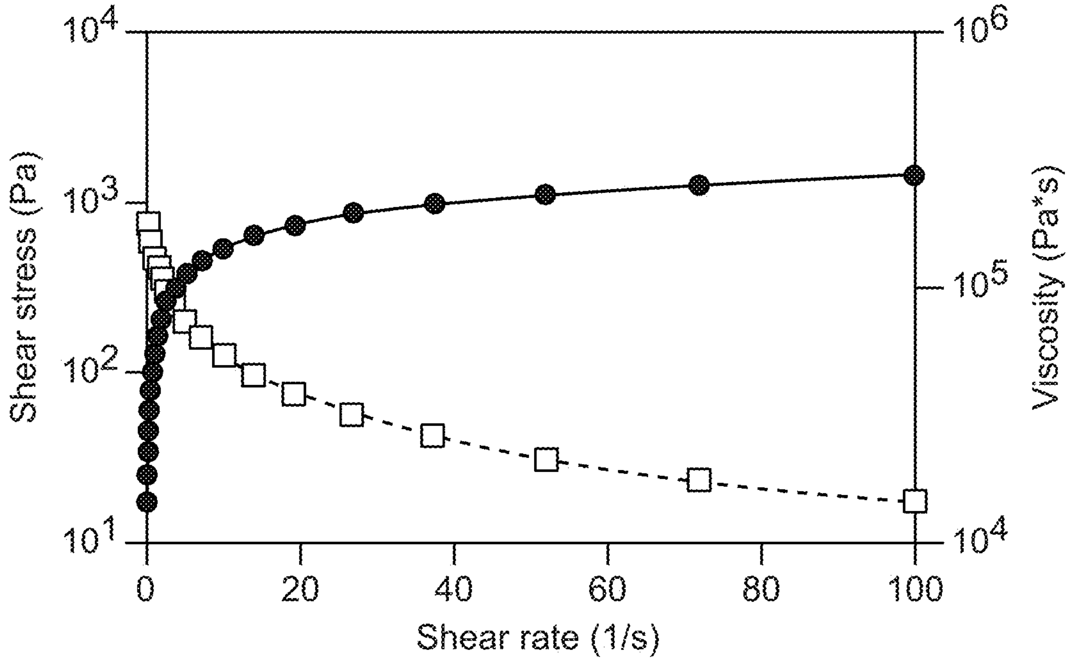
Figure 8B:
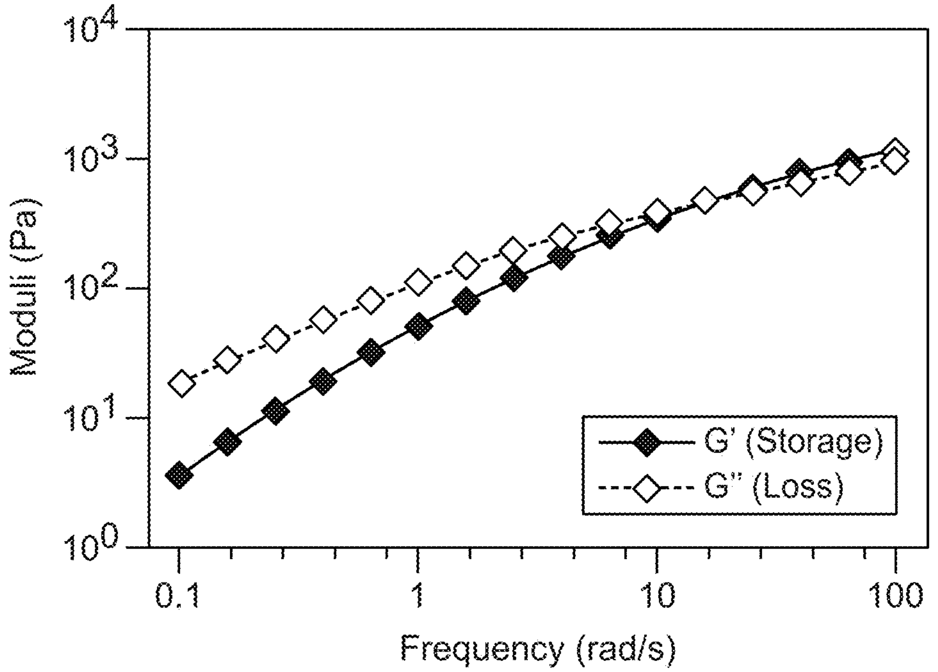
Figure 8C:
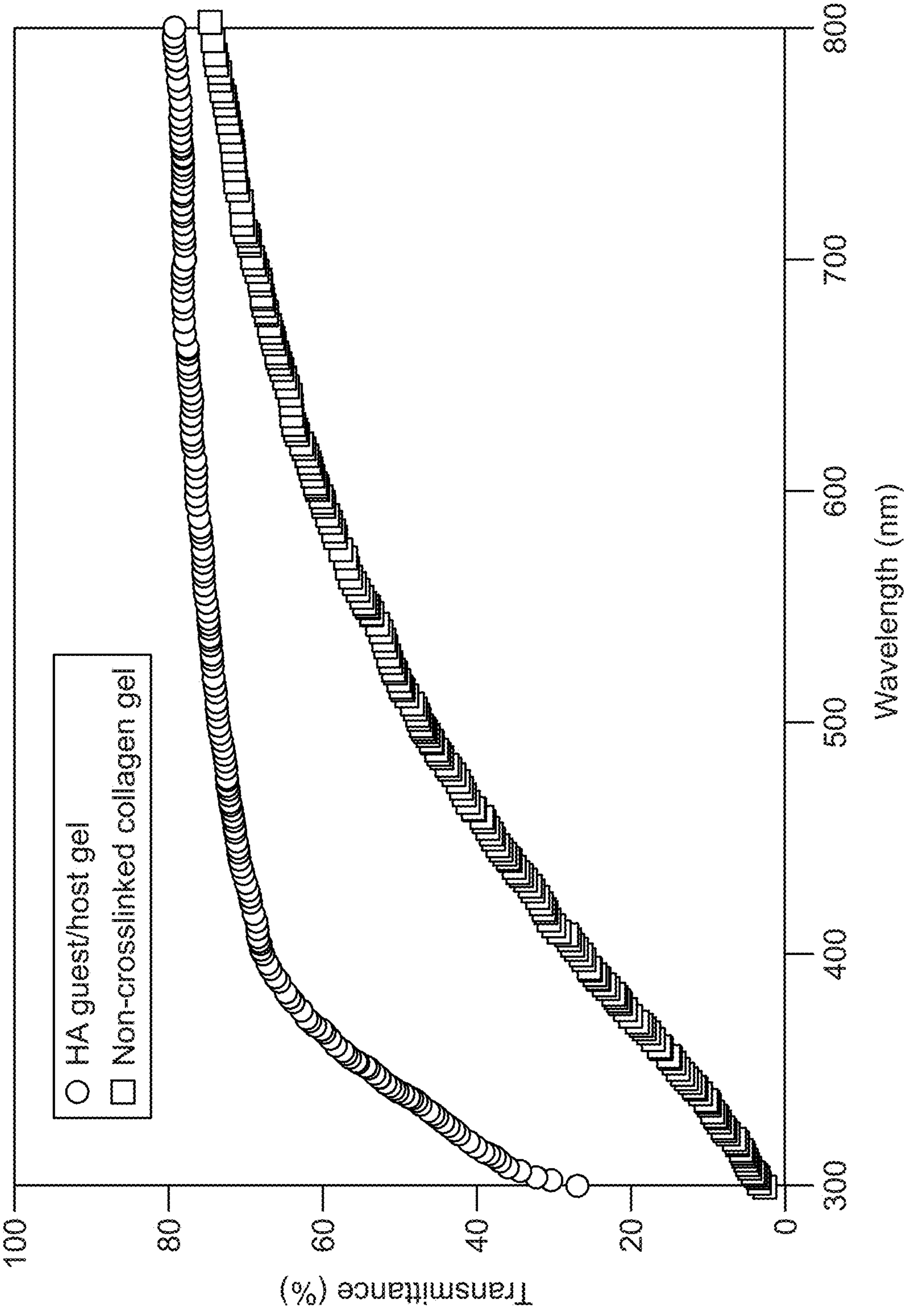

FIG. 8A-8C shows (FIG. 8A) Continuous flow analysis for the gradual decrease of hydrogel viscosity with increasing applied shear stress. (FIG. 8B) Frequency sweep analysis for both storage and loss moduli with increasing applied frequency. (FIG. 8C) The transmittance profile of s-HA vs non crosslinked collagen hydrogels at day 0.

FIG. 9A-9E shows (FIG. 9A) Presence of s-HA hydrogel after encapsulating cornea cells at day 1, 4 and 10 showing that in vitro degradation does not occur in 10 days. PROVISC HA viscoelastic gel is not observed either at day 1, 4 and 10. (FIG. 9B) Quantification of live cells after encapsulation in s-HA at day 0, 4 and 10. (FIG. 9C) Cornea cells after encapsulating in PROVISC HA viscoelastic gel show cells adhered and spread on TCP and the absence of cells within the viscoelastic gel at day 1, 4 and 10. (FIG. 9D) Quantification of corneal cells on the TCP after encapsulating in s-HA hydrogel at day 1, 4 and 10. Cell proliferation significantly changed at day 10 for C-MSC****p<0.0001 vs. CEC day 10; data is presented as mean±SD, Two-way ANOVA (p<0.005) was used to detect statistical differences followed by Sidak's multiple comparisons test.

Figure 9A:
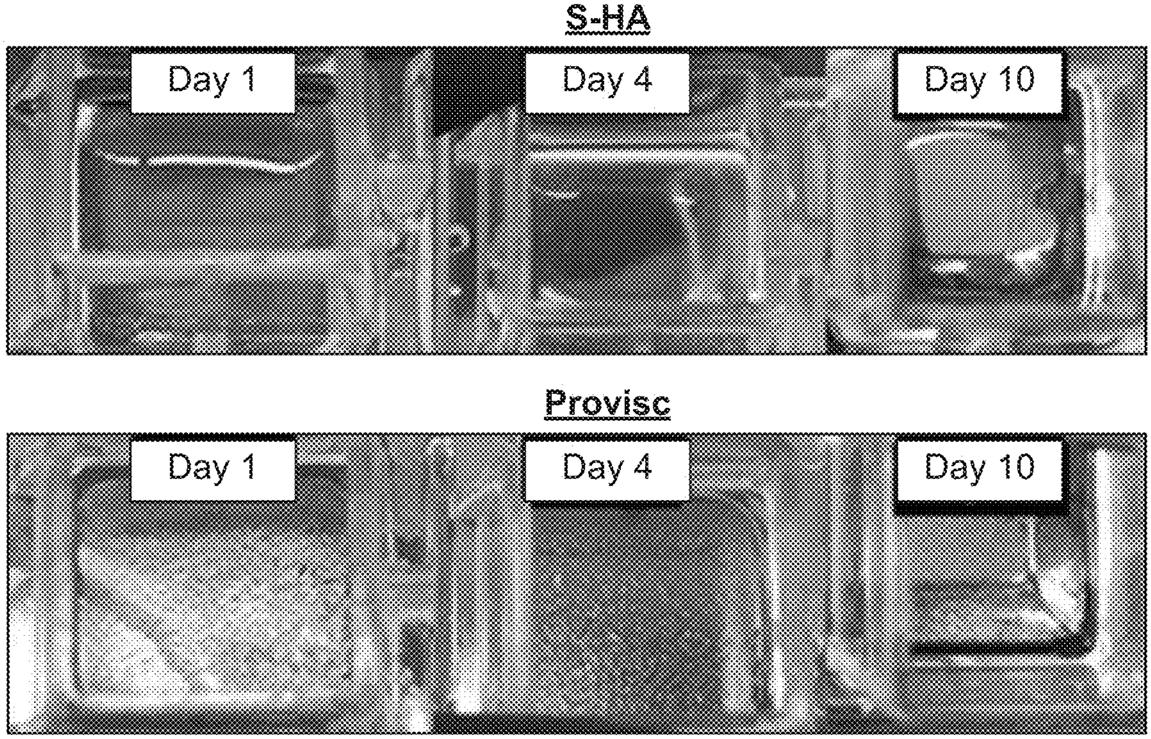
Figure 9B:
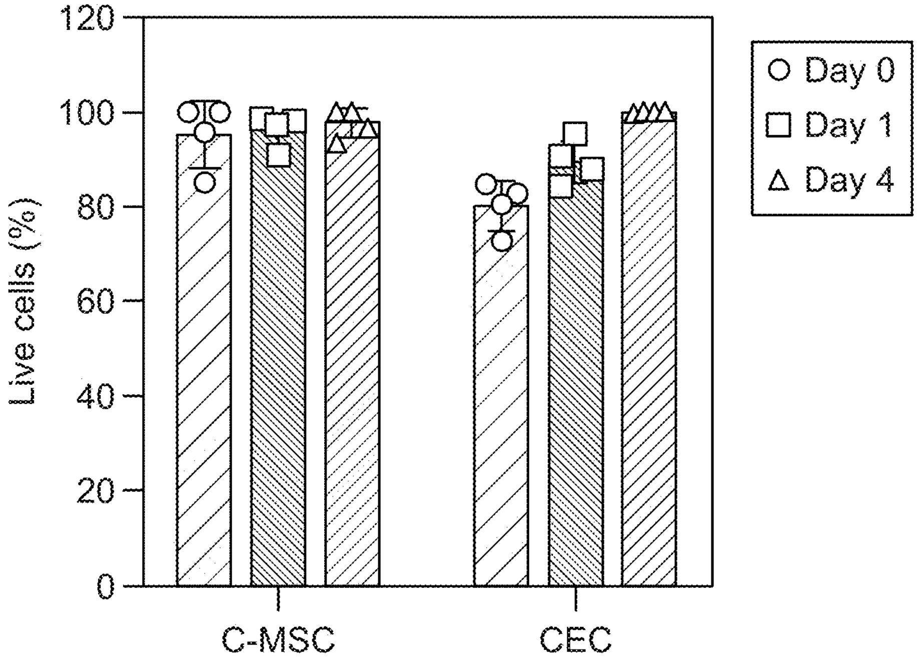
Figure 9C:
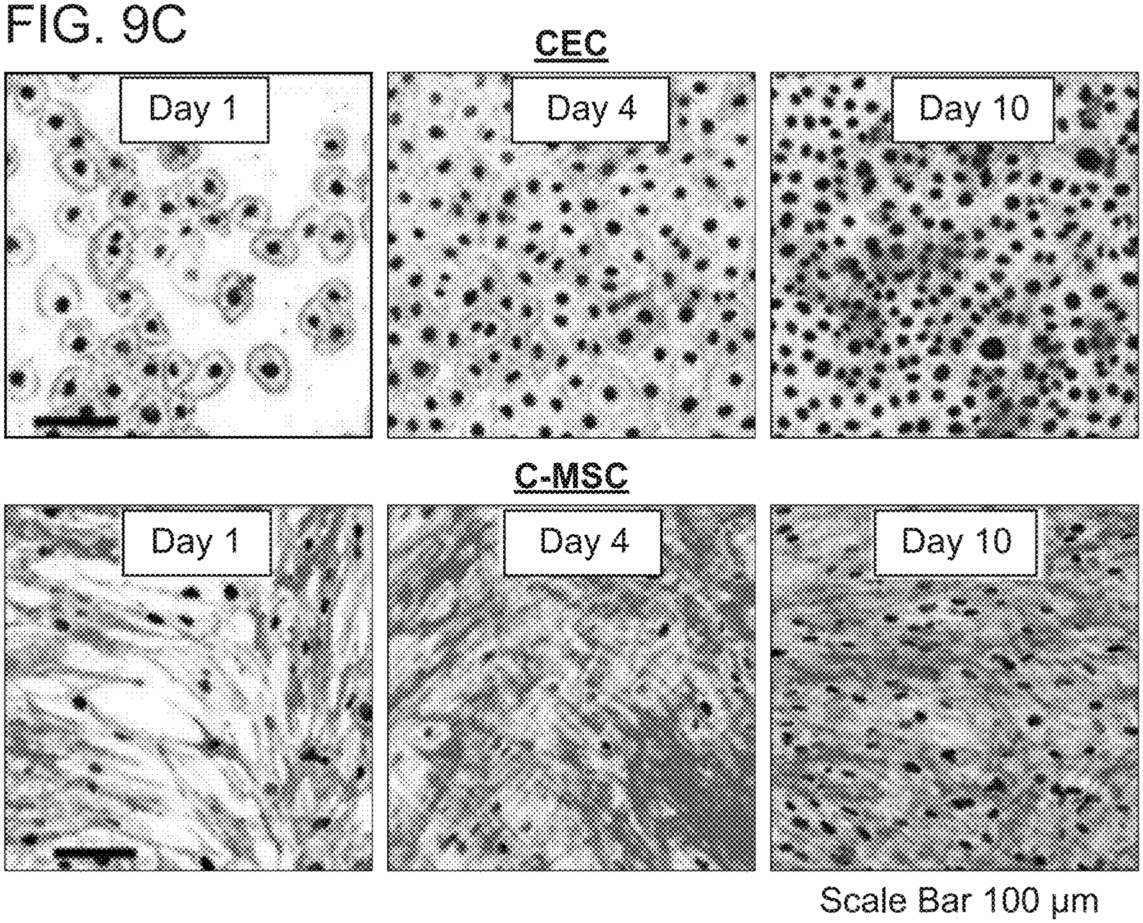
Figure 9D:
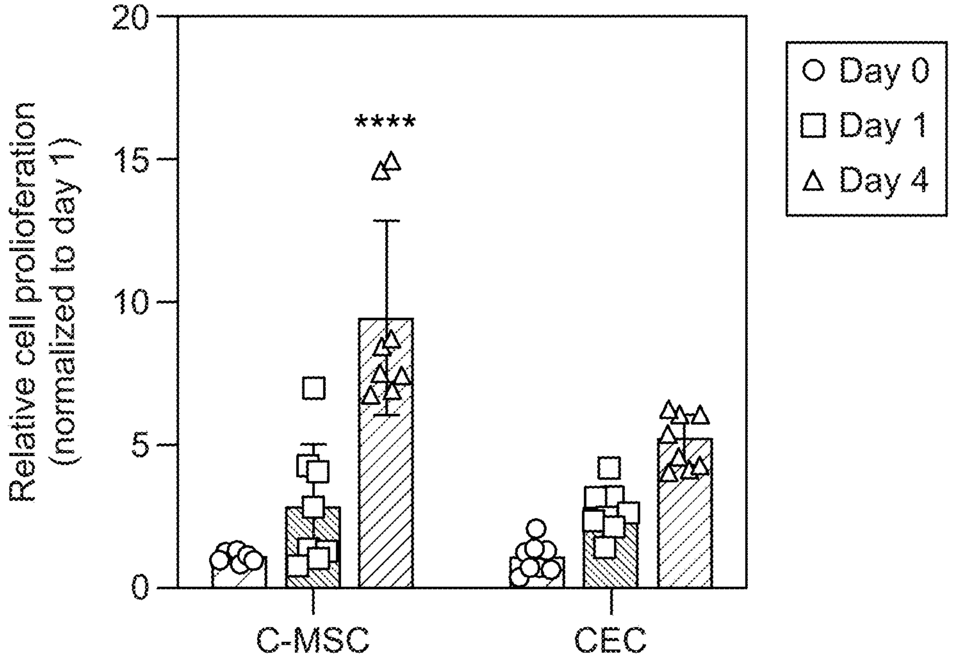
Figure 9E:
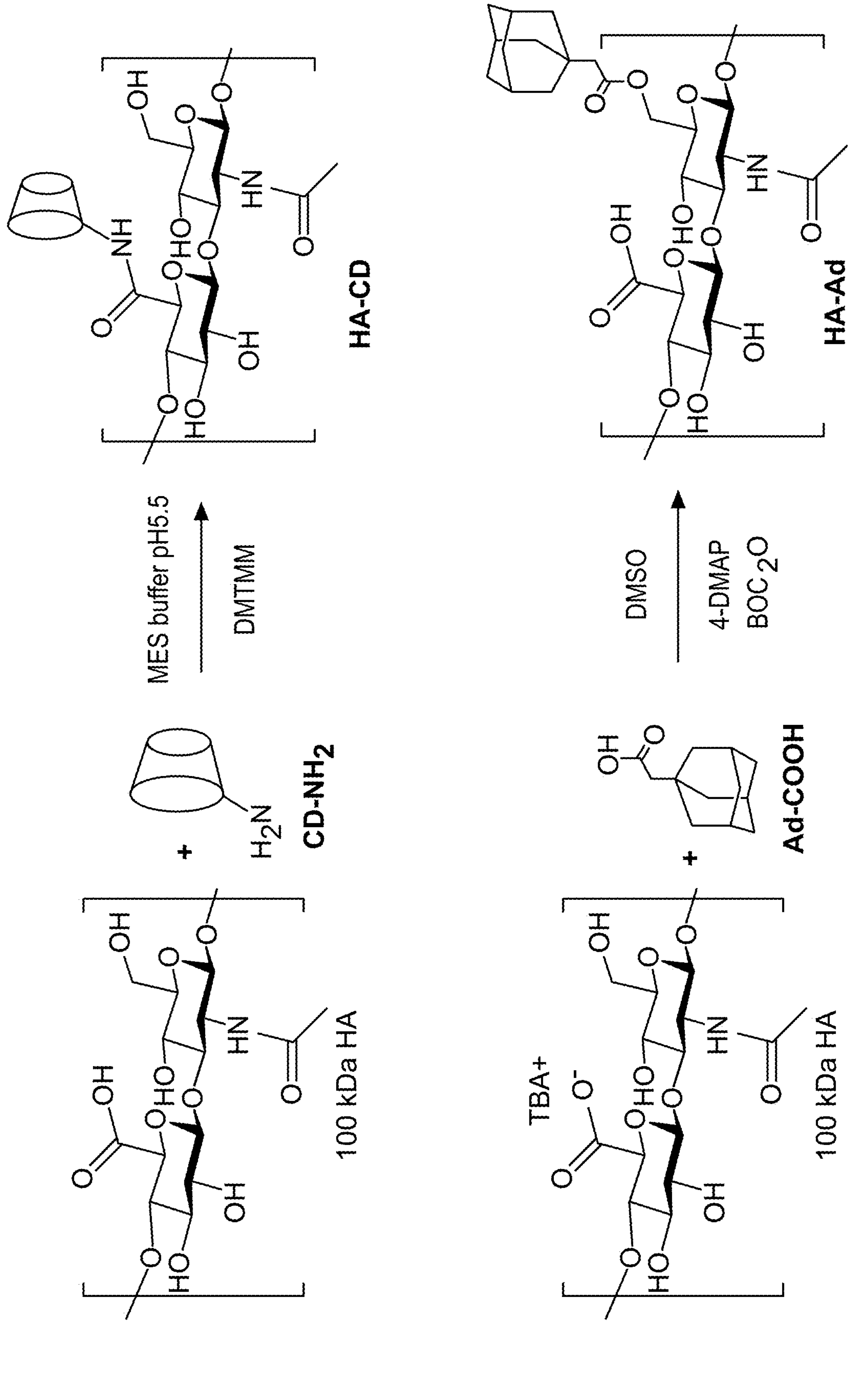
Figure 9E:
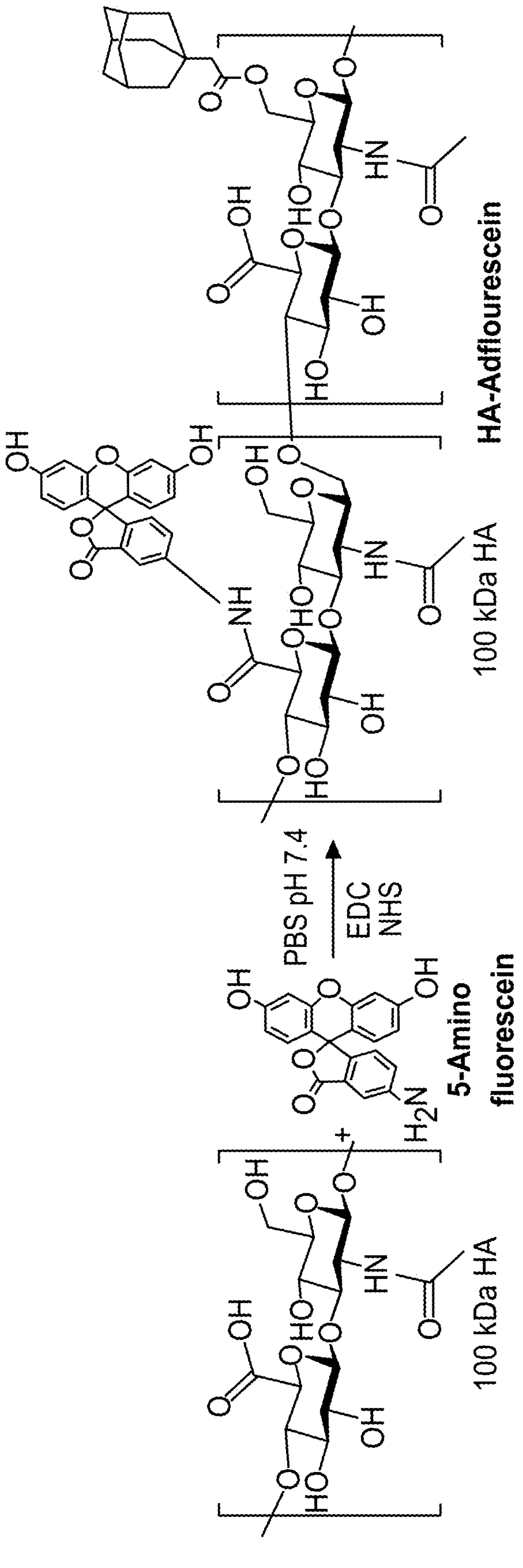

FIG. 9E shows a schematic illustration for the synthesis of HA-CD, HA-Ad, and HA-Ad-fluorescein macromers.

Figure 10A:
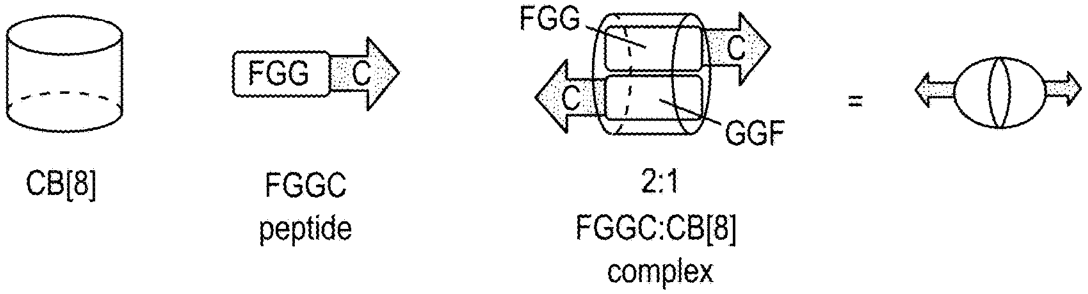
Figure 10B:
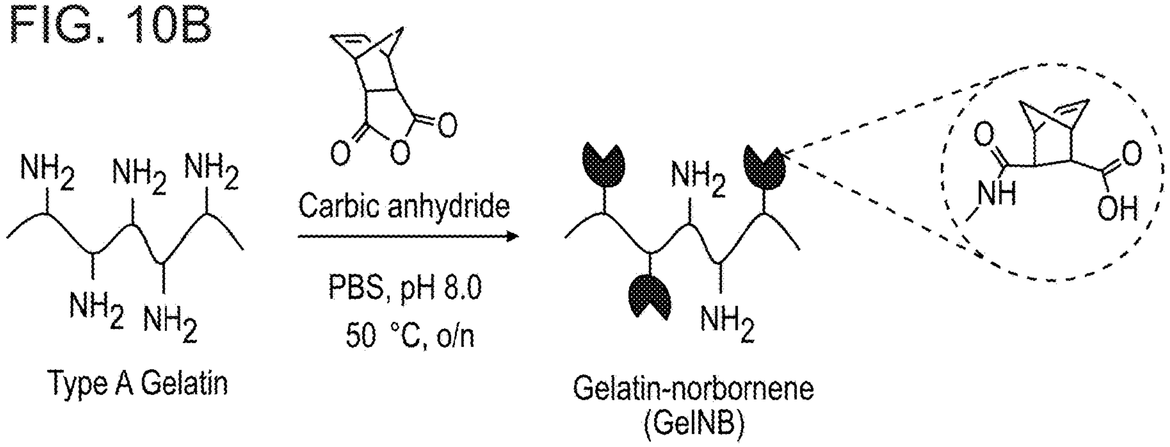
Figure 10C:
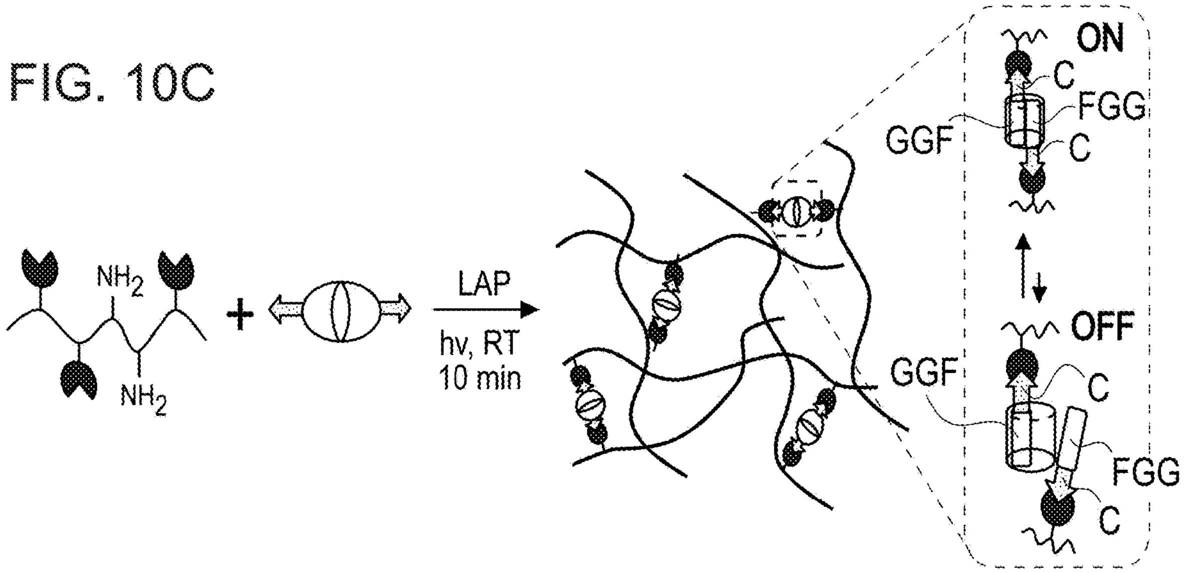

FIG. 10A-10C. Idealized schematic of rapid, user-triggered crosslinking of CB[8]-based gelatin hydrogels under cell-compatible conditions. (FIG. 10A) 2:1 FGGC peptide: CB[8] homoternary complexes are formed by simultaneous inclusion of two FGGC peptides in one CB[8] cavitand, increasing the solubility of CB[8] in physiological medium. (FIG. 10B) Gelatin-norbornene (GelNB) is prepared by reacting carbic anhydride with primary amines in gelatin, where primary amines act as nucleophiles and attack a carbonyl carbon on the carbic anhydride, yielding an amide-linked norbornene. (FIG. 10C) Supramolecular gelatin hydrogels are formed via user-triggered thiol-ene reactions between grafted norbornenes and preassembled CB[8] .FGGC peptide ternary complexes.

Figure 11A:
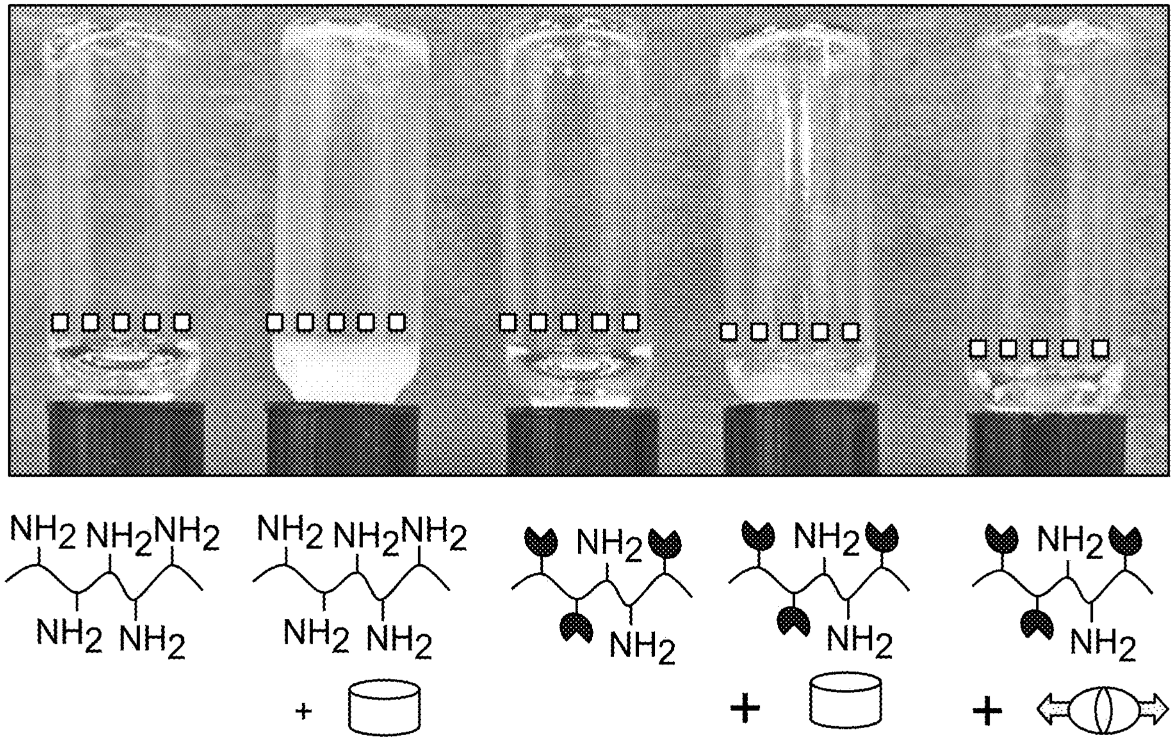
Figure 11B:
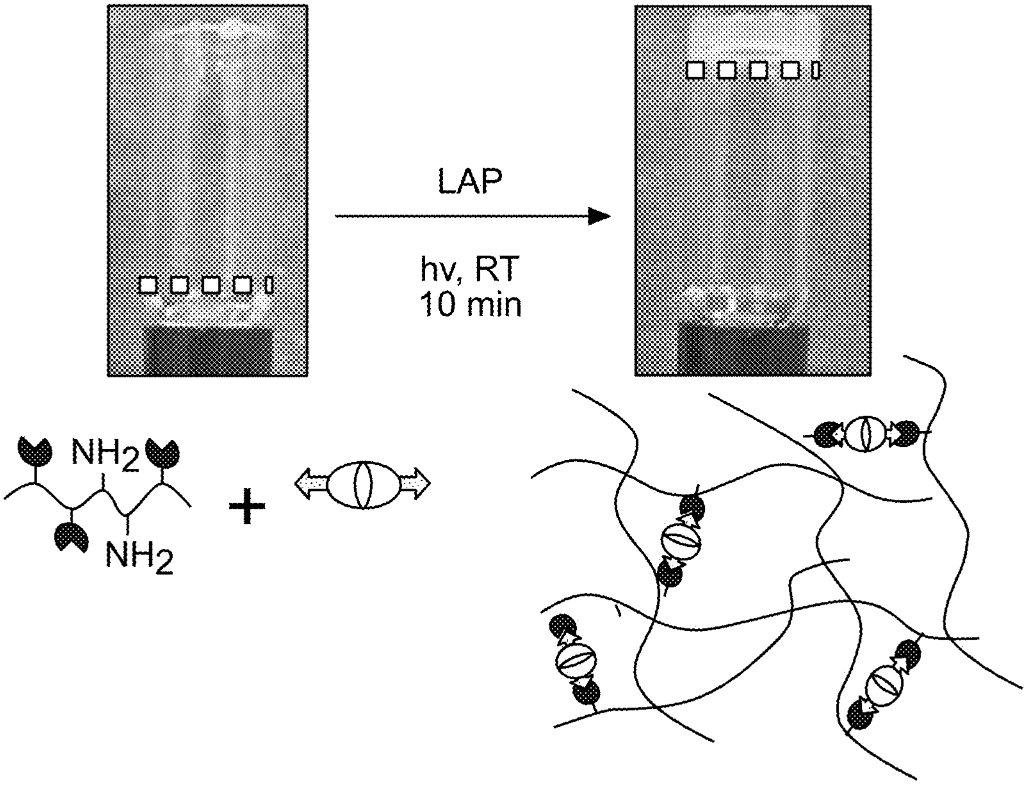
Figure 11C:
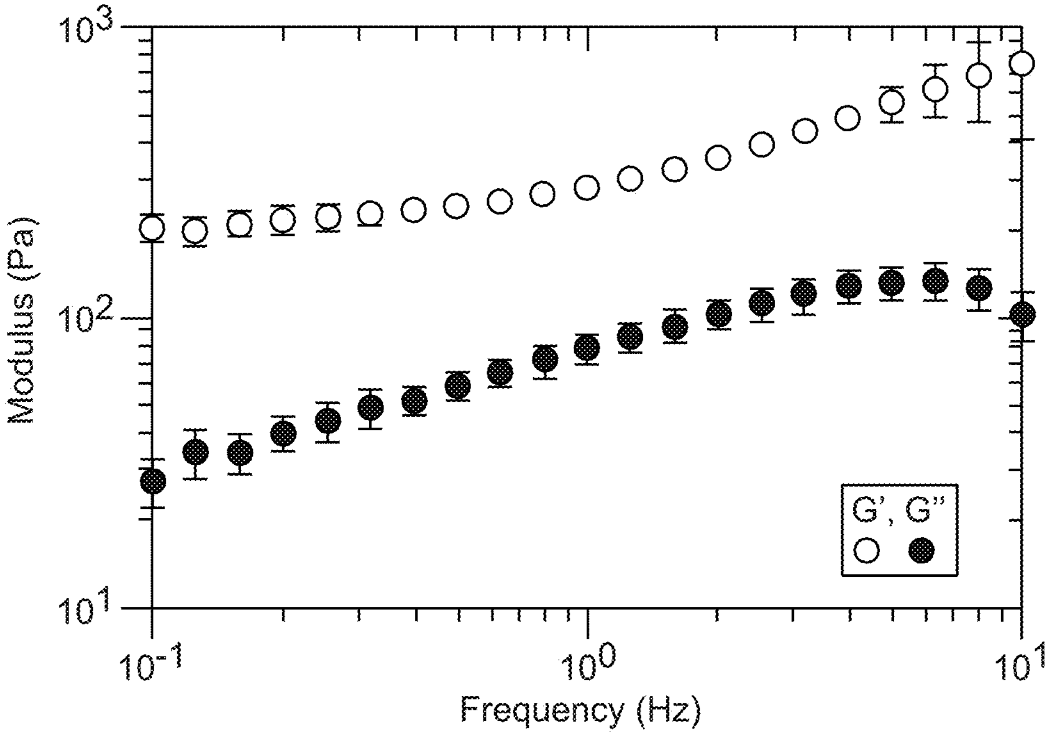
Figure 11D:
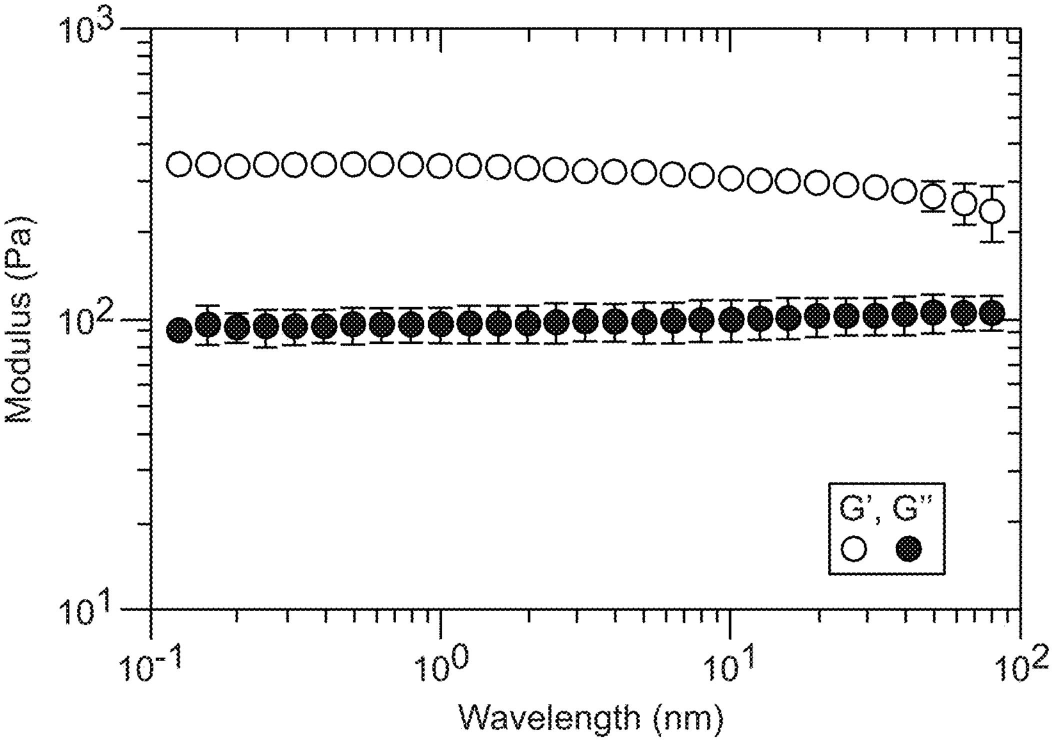
Figure 11E:
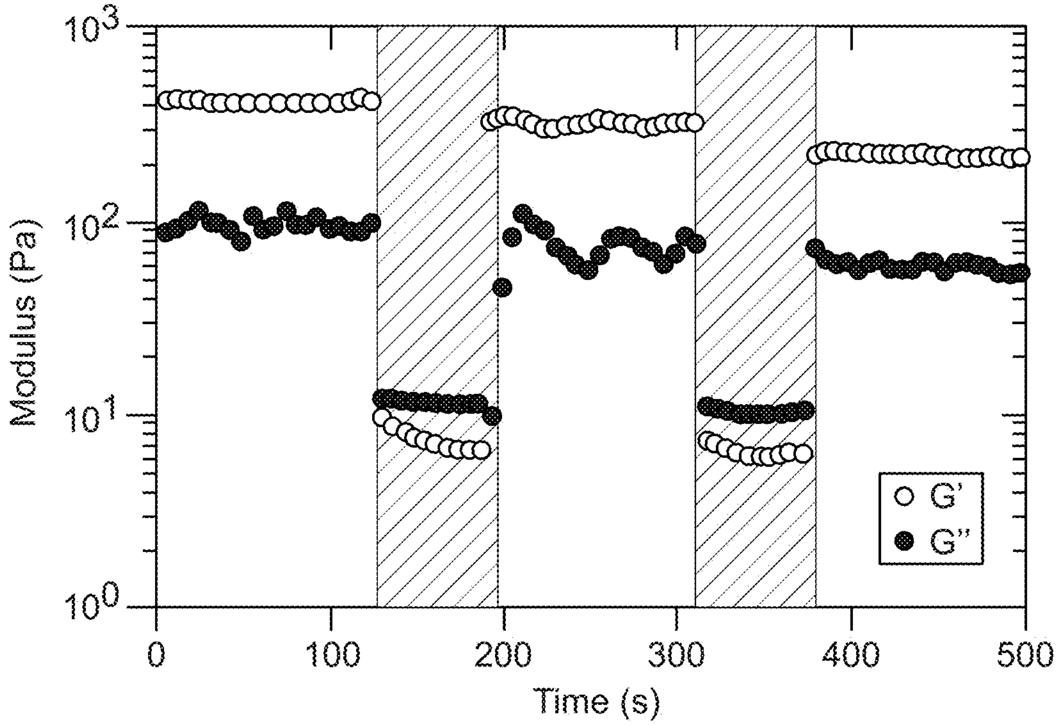
Figure 11F:
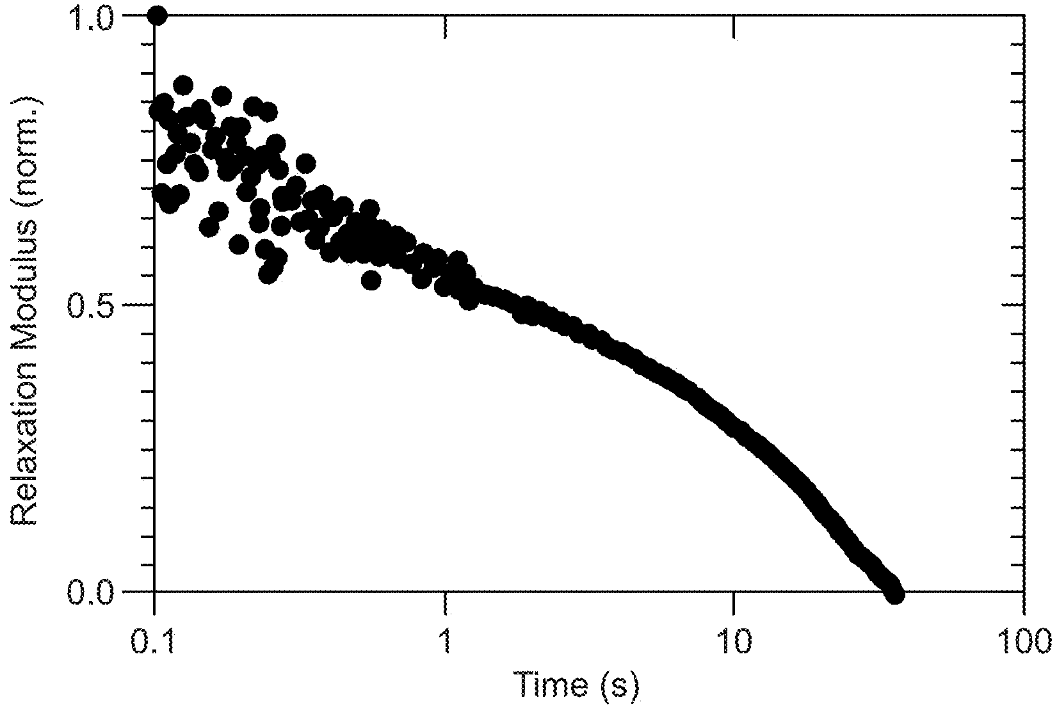

FIG. 11A-11F CB[8]-based supramolecular gelatin hydrogels are stable, shear-thinning, and self-healing at physiological temperature. (FIG. 11A) Images of gelatin, gelatin mixed with CB[8], gelNB, gelNB mixed with CB[8], and gelNB mixed with preassembled CB[8].FGGC peptide ternary complexes at 37° C. Inverted vials demonstrate that none of these systems form temperature stable hydrogels in the absence of a further stimulus. (FIG. 11B) Temperature stable CB[8]-based supramolecular gelatin hydrogels form following addition of a photoinitiator and 10 minutes of exposure to 365 nm light. These hydrogels exhibit frequency-dependent (data presented as mean±SD, n=3) (FIG. 11C) and strain-dependent (w=10 rad/s, data presented as mean±SD, n=3) (FIG. 11D) mechanical properties in oscillatory shear rheology at 37° C. Additionally, CB[8]-based supramolecular gelatin hydrogels are capable of shear-thinning and self-healing over multiple rounds of strain cycling (sequential shear with 0.1% strain for 120 s (white region) followed by 1000% strain for 60 s (purple region); w=10 rad/s; data presented as mean, n=3) (FIG. 11E) and rapidly dissipating stress under a 2% strain at 37 ° C. (FIG. 11F).

Figure 12A:
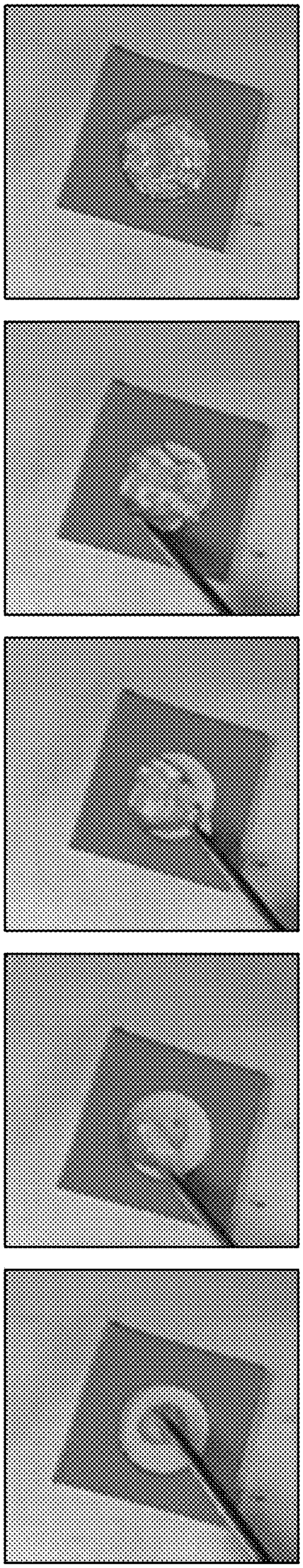
Figure 12B:
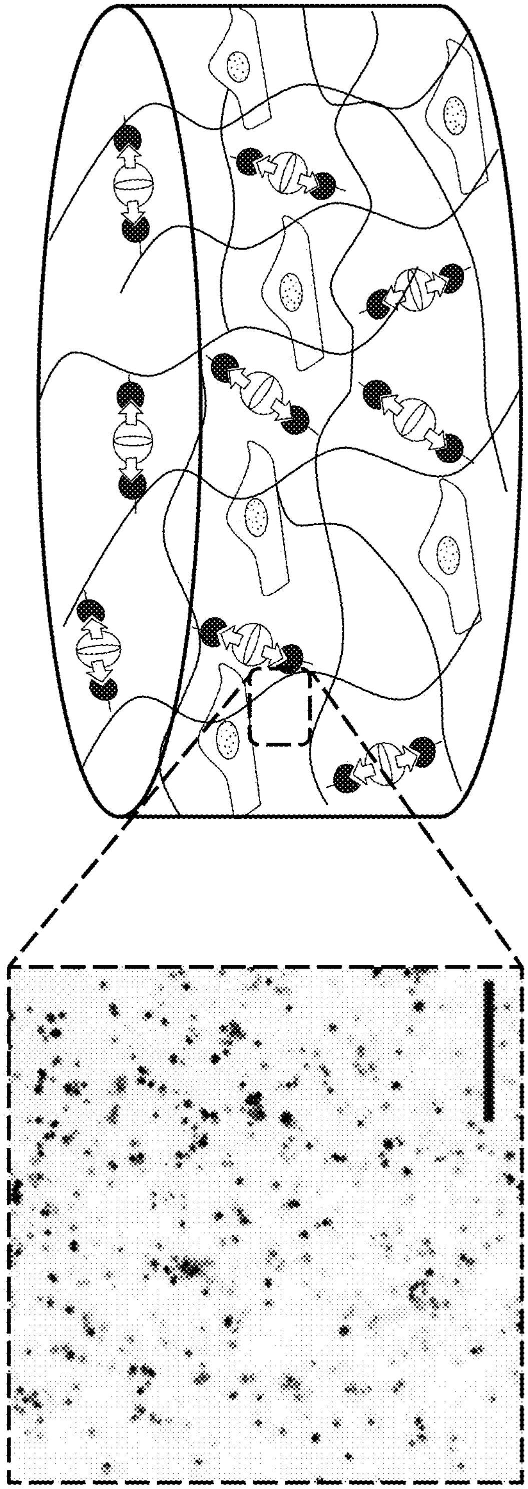

FIG. 12A-12B. (FIG. 12A) Pre-formed CB[8]-based supramolecular gelatin hydrogels can be injected through an 18G syringe needle and rapidly reform at 37 ° C. (FIG. 12B) Cells encapsulated in pre-formed gels are highly viable post-injection. Viability data are mean±SD, determined using 4 hydrogel replicates (3 z-stacks per replicate), 24 h post-injection.

Figure 13A:
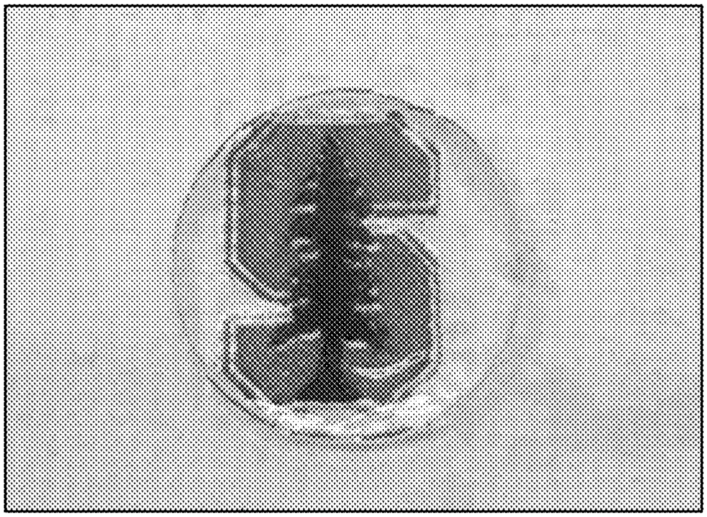
Figure 13B:
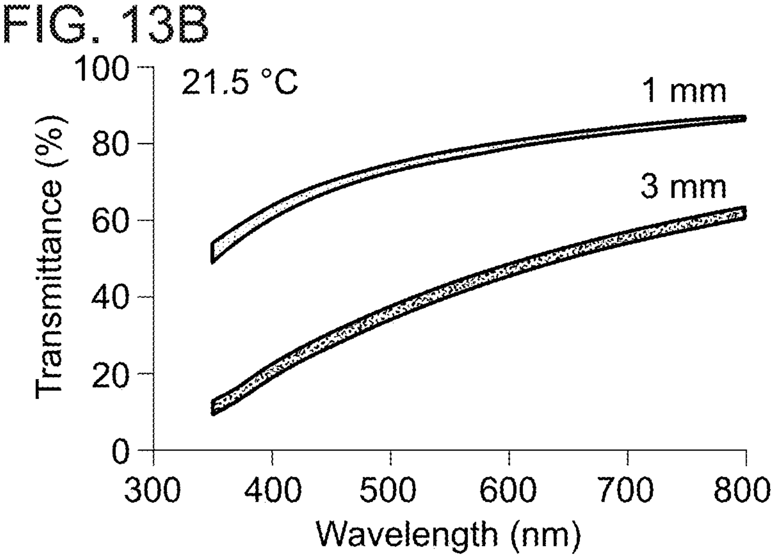
Figure 13C:
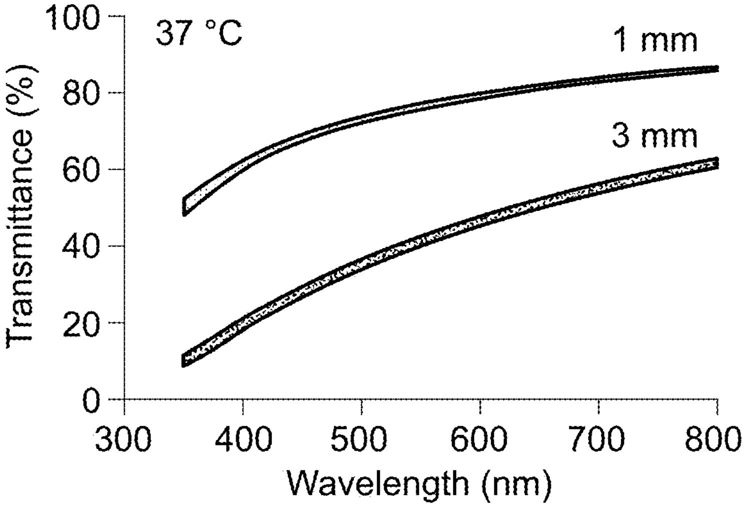

FIG. 13A-13F. CB[8]-based supramolecular gelatin hydrogels permit light-based observation of the morphology and behavior of encapsulated MRC-5s over seven days in culture. (FIG. 13A) Photograph of a 0.5-mm thick freestanding hydrogel under ambient conditions. Transmittance spectra of supramolecular gelatin hydrogels (1-mm thick (predicted), 3-mm thick (actual)) from 350 to 800 nm at ambient temperature (FIG. 13B) and 37 ° C. (FIG. 13C). Data are presented as error envelopes (mean±SD, n=3). Confocal 3D reconstructions of encapsulated, viable human fibroblasts, stained by calcein AM, in CB[8]-based supramolecular gelatin hydrogels after (FIG. 13D) 2 h, (FIG. 13E) 2 days, and (FIG. 13F) 7 days.

FIG. 14A-14F. Supramolecular CB[8]-based gelatin hydrogels support the culture of MRC-5 human lung fibroblasts for seven days in culture. Viability of MRC-5s encapsulated in the hydrogels after (FIG. 14A) 2 h, (FIG. 14B) 2 days, and (FIG.14C) 7 days, as measured by a Live/Dead cytotoxicity assay. Viability data are mean±SD, determined using 9 z-stacks (2-3 independent hydrogel replicates per condition). Confocal fluorescence micrographs showing spreading of MRC-5s cultured in CB[8]-based supramolecular gelatin hydrogels for (FIG. 14D) 2 h, (FIG. 14E) 2 days, and (FIG. 14F) 7 days. The actin cytoskeleton was visualized using a blue fluorescent protein (BFP) reporter (Life-Act-mTagBFP2).

Figures 15A, 15B:
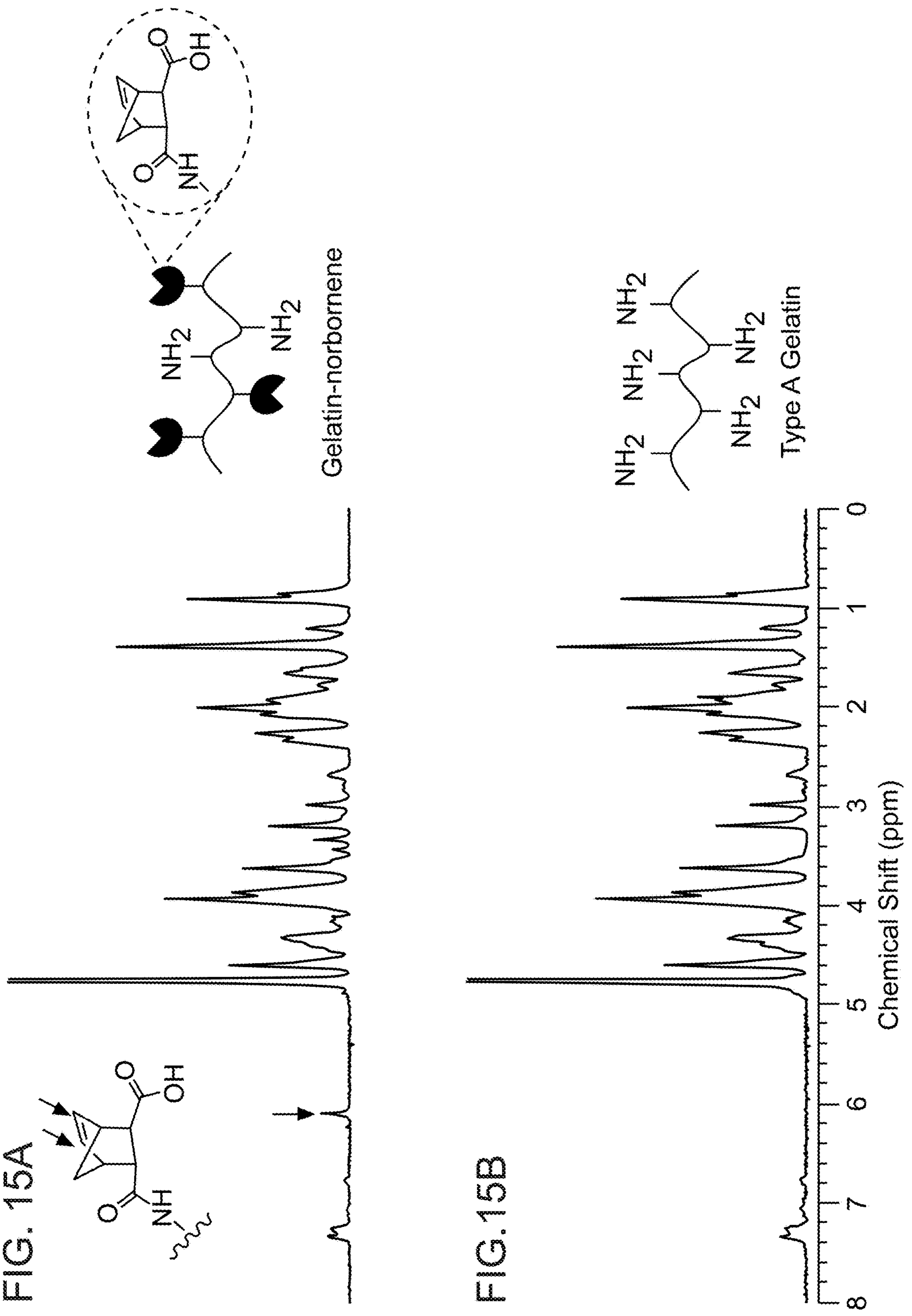

FIG. 15A-15B. $^{1}$H-NMR (500 MHz, $D_2O$) for (FIG. 15A) gelatin-norbornene and (FIG. 15B) unmodified type A gelatin.

Figure 16:
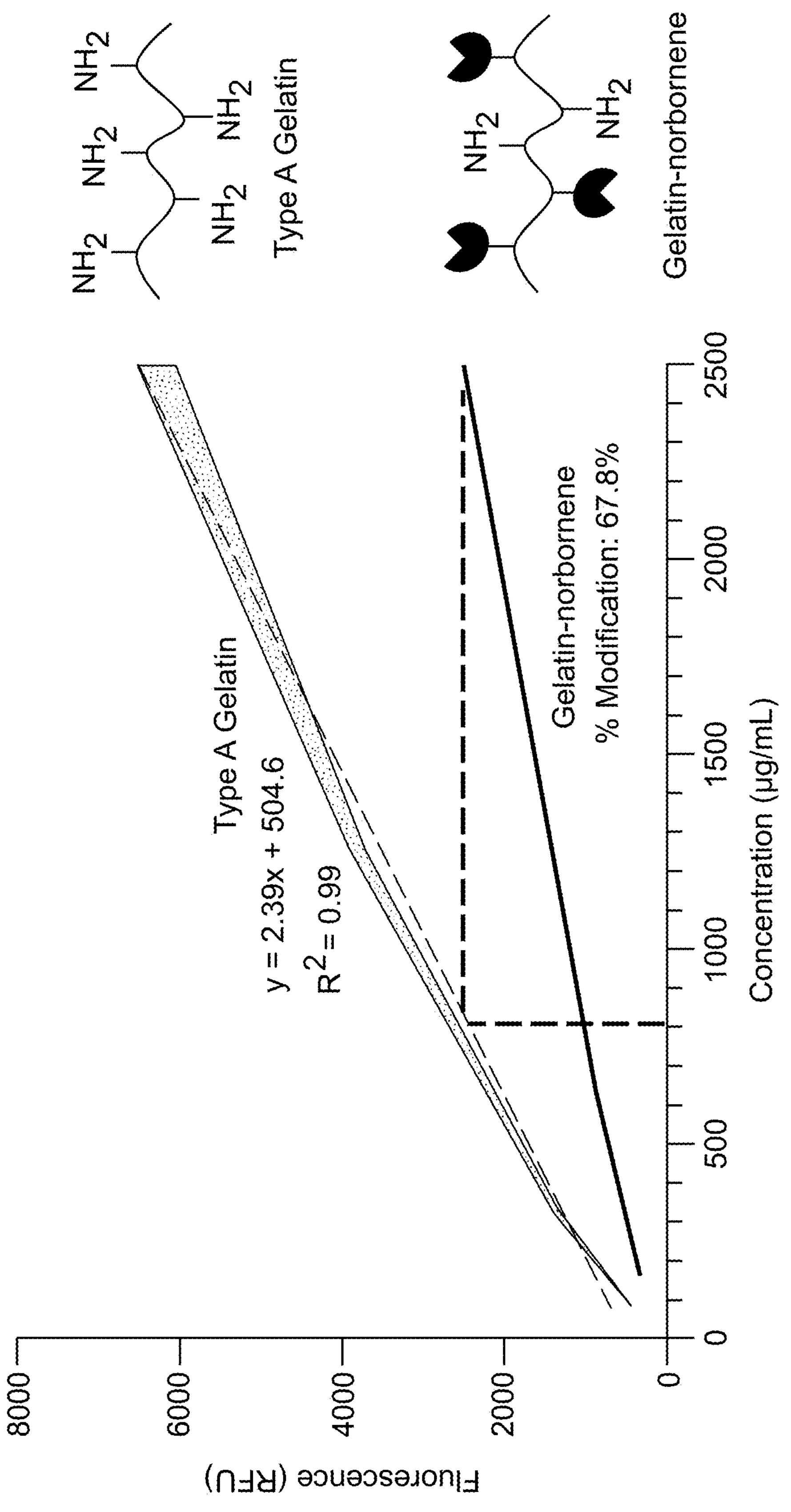

FIG. 16. Conversion of gelatin's free amines to amide-linked norbornene was estimated using a fluorescamine-based assay.

Figure 17A:
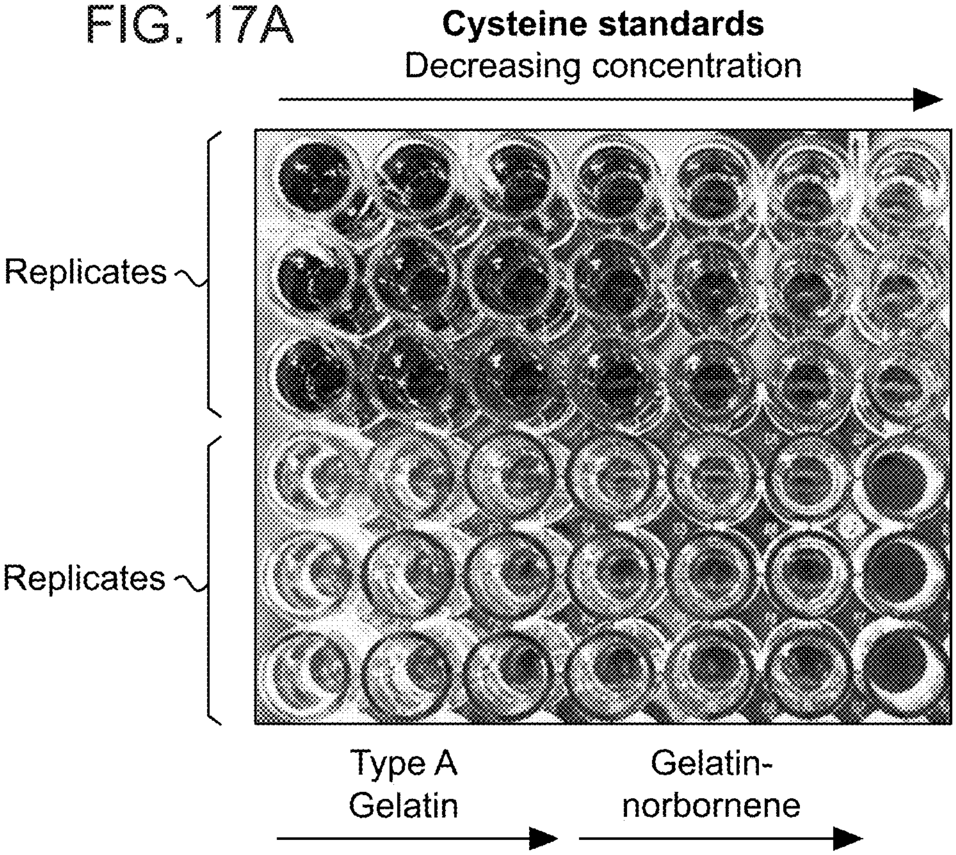
Figure 17B:
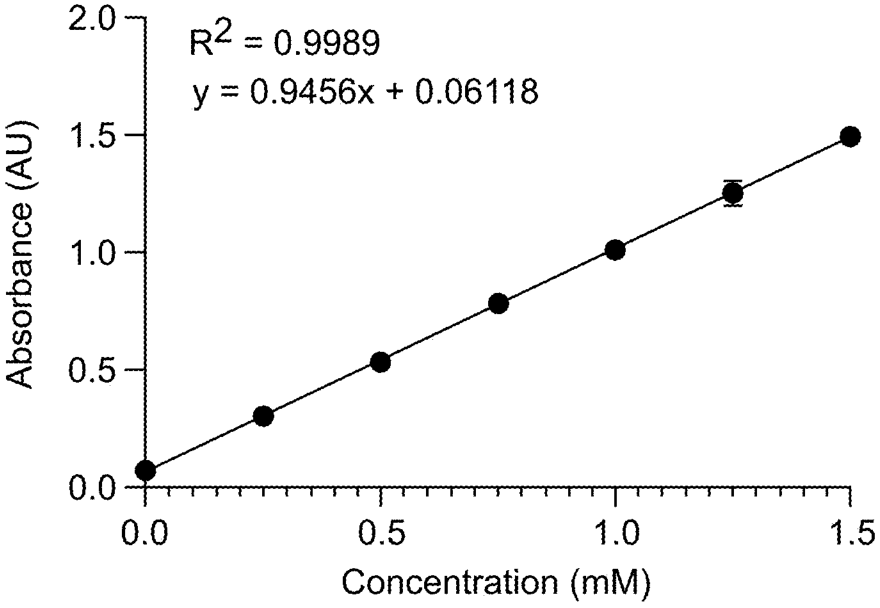

FIG. 17A-17B. The free thiol content of unmodified type A gelatin from porcine skin (Sigma G1890) and gelatin-norbornene was measured using Ellman's assay, in which 5,5'-dithio-bis-(2-nitrobenzoic acid) reacts with a free sulfhydryl group to yield a colored species 2-nitro-5-thiobenzoic acid. (FIG. 17A) 96-well plate with seven cysteine standard controls (top three rows from left to right: 1.5 mM, 1.25 mM, 1.0 mM, 0.75 mM, 0.5 mM, 0.25 mM, and 0 mM) and three dilutions of type A gelatin and gelatin-norbornene (bottom three rows: 40 mg/mL, 20 mg/mL, and 10 mg/mL) after 15 minute incubation with Ellman's reagent. (FIG. 17B) Standard curve generated from cysteine controls, showing a linear correlation with cysteine concentration.

FIG. 18A-18D. Rheological characterization of hydrogel mechanical properties. Frequency and strain sweeps of CB[8]-based supramolecular gelatin hydrogels prepared using different weight percentages of gelatin-norbornene (6% w/v (A, B), 8% w/v (C,D)) with 50% theoretical modification of gelatin free amines with supramolecular crosslinks exhibit frequency-dependent, strain-independent, and predominantly elastic (G'>>G") mechanical properties for both formulations. Mean data are presented, n=3-4.

Figure 19A:
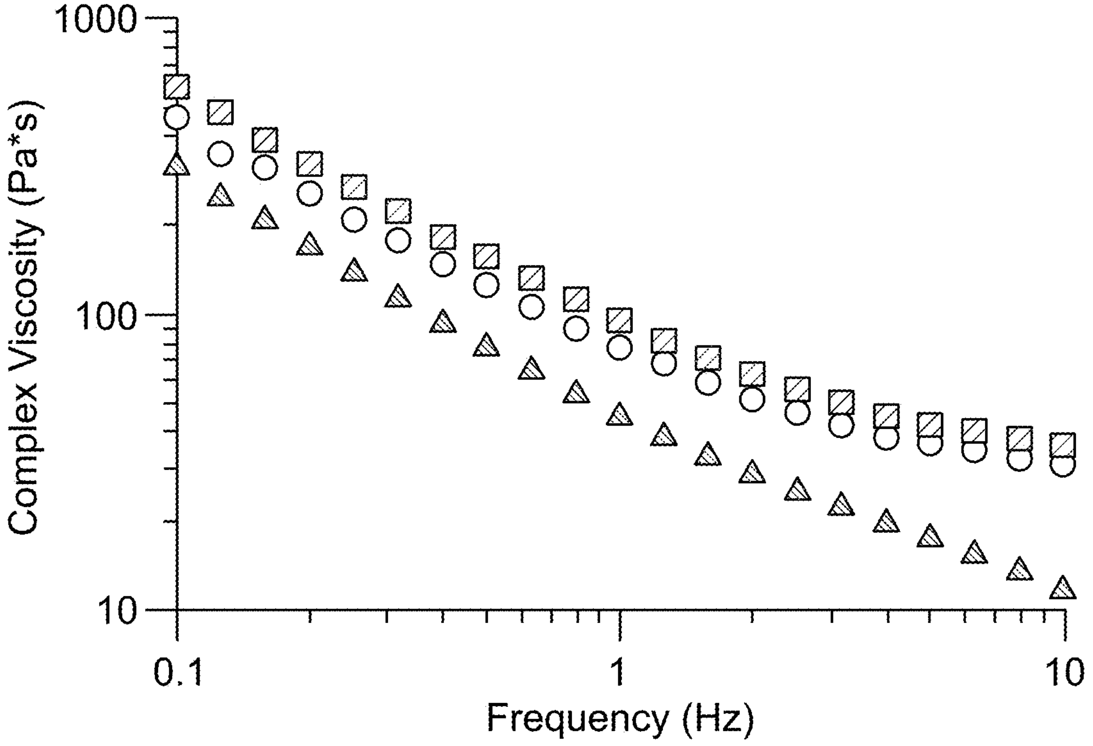
Figure 19B:
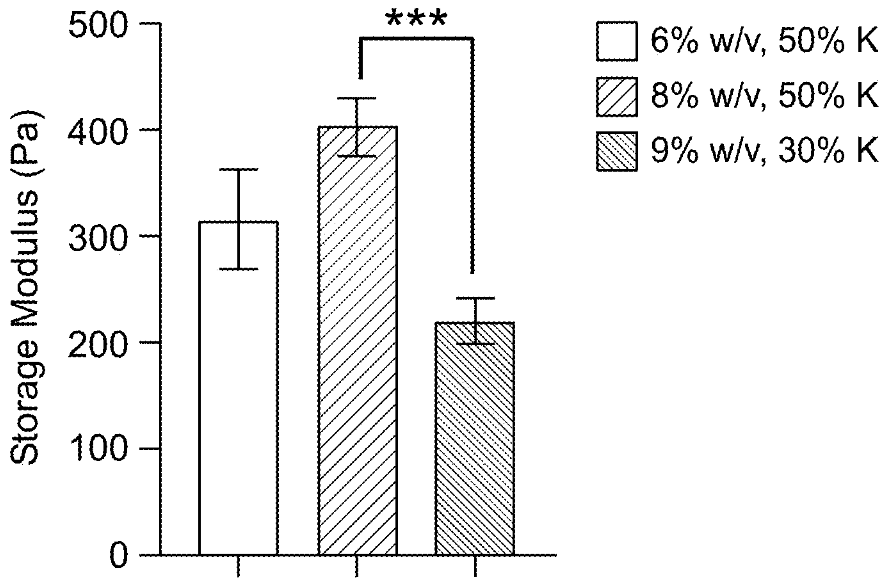

FIG. 19A-19B. Hydrogel frequency-dependent complex viscosity (FIG. 19A) and stiffness (FIG. 19B) can be tuned by altering the weight percentage of gelatin-norbornene and/or the theoretical degree of modification of gelatin free amines with supramolecular crosslinks. Data are presented as mean±SD, n=3-4, ***=p<0.0005, unpaired two-tailed t-test with Welch's correction.

Figure 20A:
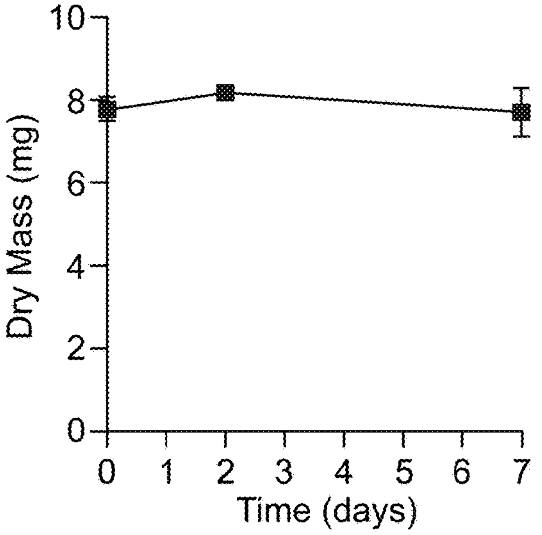
Figure 20B:
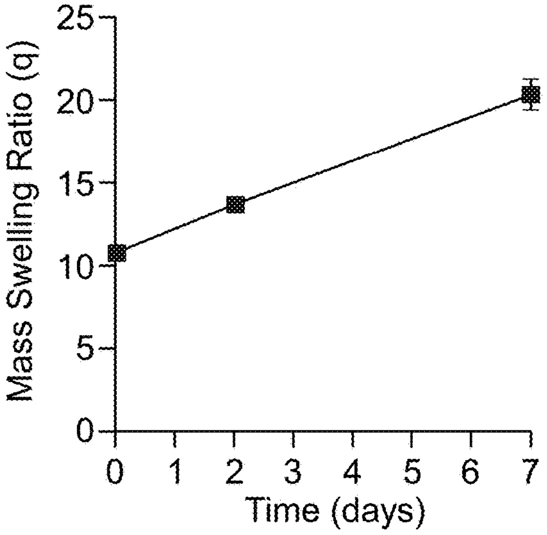

FIG. 20A-20B. CB[8]-based supramolecular gelatin hydrogels swell but do not degrade over 7 days at 37° C. in serum-containing cell culture media. (A) Dry mass and (B) mass swelling ratio of 9% w/v gelatin-norbornene hydrogels with 30% theoretical modification of gelatin free amines with supramolecular crosslinks. Data are mean±SD, n=4 gels per time point.

Figure 21A:
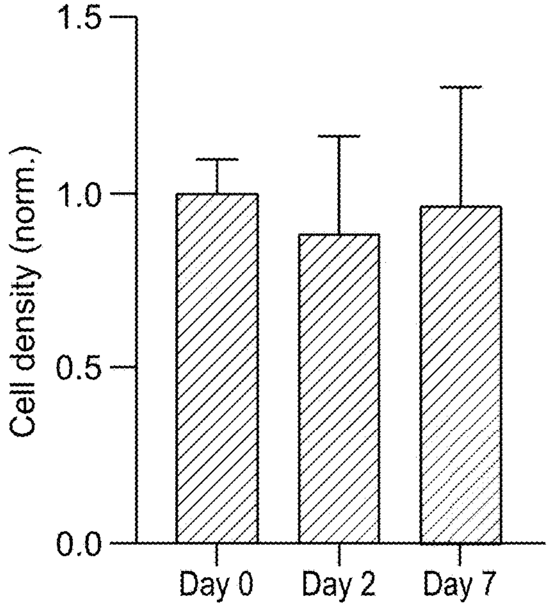
Figure 21B:
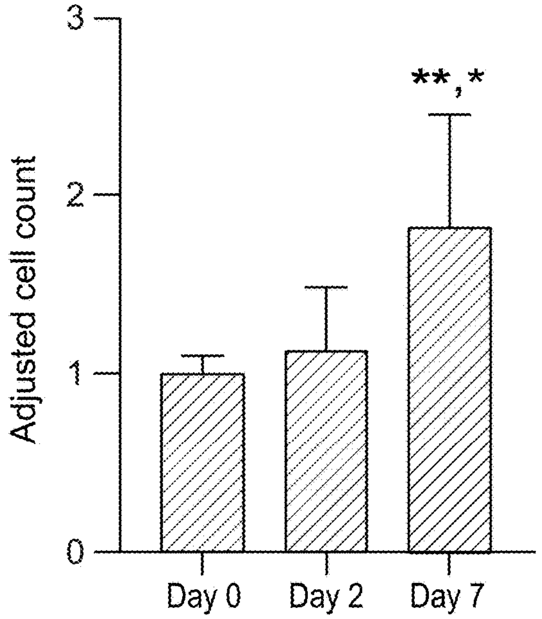
Figure 22A:
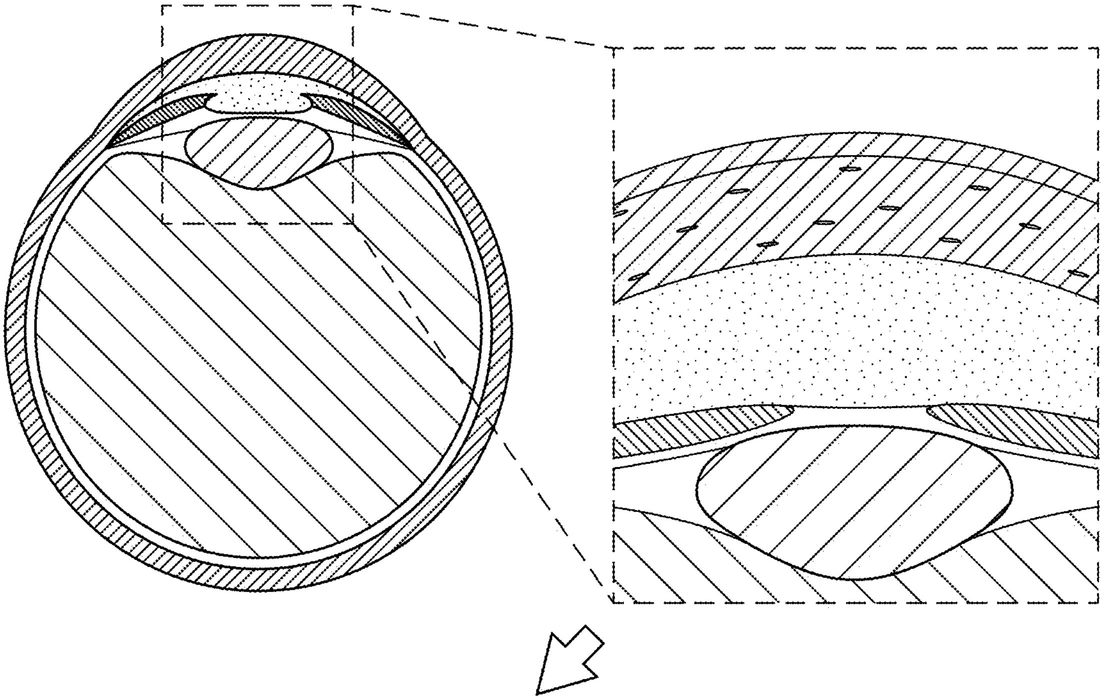
Figure 22B:
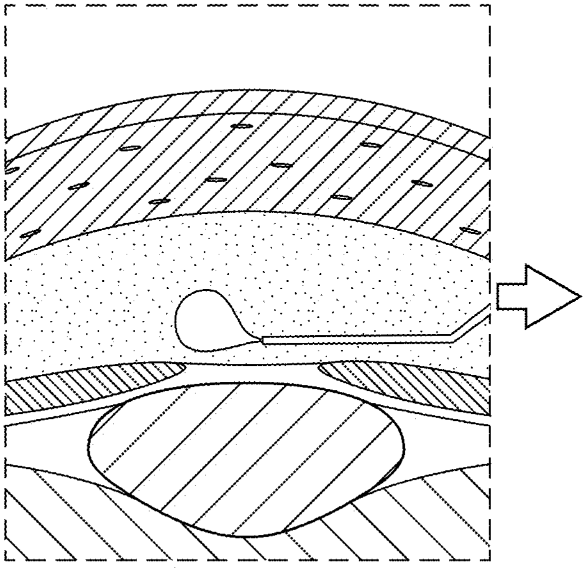
Figure 22C:
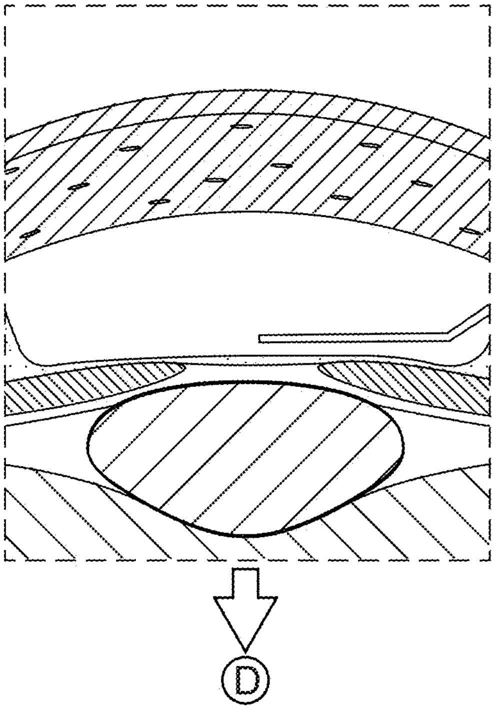
Figure 22D:
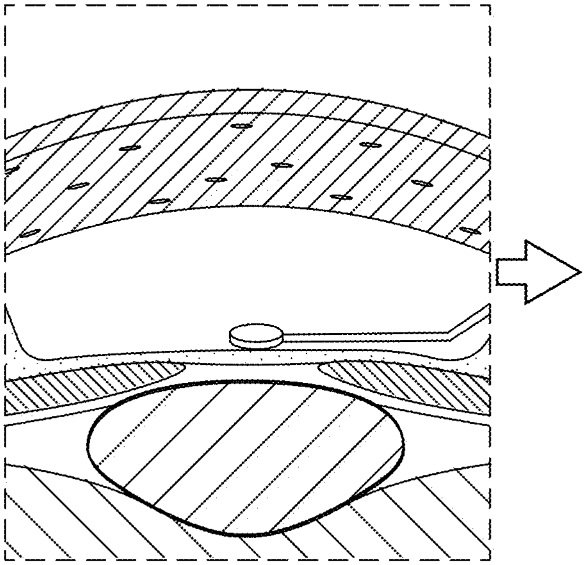
Figure 22E:
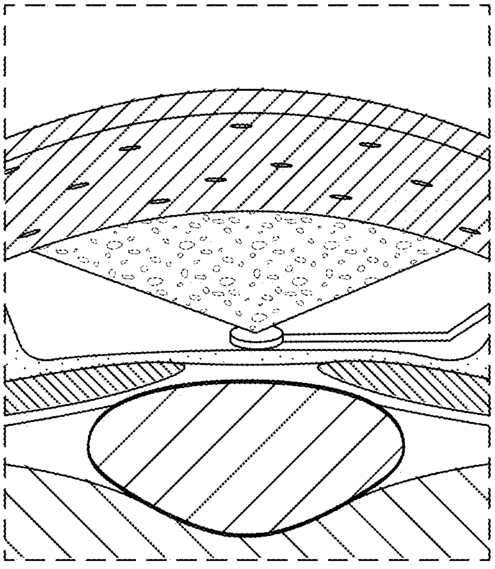
Figure 22F:
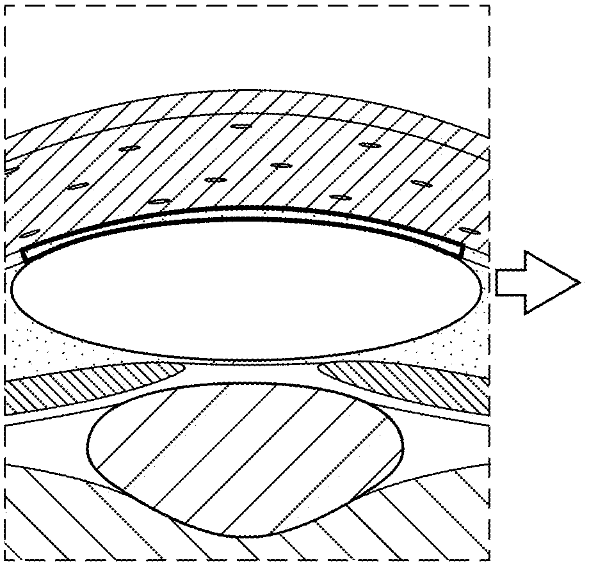
Figure 22G:
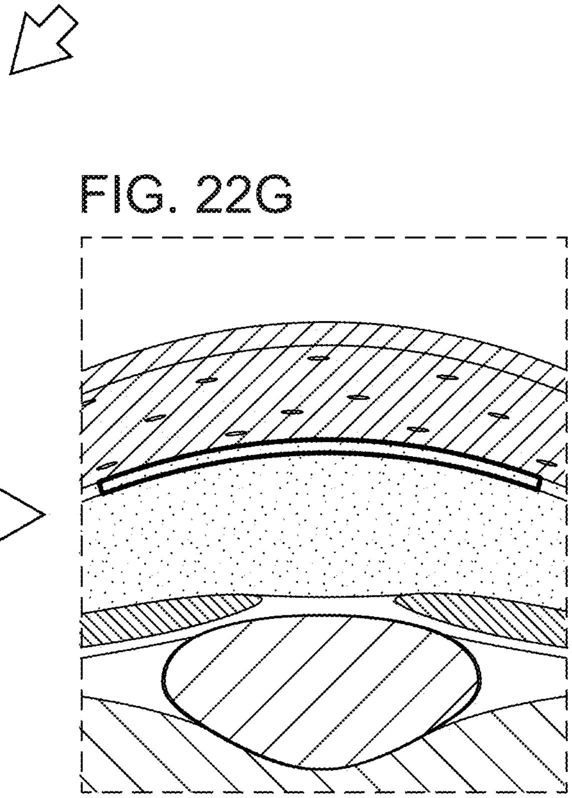

FIG. 21A-21B. CB[8]-based supramolecular gelatin hydrogels support cell growth and proliferation. (FIG. 21A) Cell density of MRC-5s encapsulated in the hydrogels after 2 h, 2 days, and 7 days, as measured by calcein AM staining and normalized to the average cell density after 2 h. (FIG. 21B) Adjusted cell count for MRC-5s encapsulated in the hydrogels after 2 h, 2 days, and 7 days, normalized to the cell count after 2 h and adjusted based on the calculated mass swelling ratio at each time point. Data are presented as mean±SD, determined using 8-9 z-stacks (2-3 independent hydrogel replicates per condition).

FIG. 22A-22G illustrates how corneal endothelial cells can be delivered to the posterior cornea through the present invention. Underneath (FIG. 22A) a cornea where diseased or damaged endothelium and descemet's membrane have been removed, (FIG. 22B) an air or gas bubble is instilled into the anterior chamber using a cannula until (FIG. 22C) the majority of the anterior chamber is filled with the air or gas bubble. (FIG. 22D) Another cannula is then placed that (FIG. 22E) is able to eject or (in one embodiment) spray cells suspended within the supramolecular gel containing cultured endothelial cells. (FIG. 22F) The gel is allowed to spread and form as a thin layer on the posterior surface of the cornea under an air (or gas)-liquid interface by virtue of the presence of the air or gas bubble, which tamponades the cell-containing matrix to the posterior stromal surface. (FIG. 22G) The air or gas bubble over time dissipates and is replaced with aqueous humor, and the gel degrades away, leaving behind the layer of transplanted, functional endothelial cells attached to the posterior cornea which serve to deturgesce (dehydrate) the edematous cornea.

DETAILED DESCRIPTION

The invention described below relates to injectable compositions and methods for in-situ forming tissue constructs that find use in partial or total repair, regeneration, and/or reconstruction of wounded tissue in a mammalian subject or host organism. Other purposes of the instant disclosure include, but are not limited to, the use for effective transplantation of cells into the host organism to encourage recellularization of wounded tissue, and the use as a tissue model for the in-vitro study of cellular responses and interplay.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting. Although a number of methods and materials similar or equivalent to those described herein can be used in the practice of the present invention, the preferred materials and methods are described herein.

In describing embodiments of the present invention, the following terms will be employed, and are intended to be defined as indicated below. As used in this specification and the appended claims, the singular forms "a," "an" and "the" include plural referents unless the content clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The practice of the present invention will employ, unless otherwise indicated, conventional methods of medicine, pharmacology, chemistry, biochemistry, molecular biology and recombinant DNA techniques, within the skill of the art. Such techniques are explained fully in the literature. See, e.g. S. S. Wong and D. M. Jameson Chemistry of Protein and Nucleic Acid Cross-Linking and Conjugation (CRC Press, 2Supnd/Sup edition, 2011); G. T. Hermanson Bioconjugate Techniques (Academic Press, 3Suprd/Sup edition, 2013); B. Bowling Kanski's Clinical Ophthalmology: A Systematic Approach, 8e (Saunders Ltd., 8Supth/Sup edition, 2015); A. L. Lehninger, Biochemistry (Worth Publishers, Inc., current addition). All publications, patents and patent applications cited herein, whether supra or infra, are hereby incorporated by reference in their entireties.

As used herein, "about" or "approximately" mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not.

"Statistically significant" difference means a significance is determined at a confidence interval of at least 90%, more preferably at a 95% confidence interval.

The terms "treatment," "treating," "treat," and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease.

The terms "reconstructing" and "reconstruction," and the like are used herein to generally refer to rebuilding, healing and regenerating an injured matter or tissue.

The term "subject" or "mammalian subject" refers to any mammalian subject for whom treatment or therapy is desired, particularly humans. "Mammal" for purposes of treatment refers to any animal classified as a mammal, including humans, domestic and farm animals, and zoo, sports, or pet animals, such as non-human primates, dogs, horses, cats, cows, sheep, goats, pigs, camels, etc. In some embodiments, the mammal is a human.

The term "therapeutically effective amount" or "effective amount" means the amount of a compound, agent, composition, construct that when administered to a mammalian subject for treatment is sufficient, in combination with another agent, or alone in one or more doses or administrations, to effect such treatment for the disease. The "therapeutically effective amount" will vary depending on the compound, agent, composition, construct, the defect or disease to be treated, and its severity and the age, weight, etc., of the mammalian subject to be treated.

As used herein, the term "cell" in the context of the in-vivo and in-vitro applications of the present invention encompasses mammalian cells of any genus or species. The types of cells that may be incorporated into the polymeric biomaterial include progenitor cells of the same type as those from the tissue site, and progenitor cells that are histologically different from those of the tissue site such as embryogenic or adult stem cells, that can act to accelerate the healing, regenerative or reconstructive process. The compositions comprising cells can be administered in the form of a solution or a suspension of the cells mixed with the polymeric biomaterial solution, such that the cells are substantially immobilized within the application site upon gelation. This serves to concentrate the effect of the cells at the site of application and to provide for release of the cells over a course of time.

Somatic stem cells are characterized as cells with the ability to self-renew and give rise to differentiated progeny via mitosis. These adult stem cells are often found in specialized locations, or niches, in tissues throughout the body. When tissue is damaged, stem cell populations are often instrumental in replacing the lost cells to restore tissue function and integrity. Stem cells are found in many different tissues, including hematopoietic stem cells in the bone marrow, muscle stem cells, neural stem cells, etc. and may be isolated from tissues, or can be differentiated in vitro from pluripotent stem cells. Corneal cells, for example limbal epithelial stem cells, stromal corneal stem cells, keratinocytes, etc. may be isolated, harvested, and/or propagated from cadeveric donor corneal tissue, from small limbal biopsies from patients (either autologous from one's healthy eye, or from another living patient's eye as a donation); generated by in vitro culture, etc. Cells of interest for delivery also include mesenchymal stromal cells and mesenchymal stem cells of all tissue types including those derived from the cornea and bone marrow.

In the cornea, stem cells include limbal epithelial stem cells (LESCs), which may be found at the limbal region that marks the transition zone between cornea and conjunctiva. Keratin expression is distinct in these limbal basal cells, with a lack of cytokeratins CK3 and CK12, and expression of CK14/CK59-11. The cells are also positive for adult stem cell marker ABCG2. ABCB5, a member of the ATP-binding cassette family of proteins, has also been identified as a definitive LESC marker. Expansion of limbal cells in vitro and transplantation to central cornea can restore epithelial function.

Corneal stem cells also include corneal stromal stem cells and corneal mesenchymal stromal cells (c-MSCs), and keratocytes as well as limbal corneal epithelial cells. Corneal stromal stem cells (CSSC) have also been shown to produce a collagenous matrix similar to that seen in the corneal stroma. Corneal limbal epithelial cells and corneal endothelial cells can also be encapsulated and delivered within the materials of the present invention.

For in vivo application, the polymeric compositions and cells can be mixed and then applied to the in vivo site. The cells are preferably added to the polymeric compositions immediately prior to administration to the application site to enhance survival of living cells. The cells of the thus resulting cellularized hydrogel may maintain a cellular phenotype at the site of application, which is usually the affected, i.e. damaged, area for at least one day, one week, or one month following application. Where the polymeric composition is administered in a two solution format, it can be complexed in situ for tissue repair or regeneration.

Therapeutically effective amounts of the cells encapsulated within a hydrogel of the instant disclosure will vary depending e.g., on the condition to be treated, typical survival of the particular cell type within the hydrogel construct (e.g., including the average lifespan of cells of the particular cell type), etc.

In one embodiment, limbal corneal epithelial cells cultured from an allogeneic source (e.g. from a donor cornea) or an autologous source (e.g. from a healthy, contralateral eye) can be encapsulated and delivered to an ocular surface. Such an ocular surface, for example, can be deficient in or have dysfunctional limbal epithelial cells, and thus would benefit from the delivery of healthy limbal epithelial cells to the periphery of the cornea. The supramolecular gel containing the limbal cells can be applied directly by injecting the gel under shear to the surface and location desired (e.g. the periphery of the cornea) after limbus-to-limbus debridement and/or partial keratectomy including the peripheral cornea, and in some cases, part of the adjacent scleral tissue. The gel can be left as a thin layer, or covered by a contact lens, and/or a tarsorraphy (sutured eyelid closure). The gel with cells can also be applied in other ways, for instance as a spray (in the form of droplets) that settles as a thin layer on the cornea.

In another embodiment, corneal endothlelial cells cultured from an allogeneic source (e.g. from a donor cornea) or an autologous source (from a health contralateral eye) can be encapsulated and delivered to a posterior ocular surface after remove of the diseased or damaged endothelium and descemet's membrane (such as in the case of Fuchs' endothelial dystrophy or pseudophakic bullous keratopathy). In this case, an air or gas bubble (such as 20% sulfur hexafluoride or SF6) is instilled into the anterior chamber to create an air or gas bubble that contacts all the surfaces of the anterior chamber including the posterior cornea. The supramolecular gel containing endothelial cells can then be applied to the posterior surface of the cornea within the air or gas bubble, either by contacting the gel extruding under pressure and shear through a needle or surgical cannula, or by spraying or ejecting the gel with cells toward the posterior surface of the cornea. Upon contact with the posterior cornea, the gel with cells spreads out into a thin layer. The endothelial cells are then able to attach to the posterior cornea while the air or gas bubble is in place; the air or gas bubble eventually dissipates over the ensuing days, as it typically does after endothelial transplant surgery (e.g. descemet's membrane endothleial keratoplasty (DMEK) or descemet's stripping automated endothelial keratoplasty (DSAEK)). Without the presence of crosslinks to keep the gel in a defined shape (in this case, a thin membrane) after placement, the cells would not have the opportunity to adhere to the posterior cornea where they are needed to treat corneal edema as they can float away into the anterior chamber. The gel sequesters the cells to the desired location while the air or gas bubble flattens the gel into a thin membrane that resembles that of a typical human donor graft comprising endothelial cells upon a thin layer of support tissue (e.g. descemet's membrane or descemet's membrane with a thin layer of posterior stroma). The applied gel may be further crosslinked either non-covalently (such as ionically, with calcium) or covalently (such as by photochemical crosslinking with an external illuminator either from within the anterior chamber or above, through the cornea) while the bubble is in place. The aforementioned approach to delivering endothelial cells into the anterior chamber has advantages over simple injection of a suspension of cells, which requires face-down (prone) positioning to allow the cells to settle by gravity on the posterior cornea but does not prevent cells from scattering through the aqueous humor when the patient gets up. It has advantages over conventional DMEK and DSAEK surgical techniques because it does not require delivery of a fragile, thin membrane (descemet's membrane with endothelial cell monolayer) that needs to be carefully scrolled or folded and then deployed and unscrolled within the anterior chamber which can be challenging, followed by air or gas bubble administration to taponade the cellular membrane to the posterior cornea. By injecting the supramolecular gel containing cells, the cells are pre-cultured (and thus, a one-to-one donor-to-recipient exchange is not needed), and are protected within the supramolecular gel during the procedure.

In some embodiments, a therapeutically effective amount of cells is $1\times10^3$ or more cells, including e.g., $5\times10^3$ or more, $1\times10^4$ or more, $5\times10^4$ or more, $1\times10^5$ or more, $5\times10^5$ or more, $1\times10^6$ or more, $5\times10^6$ or more, $1\times10^7$ or more, $5\times10^7$ or more, $1\times10^8$ or more, $5\times10^8$ or more, $1\times10^9$ or more, $5\times10^9$ or more, $1\times10^{10}$ or more, $5\times10^{10}$ or more. The hydrogel can be seeded with cells and used to repair and regenerate damaged corneal or generally ophthalmic tissue.

The defined hydrogel structure provides a three-dimensional construct for new cell growth. The hydrogels of the present invention can be used not only for the encapsulation of cells, but also for the encapsulation of other molecules and agents that may enhance proper remodeling of the complexed polymer so that its contents are replaced with the matrix elements native to the surrounding tissue (e.g. in the cornea, the complexed matrix is eventually broken down and replaced by normal corneal tissue).

As used herein, the term "under physiological conditions" encompasses those conditions that are compatible with living cells, e.g., predominantly aqueous conditions of a temperature, pH, salinity, osmolarity, osmolality etc.

The term "gel" or "hydrogel," as used herein, refers to a complexed network of hydrophilic biopolymers. Hydrogels of the instant disclosure will generally be made by combining a first flowable composition containing reactive groups of one nature and a second flowable composition containing reactive groups of a different nature, and possibly more flowable compositions with reactive groups of further different nature. The flowable compositions may be combined in situ, or may be combined to form on demand via thiol-ene reactions between preassembled CB[8]·peptide ternary complexes and grafted norbornenes.

The term "biopolymer" refers to a biocompatible polymers comprising polymers that can be found naturally in organisms, as well as chemical and physical modifications of such polymers, and include, but are not limited to, proteins, fibrins, fibrinogen, collagens, gelatins, elastins, laminin, fibronectin, extracellular matrix constituents, glycosaminoglycans, chondroitin sulfate, keratan sulfate, dermatan sulfate, heparan sulfate, hyaluronic acid, albumin, alginates, chitosans, cellulose, thrombin, heparin, polysaccharides, synthetic polyamino acids, prolamines, derivatives, combinations thereof, and other such molecules.

Naturally occurring polymers include, but are not limited to, proteins and carbohydrates. The term "bio-polymer" also includes derivatised forms of the naturally occurring polymers that have been modified to facilitate cross-linking to a synthetic polymer of the invention. Additionally, the term "bio-polymer," as used herein, includes proteins produced using recombinant methodologies, such as, for example, recombinant collagen.

Combinations of biopolymers can be used, to form compositions such as an interpenetrating polymer network, semi-interpenetrating polymer networks, or copolymer networks. Combinations may be combined in different ratios, e.g. where two biopolymers are used, a ratio may be 1:50; 1:10, 1:5, 1:3, 1:2, 1:1; 2:1; 3:1; 5:1; 10:1; 50:1; etc. For example, gelatin or collagen can be complexed in the presence of uncomplexed hyaluronic acid and/or chondroitin sulfate to form a semi-interpenetrating polymer network of collagen and hyaluronic acid (and/or chondroitin sulfate). In another embodiment, hyaluronic acid can be complexed in the presence of collagen to form a semi-interpenetrating polymer network. In another embodiment, conjugated collagen and hyaluronic acid can be complexed to each other to form a variant of a copolymeric network. In still another embodiment, collagen can be complexed in an independent process from the crosslinking of hyaluronic acid (either simultaneously or in sequence) to yield a fully interpenetrating polymer network.

When used as tissue constructs in tissue engineering for replacing or restoring tissue and organ function, as contemplated herein, hydrogels of the present invention may contain mammalian cells, such as stem cells, keratocytes and keratinocytes, in order to repair tissue or to promote tissue repair, reconstruction and regeneration. The hydrogels of the present invention can be prepared with enhanced mechanical as well as structural properties and resistance to degradation, can be made visually transparent and because of their cytocompatibility support cell overgrowth, in-growth and encapsulation of cells.

The hydrogels may also comprise factors derived from cells including growth factors, exosomes, vesicles, genetic material such as various forms of DNA and RNA, antibodies, other biologica, drugs, etc.

A hydrogel in accordance with the present invention comprises a supramolecular assembly of polymers and is suitable for use in a variety of applications, including, but not limited to, clinical, therapeutic, prophylactic, or cosmetic applications. The hydrogel material can be used to replace, restore, and/or augment tissue and/or organ function in a mammalian subject in need thereof. Various biomedical, biotechnological, and/or pharmaceutical applications include, for example, corneal substitutes, therapeutic lenses, cell and/or drug delivery carriers, and tissue engineering scaffolds. Besides benefitting therapeutically in the treatment of a disease, disorder or traumatic injury of an eye and, and enhancing corneal regeneration and reconstruction, hydrogels in accordance with the present invention can be used in ophthalmic devices to enhance optical power or comfort.

Hydrogels of the invention can be adaptable to complicated defect sites when compared to structurally preformed covalently crosslinked hydrogels. The gel is intended to be pre-mixed and, in some embodiments, exposed to light prior to delivery at the site of interest, and then injected from there. Thus, the material is already a pre-mixed, pre-formed gel prior to delivery that then shear-thins under pressure applied to push it through a catheter, needle, or cannula to enable injection and then self-heals at or within the site of interest, taking on the dimensions of the cavity in which it is being placed. With a structure that forms in situ and which are contemplated herein, one or more solutions containing the pre-gelled solution are injected or otherwise delivered to the site where the hydrogel is to be used. Because of their shear-thinning and self-healing properties, the hydrogels of the present invention can encapsulate and transport highly sensitive cells and other biological additives.

Polymeric hydrogels can be defined as two- or multicomponent systems consisting of a three-dimensional network of polymer chains, and water that fills the space between macromolecules. A hydrogel is a network of polymer chains that are water-insoluble, sometimes found as a colloidal gel where water is the dispersion medium. Hydrogels are superabsorbent (they can contain over 99% water) natural or synthetic polymers. Hydrogels possess also a degree of flexibility that is very similar to natural tissue, due to their considerable water content. In physical hydrogels, the chains are connected by electrostatic forces, hydrogen bonds, hydrophobic interactions or chain entanglements; those gels are prone to temperature changes and usually transform to polymer solutions at particular temperatures. Physical crosslinking of polymer chains can be achieved using a variety of environmental triggers (pH, temperature, ionic strength) and a variety of physicochemical interactions (hydrophobic interactions, charge condensation, hydrogen bonding, or supramolecular interactions).

An in-situ forming tissue construct is formed by application of a biomaterial comprising a supramolecular material, which can be administered as a single composition. Supramolecular assemblies, such as "host-guest" complexes are shear-thinning as well as "self-healing" or "self-repairing", where defects in a gel matrix are spontaneously repaired by re-assembly of the non-covalent interactions. The biomaterial offers advantages for in situ therapeutic applications in that a biomaterial can be injected into or onto a wound site without the need for mixing of two or more components, or other excipients or catalysts, and the material can take on the shape of the cavity it is placed in without any further stimulus or chemical reaction.

The term "biocompatible" refers to the absence of stimulation of a severe or escalating biological response towards administration of a composition, and is distinguished from a mild, transient inflammation which typically accompanies surgery or implantation of foreign objects into a living organism.

The term "polymer," as used herein, refers to a molecule consisting of individual monomers joined together. Polymers that are contemplated herein can be naturally occurring, synthetically produced, or produced using recombinant methodologies.

The term "transparent," as used herein, refers to at least 70%, 80, or 90% transmission of white light.

An in-situ forming tissue construct is formed by application of a biomaterial comprising a supramolecular material, which can be administered as a single composition. Supramolecular assemblies, such as "host-guest" complexes are, may be generated in situ, or may be generated prior to administration by combining biopolymers conjugated to appropriate reactants. In some embodiments reactants form host-guest complexes, e.g. adamantane+cyclodextrin; adamantaine+cucurbit[n]urils, and the like, which form assemblies through non-covalent interactions. This leads to the unique property of supramolecular materials to be shear-thinning as well as "self-healing" or "self-repairing", where defects in a gel matrix are spontaneously repaired by re-assembly of the non-covalent interactions. The biomaterial offers advantages for in situ therapeutic applications in that a biomaterial can be injected into or onto a wound site without the need for mixing of two or more components, or other excipients or catalysts, and the material can take on the shape of the cavity it is placed in without any further stimulus or chemical reaction.

In some embodiments, a single supramolecular composition can be injected (via shear-thinning) and then re-form on the wound site. In others, the two parts (conjugated molecule A and conjugated molecule B) are mixed either on the site or immediate before application on the site. In this sense the covalent and non-covalent approaches are similar (can be mixed on site), with the non-covalent interactions having the advantage of being able to "shear thin" (become flowable with shear) and then gelate again (and "heal" by reforming of the non-covalent interactions that need to be disrupted upon injection.)

In such an embodiment, biopolymers, which may be the same or different, may be modified to comprise reactive groups, where a first reactive group is an adamantyl group and a second reactive group is group that complexes with adamantane, e.g. cyclodextrin, cholesterol, cucurbit[n]urils, particularly CB[7], and the like. See, for example, Osman et al. (2011) Polymer52:4806-4812; Koopmans and Ritter (2008) Macromolecules 41:7418-7422; Charlot and Auzely-Velty (2007) Macromolecules 40:1147-1158; and Sasmal et al. (2018) Anal90:11305-11314, each herein specifically incorporated by reference. Combining the modified biopolymers with these reactive groups provides for a strong non-covalent association.

Polyethylene glycol chains of various lengths can be used as spacers within the functionalization process, wherein the first end of the polyethylene glycol chain is covalently linked to a reactive group, as defined herein.

The pharmaceutically acceptable excipients, such as vehicles, adjuvants, carriers or diluents, are readily available. Moreover, pharmaceutically acceptable auxiliary substances, such as pH adjusting and buffering agents, tonicity adjusting agents, stabilizers, wetting agents and the like, are readily available.

Polymers contemplated for use in the instant disclosure as exemplary hydrogel-forming molecules include glycoproteins, carbohydrates, and other macromolecules, including, but not limited to, various types of collagen, proteins, fibrins, fibrinogen, collagens, gelatins, elastins, laminin, fibronectin, extracellular matrix constituents, glycosaminoglycans (including sulfonated glycosaminoglycans such as chondroitin sulfate, keratan sulfate, dermatan sulfate, and heparan sulfate), hyaluronic acid, proteoglycans, albumin, alginates, chitosans, cellulose, thrombin, heparin, polysaccharides, synthetic polyamino acids, prolamines, hydroxy methylcellulose, chitosan, derivatives and/or combinations thereof, and other such molecules, including recombinant versions of such polymers.

Collagen, a widely used biomaterial for producing tissue scaffolds and constructs, is the major constituent of the extracellular matrix, and has been used as wound dressing, corneal shields, and engineered corneal matrix. It is well known that collagen's molecular structure plays a crucial role in cell adhesion, migration, and differentiation.

In various embodiments of the present invention in order to demonstrate the utility of the described precursor compositions to form in-situ a tissue construct at the site of a corneal defect, bovine type-I collagen was employed as matrix due to its low immunogenicity compared to other collagen types. Collagen type I is commonly used as a cellular scaffold in three-dimensional cell culture because collagen gel matrices are more similar to the native cell environment than general two-dimensional cell culture dishes. When an acidic collagen solution is neutralized and incubated at 20-37° C., the collagen forms a gel through fibril formation. However, collagen extracted from tissue loses its original fibril density and three dimensional architecture, and as a result, neutralized non-crosslinked collagen gels have low mechanical strength.

The physical properties of collagen can be modulated by complexing or crosslinking techniques that enhance mechanical strength, enzymatic degradation resistance, and transparency.

Hyaluronic acid is another polymer of interest, which may be used alone or in combination with collagen. It is a polymer of disaccharides, themselves composed of D-glucuronic acid and N-acetyl-D-glucosamine, linked via alternating β-(1→4) and β-(1→3) glycosidic bonds. Polymers of hyaluronic acid can range in size from 5,000 to 20,000,000 Da in vivo. The average molecular weight in human synovial fluid is 3-4 million Da, and hyaluronic acid purified from human umbilical cord is 3,140,000 Da. Hyaluronic acid is energetically stable, in part because of the stereochemistry of its component disaccharides. Bulky groups on each sugar molecule are in sterically favored positions, whereas the smaller hydrogens assume the less-favorable axial positions.

Hydrogel Materials

In some embodiments the hydrogel comprises cucurbit[8]uril (CB[8])-based crosslinks that form on demand via thiol-ene reactions between preassembled CB[8]·peptide ternary complexes and grafted norbornenes.

Cucurbit[n]urils are rigid, symmetric cavitands composed of n methylene-linked glycouril oligomers that form a hydrophobic cavity laced with ureido-carbonyl oxygens possessing very high quadrupole moments. Due to a combination of hydrophobic and ion-dipole interactions, CB[8] ternary complexes are highly selective with very high association rates and binding equilibrium constants (up to $10^{14}$ $M^{-2}$ under idealized conditions). A first component therefore comprises peptides with an N-terminal phenylalanine and a C-terminal cysteine that are pre-complexed with CB[8]. The complexation can be achieved by incubating a cucurbit[n]uril hydrate and peptide in a suitable buffer, e.g. a HEPES buffered physiological saline.

The second component is a biopolymer modified with norbornene. Norbornene or norbornylene or norcamphene is a highly strained bridged cyclic hydrocarbon. The molecule consists of a cyclohexene ring with a methylene bridge between carbons 1 and 4. The molecule carries a double bond which induces significant ring strain and significant reactivity. Norbornene is made by a Diels-Alder reaction of cyclopentadiene and ethylene. Many substituted norbornenes can be prepared similarly.

Norbornene-functionalized biopolymers may be prepared by dissolving a suitable biopolymer, e.g. a biopolymer comprising amine groups, e.g. lysine, for modification. Carbic anhydride is added to the biopolymer and allowed to react at a pH of about 8. The level of modification may be assayed, for example, by determining the level of unmodified lysine relative to a control. The maximum degree of modification is limited by the degree of lysine modification with norbornene reactive handles, which may be, for example, from about 10% to about 100%, from about 20% to about 90%, from about 30% to about 80%, from about 40% to about 70%.

The preassembled CB[8]·peptide ternary complexes and grafted norbornenes are combined, e.g. in a molar ratio to maximize interactions. The biopolymer may be present in solution at a concentration of from about 1%, 2.5%, 5%, 7.5%, 10%, 12.5%, and up to about 15% weight/volume. Agents such as cells, proteins, therapeutic agents and the like can be present in the solution. Gelation is rapidly triggered by adding a radical initiator, e.g. Irgacure, lithium phenyl-2,4,6-trimethylbenzoylphosphinate (LAP), etc. to the solution and equilibrating to room temperature. For photoinitiation the mixture is exposed to a suitable wavelength for the reaction, e.g. 365 nm light for LAP. Gelation is complete in a short period of time, e.g. less than about 30 minutes, less than about 20 minutes, less than about 10 minutes. The resulting gel is injectable, shear-thinning, and self-healing, and thus can be applied directly from a syringe to another site.

The resulting hydrogel is stable, and promotes uniform distribution, viability, and spreading of encapsulated cells and/or therapeutic factors. For therapeutic applications, this means that the gel can be administered from a syringe to, for example, a wound site without the need for any additional trigger such as light, heat, or chemical catalyst that may adversely affect surrounding tissue. Unlike the random chain-growth polymerization chemistries previously exploited to prepare CB[8]-based hydrogels, or gelatin-polyacrylate hybrid hydrogels with supramolecular cross-links between naturally occurring gelatin aromatic amino acids and pendant cyclodextrins on the in situ polymerized polyacrylate backbone, thiol-norbornene photoreactions are not oxygen inhibited, require relatively low radical concentrations, produce single polymer hydrogel networks, and present a reduced risk of radical-mediated damage for sensitive cell types.

In other embodiments, a hydrogel is formed by host-guest complexation chemistry. In such embodiments, a biopolymer of interest or a mixture of biopolymers of interest are conjugated to either a host or a guest moiety. Examples of host moieties include, for example, cyclodextrin and Cucurbit[n]urils (CB[n], n=5-8,10, 14). For example, cucurbit[n]uril can be conjugated to a biopolymer of interest. It forms exceptionally stable host-guest complexes with specific guest molecules in solution as well as in the solid state. Suitable guest molecules include, for example, ferrocene, cobalotocene, bicyclo[2.2.2]octane, diamantane and adamantane derivatives. Conjugation reactions may be performed as known in the art.

For example, to generate a cyclodextrin conjugate, succinyl-β-cyclodextrin, EDC and NHS can be dissolved in buffer with a biopolymer of interest, e.g. a biopolymer comprising free amino groups, such as lysine. Adamantane conjugates can be generated by combining Ad-$CO_2H$ in DMSO with the biopolymer, in the presence of 4-dimethylaminopyridine and di-tert-butyl decarbonate (BOC anhydride).

The host conjugated and the guest conjugated biopolymers may be combined prior to use, or may be provided as two solutions and combined at the site. The biopolymers may be present in solution at a concentration of from about 1%, 2.5%, 5%, 7.5%, 10%, 12.5%, and up to about 15% weight/volume. Agents such as cells, proteins, therapeutic agents and the like can be present in the solution. The ratio of host and guest conjugates may be from about 2:1, 1:1, 1:2 molar ratios.

Cellularized or Acellular Compositions

For each type of tissue being replaced, the flowable biomaterial compositions can be injected with cells, i.e. cellularized, or without cells, i.e. acellular. Such cells can be somatic/differentiated cells, induced pluripotent stem cells, or progenitor/stem cells.

The in-situ encapsulation of corneal keratocytes within gels to support corneal re-epithelialization was investigated in complexed gels. To mimic the structure of the cornea which is composed of a multi-layered epithelium of keratinocytes overlying a stromal layer of collagen type I and keratocytes, keratinocytes are cultured on collagen gels with encapsulated keratocytes, whereby the collagen was either complexed or not. Cell behavior, phenotype, and cytocompatibility of encapsulated keratocytes were evaluated as a function of complexation and mechanical properties. Corneal keratinocytes were cultured on the complexed gel and were able to adhere and migrate over the surface (shown in FIG. 1)

As described herein, such in-situ formed constructs or scaffolds are able to support a co-culture of keratocytes within their matrix and keratinocytes on their surface, and can be provided as cellular or acellular lamellar substitutes to facilitate multilayered re-epithelialization of wounded corneal stromal tissue. In addition, such scaffolds provide a three-dimensional in-vitro model system for studying keratocyte-keratinocyte interactions within corneal tissue.

Methods

In some aspects of the invention, methods are provided for treating an injury, wound or defect that requires tissue regeneration, tissue replacement or repair, regeneration, and/or reconstruction of ocular, skin, subcutaneous tissue, nerve, muscle, bone, cartilage, vitreous, tendon, ligament, fat, retinal, conjunctival, scleral, cardiac, adrenal, and other types of tissue. In these methods, flowable biomaterials are applied to a site of injury, wound or defect where, upon crosslinking or complexation of reactive groups, a defined hydrogel structure tissue construct is formed in-situ on top of the injury, wound or defect, which serves to regenerate, reconstruct and repair the tissue injury, wound, or defect.

The injectable flowable biomaterial compositions and methods of the present invention can be applied to any clinical situation where tissue engineering, regeneration or reconstruction in a mammalian host or subject is necessary. Tissue engineering is a rapidly growing field encompassing a number of technologies aimed at replacing or restoring tissue and organ function. The key objective in tissue engineering is the regeneration of a defective tissue through the use of materials that can integrate into the existing tissue so as to restore normal tissue function. Such injectable compositions can comprise cells that settle in the host and encourage recellularization of the wounded tissue. Furthermore, such injectable compositions can also serve as a three-dimensional tissue model for the in-vitro study of cellular responses and interplay.

Application as In-Situ Forming Hydrogel Upon Ocular Defects

To address an unfilled need for effective compositions and methodologies to treat and regenerate ocular defects, including corneal defects, precursor compositions are described in various examples herein that upon injection form in-situ corneal constructs on top of corneal defects. Such ocular and corneal defects may be caused by, e.g., neurotrophic keratopathy, recurrent corneal erosion, corneal ulcer, corneal burns, exposure keratopathy, physical trauma, retinal disease, retinal degeneration, optic nerve damage, optic nerve degeneration, and other disorders.

The cornea is a highly specialized transparent tissue and, as the most anterior ocular tissue, protects the eye by acting as a physical barrier. It is comprised of three cellular layers: the outer layer being the stratified squamous corneal epithelium, the center layer being the corneal stroma, and the inner layer being the corneal endothelium. The corneal stroma makes up the majority of the corneal tissue. The extracellular matrix (ECM) of the corneal stroma has a lamellar, highly organized structure that facilitates the transparency of the cornea, whereby each lamella is composed of tightly organized collagen fibrils. Keratocytes are mesenchymal-derived cells that are quiescent in the mature cornea and that are arranged within the corneal stroma. Upon injury to the cornea, the keratocytes become activated, and several changes in the corneal stroma occur. Upon an initial apoptotic phase, keratocytes lose their quiescence, start to divide and develop either into phenotypes that start to secrete extracellular matrix for corneal regeneration or into phenotypes that induce fibrotic scar formation at the site of injury. Unlike in uninjured stromal tissue, the extracellular matrix in scar tissue is disorganized and opaque, and may seriously impair visual acuity and lead to blindness.

Delivering (cultured) keratocytes that are not activated to the site of corneal injury may minimize the fibrotic response and enhance the regeneration of the corneal tissue. Delivery of corneal cells, such as keratocytes and keratinocytes, and other cells, within injectable supramolecular hydrogels, as described herein, may be instrumental in repairing and regenerating corneal tissue. The cells can then be encapsulated into the corneal construct to provide a scaffold for proliferation and reepithelialization of the corneal defect.

Such compositions may comprise functionalized (bio) polymers such as collagen (type I) that are assembled by supramolecular CB[8]-mediated crosslinks into a substantially transparent gel or hydrogel that serves as a corneal stromal scaffold, substitute or construct on top of a corneal or stromal defect, wound or wounded area to enhance the regenerative capacity of the cornea to restore viable corneal tissue.

Such polymer-based supramolecular hydrogels, which can additionally contain a suspension of corneal stromal stem cells or corneal mesenchymal stromal cells or stromal keratocytes to aid in the reepithelization of the wounded corneal area, are applied as flowable hydrogels to a wounded corneal area, and then self-heal on the spot (in situ) to produce an in situ-forming corneal stromal scaffold which is kept in place on top of the wound site. The in situ-formed scaffold mimics the thickness and smooth, continuous surface of the cornea.

We have demonstrated herein the capacity of supramolecular HA (s-HA) hydrogels formed by CD and adamantane (Ad) host-guest interactions to heal corneal woundsevaluating the unique ways in which they can foster cell growth in several specific ways. We evaluated the impact of the hydrogel on corneal wound healing by investigating (1) its ability to facilitate migration of encapsulated epithelial cells through dynamic bulk changes in porosity, (2) its influence on corneal stromal cells' secretion of trophic factors, and (3) its overall effect on corneal wound healing in vivo as an in situ-formed, acellular therapeutic membrane. The s-HA gels were found to have a profound effect in particular on reducing the degree of stromal cell activation and edema, both of which are important indices of visual recovery after injry. Our results indicate that by virtue of these unique, spatiotemporal effects, s-HA hydrogels are a promising and versatile biomaterial platform for fostering corneal wound healing as an in situ-forming, wound stabilizer for the ocular surface, and further work is merited to develop and characterize it further for regenerative medicine applications in the eye.

In-Situ Molding

In embodiments of the present invention, the complexed gel can be applied with or without cells, and with or without an overlying contact lens (hard or soft lens) which can be used as an in situ mold to create the desired contour and curvature of the complexed gel on the ocular surface. This in situ molding process may be important for bestowing the desired refractive power to the surface of the cornea, since the air-cornea interface is responsible for most of the refractive power of the eye. By providing a smooth, transparent, and properly curved surface to the central cornea, the gel can restore vision to patients whose vision was severely compromised by a central defect or ulcer. Furthermore, the gel can be applied to any part of the cornea (central, paracentral, or peripheral cornea), and can be used to encapsulate stromal cells, epithelial cells, limbal cells, or combinations thereof. In other embodiments, the eyelids can be sutured shut (i.e. tarsorraphy can be placed) completely or partially to create a protective environment for the eye after the gel is placed. This can be done with or without a contact lens in place over the cornea and applied gel.

Application as In-Situ Forming Hydrogel Upon Other Defects

The compositions and methods of the present invention can be configured to a range of applications to facilitate tissue regeneration (e.g., bone or muscle formation) or to replace tissues such as adipose tissue (e.g., in cosmetic or reconstructive surgeries), blood vessels and valves (e.g., in angioplasty, vessel inflammation, or valve deterioration), or skin (e.g., in cases of skin damage due to heat, mechanical force or by disease). As such, the compositions and methods of the present invention find use for the repair, regeneration, and/or reconstruction of skin, cornea, conjunctiva, subcutaneous tissue, nerve, muscle, bone, cartilage, vitreous, tendon, ligament, fat, retinal, conjunctival, scleral, cardiac, adrenal, and other types of tissue. Such repair, regeneration, and/or reconstruction may also be necessary following injuries that may be associated with or result from ischemia, infections, inflammation, auto-immune reactions, organ failures, fibrosis, periodontal diseases, and can concern tissues of solid organs, e.g., kidney, liver, large intestine, small intestine, skeletal muscle, heart, pancreas, lung.

Kits

The present invention also provides kits comprising separate containers holding compositions of hydrogels comprising polymers, such as collagen, hyaluronic acid, etc., that are functionalized with the groups described herein, and optionally admixed with living cells to be delivered to the wounded tissue site. For example, collagen, hyaluronic acid, etc., are functionalized with adamantane groups, and polymers that are functionalized with groups such as CB[7], cyclodextrin, cholesterol, etc., and optionally with spacer arm(s) bridging the reactive groups to the polymer, and optionally admixed with living cells to be delivered to the wounded tissue site, which polymers may be admixed or may be provided in separate containers. Suitable containers for the compositions include, for example, bottles, vials, syringes, and test tubes. Containers can be formed from a variety of materials, including glass or plastic.

The kit can further comprise a container comprising pharmaceutically acceptable excipients or formulating solutions such as buffers, diluents, filters, needles, and syringes or other delivery devices. The kit can also comprise a package insert containing written instructions describing methods for care of a corneal wound as described herein.

Administration

The flowable biomaterial compositions of the present invention can be administered in the form of pharmaceutical compositions, comprising an isotonic excipient prepared under sufficiently sterile conditions for administration to a mammalian subject, particularly to a human being. In certain embodiments, multiple cycles of treatment may be administered by repeatedly applying the compositions to the site of injury, wound or defect for a time period sufficient to effect at least a partial healing of the injury, wound or defect, or, preferably, for a time period sufficient to effect a complete healing of the injury, wound or defect.

EXAMPLES

The following examples are put forth so as to provide those of ordinary skill in the art with a complete disclosure and description of how to make and use the present invention. The examples are offered for illustrative purposes only, and are not intended to limit the scope of what the inventors regard as their invention.

Reasonable efforts have been made to ensure accuracy with respect to numbers used, e.g. in the context of temperature, amount and such, but some experimental errors and deviations should be accounted for. Unless indicated otherwise, parts are parts by weight, molecular weight is average molecular weight, temperature is in degree Celsius, and pressure is at or near atmospheric. Standard abbreviations may be used throughout the specification, e.g. s or sec for second(s), min for minute(s), h or hr for hour(s), aa for amino acid(s), nt for nucleotide(s), kb for kilobase(s), i.v. for intravenous(ly), and the like.

Example 1

Supramolecular Guest-Host Hyaluronic Acid Hydrogels for Epithelial Cell Delivery to the Cornea Purpose: Restoration of a severely damaged corneal surface requires proper delivery and transplantation of cultured human epithelial cells. Here we investigated the feasibility of a supramolecular host-guest hydrogel assembly as a vehicle to deliver and engraft human epithelial cells to the cornea after total epithelial debridement. The goal is to determine whether the supramolecular gel provides a suitable environment for epithelial cell adhesion and proliferation on the cornea.

Methods: Hyaluronic acid (HA) was conjugated with cyclodextrin (CD) or adamantane (Ad). To form the supramolecular hydrogel, human corneal epithelial cells were first mixed with HA-CD and then mixed with HA-Ad in a 1:1 ratio of HA-CD to HA-Ad. To investigate hydrogel cytocompatibility, cells were seeded on the hydrogel and a live dead assay was performed at 4 and 10 days. Total epithelial debridement was performed on ex vivo rabbit corneas and then the gel and encapsulated cells were applied to the damaged corneas. At day 4, the corneas were fixed with PFA 4%, permeabilized and blocked with triton-x 0.5% and goat serum 5%, respectively. The tissue was incubated in anti-human nuclei antibody overnight to assess for the presence and adhesion of human epithelial cells to the cornea. Next, a secondary antibody anti-mouse Alexa 546 and DAPI were added and to the corneas and analyzed under confocal microscopy. Damaged corneas that received the encapsulated cells were compared to the corneas without encapsulated cells.

Results: The supramolecular hydrogel was cytocompatible showing very few dead cells after 4 and 10 days. After 4 days, the presence of human epithelial cells on the damaged cornea was confirmed by the anti-human nuclei antibody, suggesting that the encapsulated cells were able to adhere and spread on the corneas that underwent total epithelial debridement, including the central cornea. There was no growth of host (rabbit) epithelial cells on the central cornea of the no treatment group.

Conclusions: Supramolecular hyaluronic acid host-guest hydrogels may be useful as a vehicle to delivered cultured epithelial cells to the cornea.

Example 2

Encapsulation of Corneal Stromal Stem Cells within Supramolecular Host-Guest Hyaluronic Acid Gels Purpose: Corneal stromal stem cells (CSSCs) have shown promise in the treatment of corneal injury and scarring. However, the optimum way to deliver them to the cornea has yet to be determined, and their phenotypic expression in vitro remains an important area of study. Here, we investigate whether a supramolecular host-guest hyaluronic acid (HA) gel may serve as a suitable microenvironment for the culture and delivery of CSSCs based on their growth factor secretions and wound healing effects.

Methods: Live-dead analysis was used to track cell the viability and proliferation of CSSCs within the HA hostguest gel after the passage through a 23 g needle. The presence of TGF-beta, TSG-6, FGF-2, keratinocyte growth factor (KGF), and hepatocyte growth factor (HGF) were analyzed using reverse transcription polymerase chain reaction. To track the effects of the HA host-guest gel with and without CSSCs on corneal wound healing, a rabbit cornea organ culture keratectomy model was performed, where deep stromal wounds were filled with the HAhost guest gel with and without encapsulated CSSCs.

Results: CSSC viability within the HA host-guest gel was found to be over 90%. Growth factor expression was significantly higher in CSSCs grown in the HA host-guest matrix compared to CSSCs grown in a commercial medium on standard 2D culture plates. Human CSSCs within the HA gels remained viable with keratectomy wound sites and enhanced epithelial healing in organ culture compared to either HA host-guest gels alone or no treatment controls. HA host-guest gels alone also improved the rate of epithelialization compared to no treatment controls.

Conclusions: Supramolecular host-guest HA gels show promise as a material to promote corneal wound healing on its own, and as a cytocompatible microenvironment for the culture and delivery of CSSCs that stimulates the production of key growth factors and enhances epithelial wound healing in an organ culture.

Example 3

Recent efforts to develop hydrogel biomaterials have focused on better recapitulating the dynamic properties of the native extracellular matrix. In hydrogel biomaterials, binding thermodynamics and crosslink kinetics directly affect numerous bulk dynamic properties such as strength, stress relaxation, and material clearance. However, despite the broad range of bulk dynamic properties observed in biological tissues, present strategies to incorporate dynamic linkages in cell-encapsulating hydrogels rely on a relatively small number of dynamic covalent chemical reactions and host-guest interactions. To expand this toolkit, we report the preparation of supramolecular gelatin hydrogels with cucurbit[8]uril (CB[8])-based crosslinks that form on demand via thiol-ene reactions between preassembled CB[8]·FGGC peptide ternary complexes and grafted norbornenes. Human fibroblast cells encapsulated within these optically transparent, shear thinning, injectable hydrogels remained highly viable and exhibited a well-spread morphology in culture. These CB[8]-based gelatin hydrogels are useful in applications ranging from bioprinting to cell and drug delivery.

To expand the toolkit of host-guest interactions for use in cell-encapsulating hydrogels, we developed gelatin hydrogels that crosslink through cucurbit[8]uril (CB[8]) homoternary complexes formed by simultaneous inclusion of two guest molecules in one CB[8] cavitand. Cucurbit[n]urils are rigid, symmetric cavitands composed of n methylene-linked glycouril oligomers that form a hydrophobic cavity laced with ureido-carbonyl oxygens possessing very high quadrupole moments. Due to a combination of hydrophobic and ion-dipole interactions, CB[8] ternary complexes are highly selective with very high association rates and binding equilibrium constants (up to $10^{14}$ $M^{-2}$ under idealized conditions). CB[8] ternary complexes have previously been used to form synthetic and polysaccharide hydrogels for drug delivery and cell injection vehicle applications. However, previously reported CB[8]-based hydrogel materials are not suitable for long-term cell culture due to their slow gelation and short retention times, as well as the lack of cell-adhesive domains within the utilized polymer backbones. In this work, light-initiated thiol-ene reactions between preassembled CB[8]·FGGC peptide ternary complexes and grafted norbornenes were used to rapidly crosslink the cell-adhesive biopolymer gelatin into a supramolecular hydrogel, overcoming the limitations of prior systems to yield stable hydrogels that promote the uniform distribution, viability, and spreading of encapsulated human fibroblasts over seven days in culture. Notably, while light is used here to form the network, the gel is then injectable, shear-thinning, and self-healing—and thus can be applied directly from a syringe to another site. For therapeutic applications, this means that the gel can be administered from a syringe to, for example, a wound site without the need for any additional trigger such as light, heat, or chemical catalyst that may adversely affect surrounding tissue.

While hydrogel networks can form when CB[8] cavitands are added to aqueous solutions of guest-functionalized polymers with mechanical agitation, gelation kinetics are typically on the order of hours due to the relatively low aqueous solubility of CB[8] (<0.01 mM in water), which serves as a rate-limiting step for crosslink formation. In situ photopolymerization of vinyl monomers and vinyl-functionalized guest groups pre-complexed with CB[8] partially overcomes this solubility limitation by increasing the solubility of CB[8] in the precursor solution, enabling higher CB[8] loading and supramolecular crosslink density. However, the in situ polymerization approach still relies on continuous stirring to inhibit CB[8] precipitation and maintain network homogeneity, and reported photoreaction times range from 30 minutes to six hours under oxygen-depleted conditions. Here we develop a three-step gelation approach to exploit the enhanced aqueous solubility of CB[8] ternary complexes relative to uncomplexed CB[8] while enabling homogeneous, user-triggered gelation under cell-compatible conditions (FIG. 10).

First, FGGC peptides with an N-terminal phenylalanine and a C-terminal cysteine are pre-complexed with CB[8] in HEPES buffered physiological saline (FIG. 10A). N-terminally charged phenylalanines can form 2:1 complexes with CB[8] with exceptionally high equilibrium binding affinities (up to $10^{11}$ $M^{-2}$), and FGG has previously been utilized as a guest group in hydrogels crosslinked by CB[8] homoternary complexes. Second, norbornene-functionalized gelatin (GelNB) prepared according to a modified literature protocol (FIGS. 10B, 15, 16) is added to the mixture and fully dissolved at 37° C. Gelatin is an abundant biopolymer derived from denatured collagen that is commonly used in 3D cell culture applications due to its high water solubility and biocompatibility, intrinsic bioactivity, and biodegradability. The addition of GelNB up to at least 10% w/v does not induce CB[8] precipitation or phase separation. Moreover, the solution containing GelNB and preassembled CB[8]·FGGC peptide ternary complexes exhibits low viscosity at 37° C., permitting facile homogenous incorporation of therapeutic drug and cell cargo. Third, gelation is rapidly triggered by adding the water soluble, cytocompatible photoinitiator lithium phenyl-2,4,6-trimethylbenzoylphosphinate (LAP) to the solution, equilibrating to room temperature, and exposing the mixture to 365 nm light (FIG. 10C)—cytocompatible conditions similar to those previously reported for several different cell-encapsulating hydrogel systems, where complete gelation was observed in 10 minutes (the exposure time used here) or less.

Upon light exposure, thiol-norbornene step-growth photoreactions between the C-terminal cysteines in the preassembled CB[8]·FGGC peptide ternary complexes and the pendant norbornene groups on the gelatin backbone form supramolecular crosslinks between gelatin chains. Although no free thiol was detected in type A gelatin from porcine skin or gelatin-norbornene using Ellman's assay (detection limit:

0.25 mM or 6.25 μmol per g gelatin) (FIG. 17, Table 1), consistent with previous reports, some covalent bonds may also form upon light exposure, complementing CB[8]-based crosslinks, gelatin physical interactions, and additional entanglements introduced by peptide branch points to yield mechanically robust hydrogels that are stable at physiological temperature in serum-containing cell culture medium for at least one week. In contrast to other reported thiol-based crosslinking chemistries (e.g., thiol-vinylsulfone, thiol-maleimide, and thiol-methylsulfone), which either occur rapidly upon component mixing or require addition of a base catalyst that reduces cucurbit solubility and binding affinity, thiol-norbornene photoreactions occur on demand without inducing CB[8] precipitation, enabling homogenous CB[8] homoternary complex distribution prior to peptide grafting. Moreover, unlike the random chain-growth polymerization chemistries previously exploited to prepare CB[8]-based hydrogels, as well as gelatin-polyacrylate hybrid hydrogels with supramolecular crosslinks between naturally occurring gelatin aromatic amino acids and pendant cyclodextrins on the in situ polymerized polyacrylate backbone, thiol-norbornene photoreactions are not oxygen inhibited, require relatively low radical concentrations, produce single polymer hydrogel networks, and present a reduced risk of radical-mediated damage for sensitive cell types.

The measured absorbance for unmodified type A gelatin from porcine skin and gelatin-norbornene at concentrations ranging from 10 mg/mL to 40 mg/mL did not vary substantially, indicating the free thiol content was less than the assay detection limit.

TABLE 1

| Concentration (mg/mL) | Absorbance (AU) |
|---|---|
| Type A gelatin from porcine skin | |
| 10 | 0.0748 ± 0.0048 |
| 20 | 0.0793 ± 0.0018 |
| 40 | 0.0799 ± 0.0016 |
| Gelatin-norbornene | |
| 10 | 0.0764 ± 0.0051 |
| 20 | 0.0748 ± 0.0039 |
| 40 | 0.0808 ± 0.0039 |

The aromatic amino acid phenylalanine is naturally present in gelatin. Although supramolecular affinity for CB[n] cavitands is considerably lower for midchain aromatic amino acids relative to N-terminal amino acids because midchain residues lack N-terminal ammonium groups capable of interacting with the carbonyls on the CB[n] portal, we performed inverted vial tests at 37° C. to confirm that mixing CB[8] with gelatin or gelNB alone did not produce a temperature stable hydrogel (FIG. 11A). Additionally, inverted vial tests at 37° C. validated that gelatin and gelNB do not form temperature stable hydrogels and that gelNB mixed with preassembled CB[8]·FGGC peptide ternary complexes yields a low viscosity liquid prior to light exposure (FIG. 11A). Further, the reduced turbidity observed when gelNB is mixed with preassembled CB[8]·FGGC peptide ternary complexes instead of uncomplexed CB[8] indicates that preassembly increases CB[8] solubility as anticipated. Adding photoinitiator and exposing the mixture of gelNB and preassembled CB[8]·FGGC peptide ternary complexes to low dose UV light for 10 minutes produced a temperature stable hydrogel based on an inverted vial test at 37° C. (FIG. 11B).

The frequency and strain dependent mechanical properties of 9% w/v supramolecular gelatin hydrogels containing approximately 3.9 mM CB[8] and 7.7 mM FGGC peptide (1 mol CB[8] per 2 mol FGGC peptide), 30% theoretical modification of gelatin lysine residues) were observed at 37° C. using oscillatory shear rheology (FIGS. 11C, 11D). Supramolecular hydrogels are promising materials for applications involving injection or extrusion because they exhibit frequency-dependent mechanical properties, flow under applied shear, and reform rapidly upon cessation of shear. As expected, the storage (G') and loss (G") moduli of the gels varied with frequency, with the hydrogels acting as viscoelastic solids (G'>G") over the investigated frequency range (0.1 Hz to 10 Hz at 1% strain). The storage modulus of the supramolecular hydrogels at 37° C. could be tuned from about 200 Pa to about 400 Pa by altering either the gelNB weight percentage or the supramolecular crosslink density in the gels, while still maintaining shear thinning behavior in a dynamic frequency sweep (FIGS. 11C-E, 18, 19). Soft supramolecular hydrogels with comparable storage moduli have proven useful in a range of tissue engineering and drug delivery applications, including neural cell expansion, controlled growth factor release, and hard tissue regeneration. 9% w/v supramolecular gelatin hydrogels with storage moduli of approximately 200 Pa at 37° C. were used in further studies to characterize the CB[8]-based hydrogels.

The shear-thinning and self-healing capabilities of the supramolecular gelatin hydrogels at 37° C. were confirmed using oscillatory shear rheology over multiple rounds of strain cycling (sequential shear with 0.1% strain for 120 s followed by 1000% strain for 60 s) (FIG. 11E). The hydrogels' ability to dissipate stress under applied strain was also examined. As expected, the supramolecular gelatin hydrogels were able to rapidly reorganize crosslinks, fully relaxing to dissipate stress in under 100 s (FIG. 11F). To assess utility for applications involving injection or extrusion, an injection study was performed using a supramolecular gelatin hydrogel gelled inside a 1 mL disposable plastic syringe and then equilibrated to 37° C. The warm gel could be injected through an 18G needle into a mold and rapidly reformed on a 37° C. Peltier plate (FIG. 12A). Furthermore, human fetal lung fibroblasts (MRC-5) encapsulated in a CB[8]-based hydrogel and then injected through an 18G needle in the gelled state remained homogenously distributed and highly viable, with greater than 94% viability observed 24 hours post-injection (FIG. 12B). This rapid injection molding behavior makes supramolecular gelatin hydrogels attractive materials for bioprinting and cell transplantation applications in which uniform cargo distribution and precise control over material placement are highly desirable.

Poor light transmittance can impede observation of encapsulated cell morphology and behavior during 3D cell culture. Previously reported CB[8] hydrogels commonly used 1:1:1 heteroternary complexes to form crosslinks through simultaneous inclusion of one electron-rich guest and one electron-poor guest in the CB[8] cavitand. However, the resulting hydrogels are highly colored due to the formation of charge-transfer complexes between the guest groups, and uncapped charged guest groups (e.g., methyl viologen) raise cytotoxicity concerns in long-term cell culture applications. FGGC guest groups, which do not undergo charge transfer when complexed with CB[8], were selected in part to promote light transmittance through the hydrogels and to minimize interference during fluorescence imaging. Additionally, FGGC peptides composed of natural amino acids were expected to be biocompatible in both the capped and uncapped state. Further, in contrast to previous CB[8]-based hydrogels prepared using the physiological medium phosphate buffered saline (PBS), we used HEPES buffered saline to dissolve the hydrogel components. Similar to previous reports, dissolving the hydrogel components in PBS produced turbid gels, likely due to charge and ionic screening interactions associated with the phosphate anions. Using the cell-compatible zwitterion HEPES as a buffering agent instead of phosphate yielded optically clear hydrogels when the gels were cast in a 0.5-mm thick mold (FIG. 13A).

To further characterize the optical properties of the supramolecular gelatin hydrogels, 100 μL of gel solution containing the photoinitiator LAP was pipetted into 96-well plates and exposed to 365 nm light for 10 minutes, resulting in gels with thicknesses of approximately 3 mm. Absorbance values were measured over the soft UV and visible light range (350 to 800 nm) using a SpectraMax M2 microplate reader and converted to transmittance through the Beer-Lambert Law, which assumes that poor light transmittance in the samples results from light scattering rather than absorbance (FIGS. 13B,C). Hydrogel samples were equilibrated at either ambient temperature or 37° C. prior to measuring absorbance at the same temperature. Transmittance in 1-mm thick hydrogels was estimated by assuming that gel thickness is approximately equal to the optical path length in the Beer-Lambert Law. Light transmittance properties appeared to be independent of temperature over the tested range. While thick hydrogels exhibited relatively poor light transmittance over the visible range (380 to 700 nm), with only 39.2±1.6% and 38.6±1.6% of visible light transmitted through the gels at ambient temperature and 37° C., respectively, hydrogels with a more representative thickness for in vitro studies (1 mm) are expected to have significantly improved light transmittance properties (>70%).

Figure 13D:
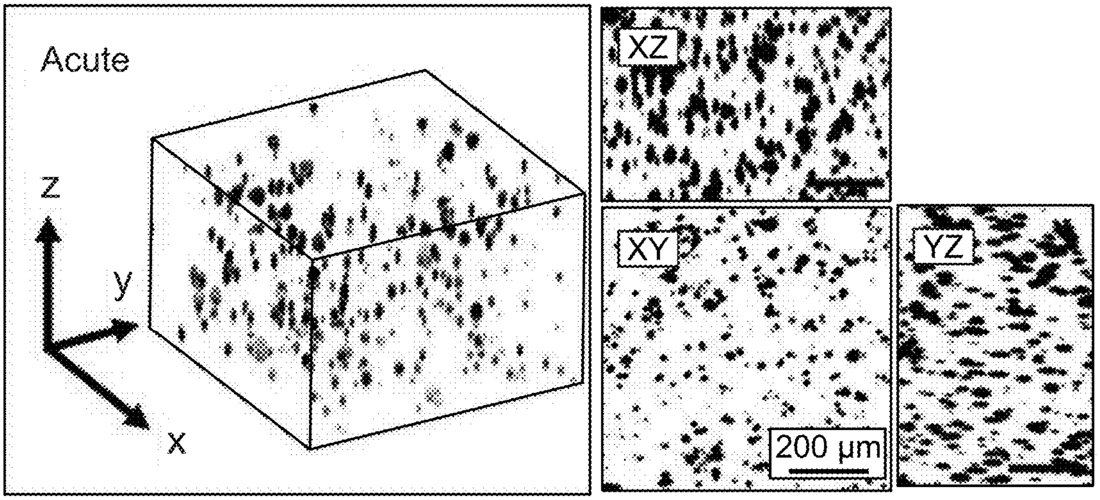
Figure 13E:
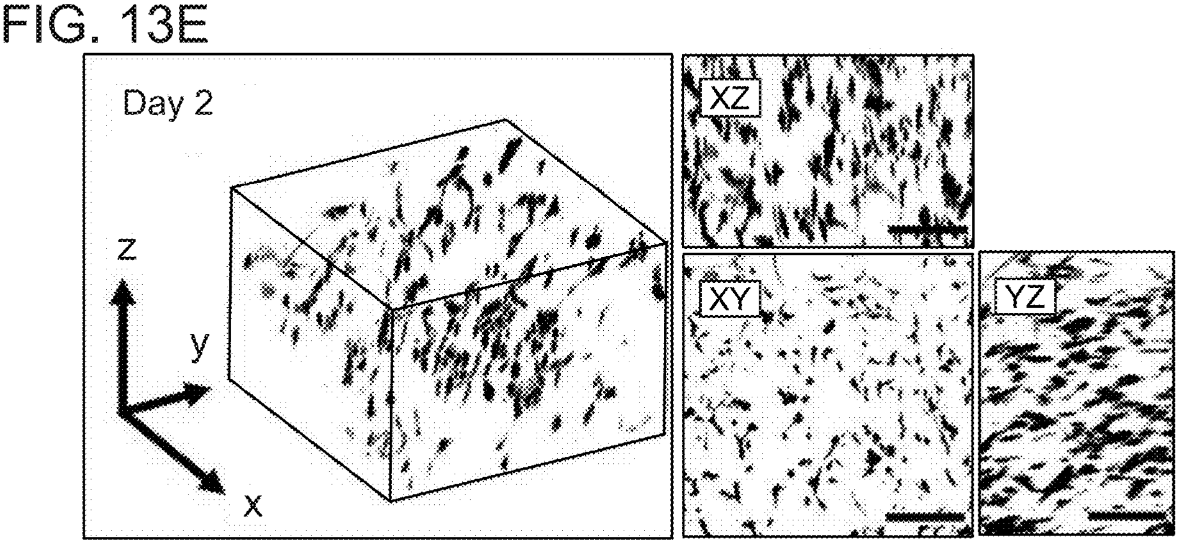
Figure 13F:
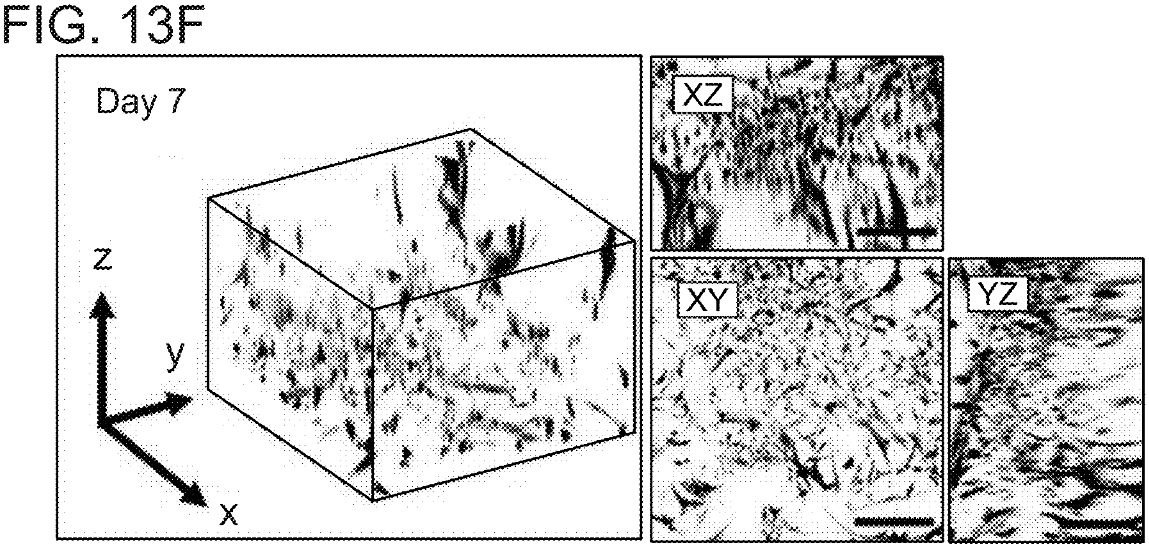

To confirm that the light transmittance properties of the hydrogels are sufficient for light microscopy observation of cell behavior during long-term 3D cell culture, we encapsulated human fetal lung fibroblast cells in supramolecular gelatin hydrogels. The cell-encapsulating hydrogels were immersed in serum-containing cell culture medium for up to one week prior to Live/Dead staining. 3D reconstruction of images obtained through confocal microscopy showed that viable MRC-5s could be observed in the hydrogels up to a Z-axis depth of approximately 500 μm (the upper bound on imaging depth for the microscope used) over seven days in culture (FIGS. 13D-F). Moreover, the 3D reconstructions confirmed that cells encapsulated in the supramolecular gelatin hydrogels did not settle prior to the onset of gelation and remained homogenously distributed for at least one week in culture.

Figure 14A:
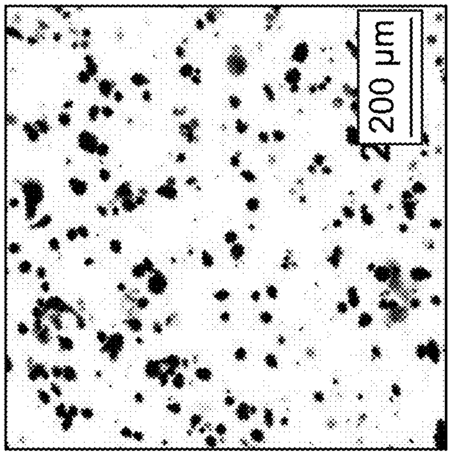
Figure 14B:
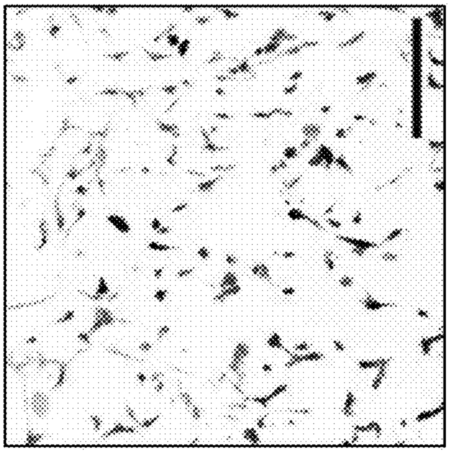
Figure 14C:
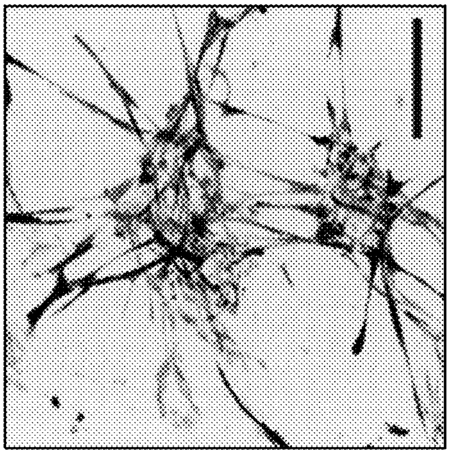
Figure 14D:
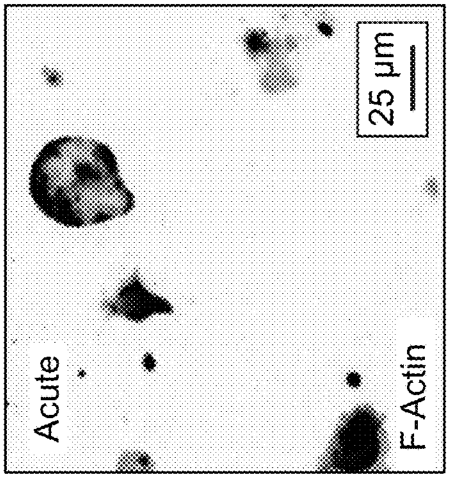
Figure 14E:
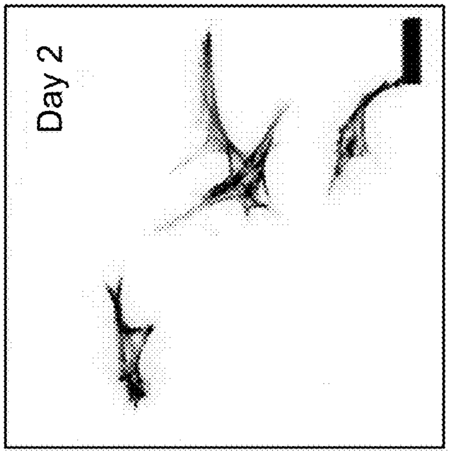
Figure 14F:
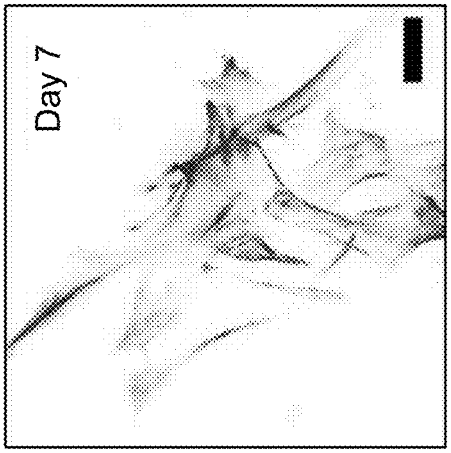

Acute viability following light exposure was quantified using a Live/Dead cytotoxicity assay to further establish that the thiol-ene photoreactions are not cytotoxic. Two hours post-encapsulation, the fibroblasts remained rounded but highly viable, with a live cell fraction of 88.7% (FIGS. 13D, 14A, 14D). To verify that the hydrogels support long-term culture of encapsulated cells, MRC-5 cells were cultured within the supramolecular gelatin hydrogels for an additional two to seven days. After two days in culture, the fibroblasts exhibited a well-spread morphology with distinct actin stress fibers (FIGS. 13E, 14B, 14E). After one week in culture, the fibroblasts remained highly viable, with a live cell fraction of 95.9%, and formed large cell clusters composed of spread cells with well-defined actin stress fibers (FIGS. 13F, 14C, 14F). While cell-free CB[8]-based hydrogels swelled approximately two-fold without degrading over the course of one week in serum-containing cell culture medium at physiological conditions (FIG. 20), cell density remained relatively constant during the culture period (FIG. 21A), indicating that the encapsulated fibroblasts proliferate in spite of the soft microenvironment (FIG. 21B). Future work will focus on tuning hydrogel swelling and retention properties through the use of tandem covalent and supramolecular crosslinks. Taken together, these results indicate that CB[8]-based supramolecular gelatin hydrogels prepared using light-initiated thiol-ene reactions are biocompatible and support long-term 3D cell culture.

We developed a CB[8]-mediated supramolecular gelatin hydrogel system that forms via user-triggered thiol-ene reactions between grafted norbornenes and preassembled CB[8]·FGGC peptide ternary complexes. In situ conjugation of the pre-assembled CB[8]-guest complexes to the gelatin backbone overcomes three major limitations of previous CB[8]-based hydrogels and supramolecular gelatin materials by eliminating the need for a second synthetic, chain-growth polymer network while still enabling rapid, on demand gelation and long-term cell culture. These CB[8]-based gelatin hydrogels exhibited favorable optical properties and were injectable in the gelled state via an 18G syringe needle. Moreover, human fibroblasts encapsulated in CB[8]-based gelatin hydrogels remained highly viable and uniformly distributed throughout the gels for seven days in culture. CB[8]-mediated supramolecular gelatin hydrogels represent a promising new material for use in bioprinting, cell transplantation, and fundamental studies of cell-matrix interactions.

Experimental Procedures

Materials. Reagents were purchased from MilliporeSigma or Fisher Scientific and used without further purification unless otherwise noted.

Synthesis and characterization of gelatin-norbornene. Gelatin-norbornene (GelNB) was prepared according to a modified literature protocol. Briefly, about 2.5 g (~10% w/v) of type A gelatin from porcine skin (Sigma G1890) was dissolved in 25 mL 1×PBS, pH 7.4 (Fisher 10010001) at approximately 50° C. under constant stirring. Approximately 5 g (~20% w/v) of carbic anhydride (Sigma 247634) was added to the gelatin solution. The pH value of the solution was then adjusted using sodium hydroxide solution to approximately pH 8.0, at which point the carbic anhydride appeared to dissolve completely and a clear reaction mixture was obtained. The reaction was allowed to proceed overnight. The reaction was then quenched by adding 125 mL warm 1×PBS, pH 7.4 (~37° C.). The diluted GelNB solution was dialyzed in Milli-Q water at ~37° C. for 3 days (Spectrum™ Spectra/Por™ 7 Membrane Tubing, MWCO: 2 kDa) and lyophilized to obtain dry product.

Functionalization of type A gelatin with norbornene was confirmed by $^1$H-NMR (FIG. 15). Conjugation efficacy was estimated using a fluorescamine-based assay following a modified literature protocol (FIG. 16). Briefly, fluorescamine (Sigma F9015) was dissolved in DMSO to a concentration of 3 mg/mL and then 25 μL of the fluorescamine solution was added to 75 μL of modified gelatin. After incubating the mixture for 30 minutes at room temperature, the fluorescence intensity (Ex/Em=380 nm/470 nm) was measured using a SpectraMax M2 Microplate Reader. Measurements were conducted in duplicate. Conjugation efficiency was then evaluated based on the concentration calculated from the standard curve of an unmodified gelatin solution. Briefly, the fluorescence intensities of gelatin solutions from 80 to 2500 μg/mL were measured according to the above procedure; the intensity measurements showed a linear correlation with gelatin concentration. From the linear standard curve, the lysine concentration of gelatin-norbornene was estimated based on the measured intensity and the degree of modification was determined.

The free thiol content of unmodified type A gelatin from porcine skin and gelatin-norbornene was measured using Ellman's assay according to modified manufacturer's instructions. Briefly, Ellman's reagent (TCI America D09441G) was dissolved in 0.1 M sodium phosphate, pH 8.0 containing 0.5 mM EDTA to a concentration of 4 mg/mL. 20 μL of Ellman's reaction solution and 100 μL of cysteine standard (1.5 mM, 1.25 mM, 1.0 mM, 0.75 mM, 0.5 mM, 0.25 mM, 0 mM), type A gelatin (40 mg/mL, 20 mg/mL, 10 mg/mL), or gelatin-norbornene (40 mg/mL, 20 mg/mL, 10 mg/mL) in 1×PBS, pH 7.4 were added to Eppendorf tubes containing 1 mL 1×PBS, mixed, and incubated in the dark at room temperature for 15 minutes. 3 replicates were prepared per condition. After aliquoting 100 μL of each sample into a 96-well plate, the absorbance intensity was measured at 412 nm.

General procedure for preparing CB[8]-based supramolecular gelatin hydrogels. Cucurbit[8]uril hydrate (Sigma 545228) and FGGC peptide (GenScript, approximately 95% purity) were added to Live Cell Imaging Solution (Invitrogen A14291DJ), a HEPES buffered physiological saline, to the desired concentration, briefly sonicated (<5 minutes) in an ultrasonic bath sonicator, and mixed with continuous stirring at 37 C until homogenously distributed (~30 minutes). GelNB was then added to the desired concentration and mixed with continuous stirring until all components were fully dissolved and homogenous (about 2 to 3 hours). 10× (33.3 mM) stock solution of lithium phenyl-2,4,6-trimethylbenzoylphosphinate (LAP) photoinitiator (Allevi) in Live Cell Imaging Solution was added immediately prior to light exposure. The precursor solution was transferred into custom cylindrical silicone molds prepared from 0.5 mm thick silicone insulator (Electron Microscopy Sciences 70338-10), glass vials, or 8-well glass chamber slides as desired. Pipet tips, glass vials, and Eppendorf tubes used to handle precursor solutions were kept warm (~37° C.) to avoid viscosity changes during handling. The precursor solution with photoinitiator was allowed to cool to room temperature and then exposed to 365 nm UV light (<5 mW/cm$^2$; UVLMS-38 EL Series 3-UV lamp, 8-W) for ten minutes.

Here, where we refer to degree of theoretical lysine modification in a hydrogel material to characterize the supramolecular crosslink density, the percentage was calculated by assuming type A gelatin possesses 2.86 mmol lysine per 10 g. Accordingly, for 0.1 g gelatin, 0.0286 mmol of FGGC peptide would be theoretically required to modify 100% of the lysine residues on the gelatin backbone. Notably, the maximum degree of modification is limited by the degree of lysine modification with norbornene reactive handles, which we estimated at 67.8% using a fluorescamine-based assay as described above.

Illustratively, to prepare 1 mL of 9% w/v supramolecular gelatin hydrogel with 30% theoretical lysine modification, 3.27 mg FGGC peptide and 6.8 mg CB[8] (0.5 eq., adjusted to account for reported water content) were dissolved in 1 mL Live Cell Imaging Solution as described above. Both components were dissolved at 1.11× the final desired concentration to account for later dilution with 10×LAP stock. 100 mg of GelNB was then added. After all hydrogel precursors were homogenously dissolved, 900 μL of the precursor solution was mixed with 100 μL of 10×LAP stock in a pre-warmed Eppendorf tube. The resulting solution was permitted to cool to room temperature and then exposed to 365 nm light for 10 minutes.

Figure 18A:
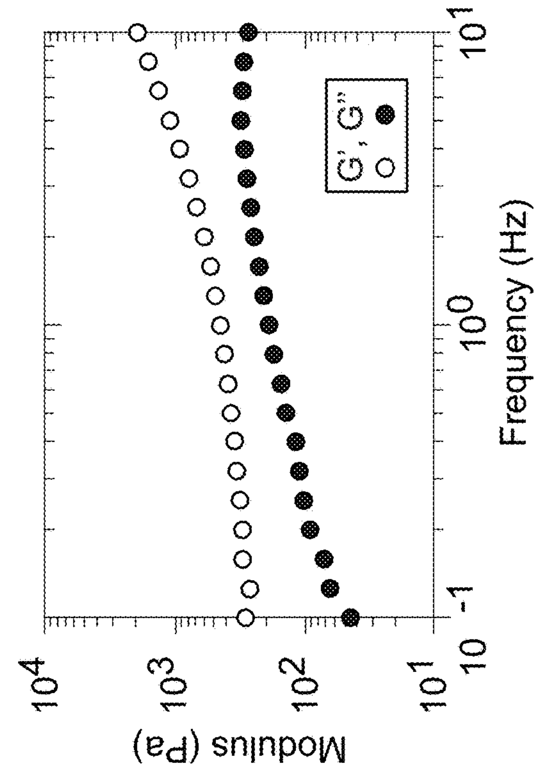
Figure 18B:
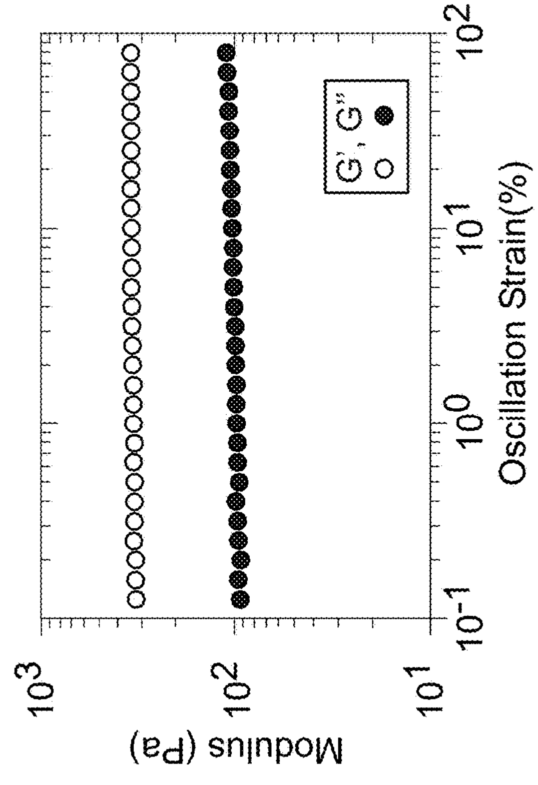
Figure 18C:
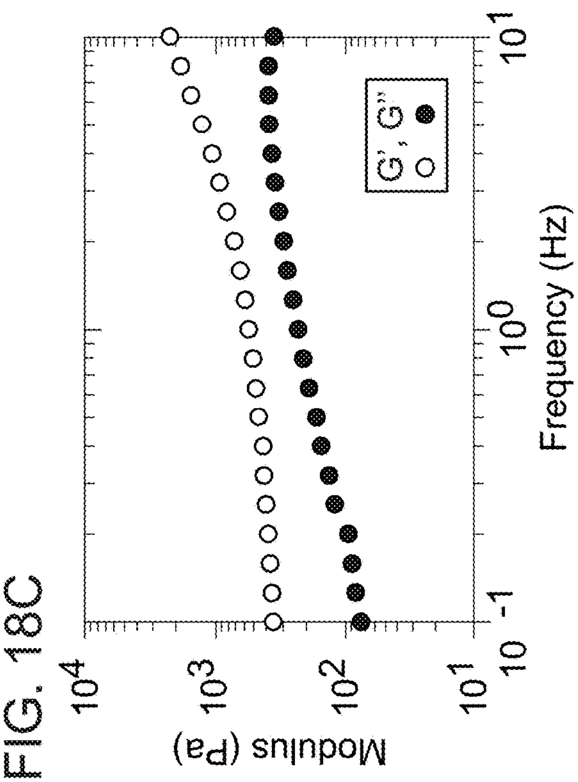
Figure 18D:
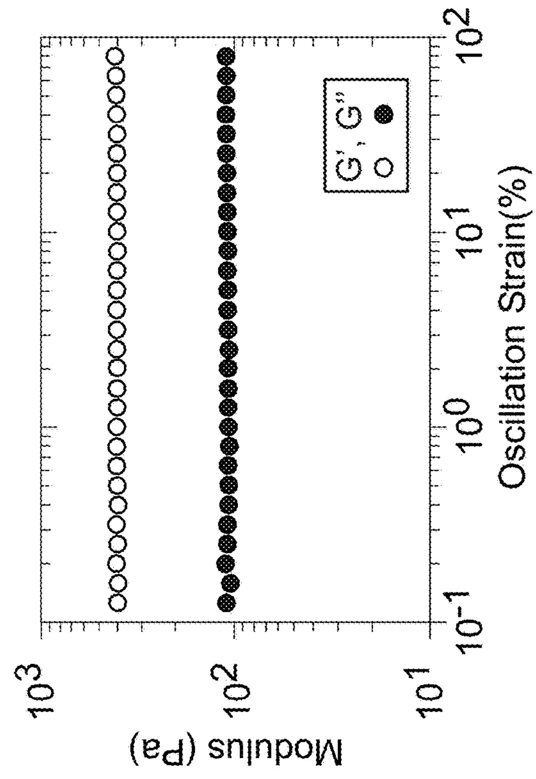

Rheological characterization of the hydrogels. Rheological characterization was performed using a TA Instruments Discovery HR-2 rheometer fitted with an 8 mm parallel plate geometry. For mechanical characterization, hydrogels were pre-formed according to the general procedure above in custom cylindrical silicone molds and equilibrated in 1×PBS, pH 7.4 at ~37° C. Frequency and strain sweeps were conducted for each sample to ensure the probing conditions were within the linear viscoelastic region of the sample. To characterize storage moduli, the hydrogels were subjected to a frequency sweep from 0.1 to 10 Hz at fixed 1% strain (9% w/v gelatin hydrogels with 30% theoretical lysine modification) or 0.1% strain (6% w/v and 8% w/v gelatin hydrogels with 50% theoretical lysine modification) (FIGS. 11C and 18A,C). Storage moduli were reported for a frequency of 0.2 Hz and 0.1% strain for 6% w/v and 8% w/v gelatin hydrogels with 50% theoretical lysine modification; for 9% w/v gelatin hydrogels with 30% theoretical lysine modification, storage moduli were reported as an average of the measured storage moduli for frequencies around 0.2 Hz at 1% strain (FIG. 19B). The stress relaxation modulus was measured at 2% strain amplitude.

For the shear-thinning test, samples underwent sequential shear with strain of 0.1% (for 120 s) and 1000% (for 60 s) for multiple cycles, and the recovery of the storage (G') and loss moduli (G") were monitored by time sweeps at fixed angular frequency (10 rad/s).

Hydrogel degradation study. Mass swelling ratio and dry mass were measured using a modified literature protocol. Briefly, hydrogels (75 μL) were cast into pre-weighed microcentrifuge tubes and exposed to 365 nm light for 10 minutes. High glucose DMEM supplemented with 10% fetal bovine serum (FBS), 2 mM L-glutamine, and 1% penicillin/streptomycin (1 mL) was added to the microcentrifuge tubes, which were maintained at 37° C. At each time point, cell culture media was carefully aspirated and excess media wicked away with a Kimwipe prior to measuring the hydrogel wet mass. After measuring the wet mass, the samples were frozen at −80° C. and lyophilized. The dry mass of the hydrogels was measured following lyophilization. Mass loss was determined from the hydrogel dry mass measurements, and hydrogel mass swelling ratios were calculated by dividing the wet mass by the corresponding dry mass for each hydrogel. Time points were collected at 2 h, 2 days, and 7 days.

Light transmittance measurements. To characterize the light transmittance properties of the hydrogels, warm gel solution (~37° C.) containing the photoinitiator LAP was pipetted into 96-well plates (100 μL/well), cooled to room temperature and exposed to 365 nm light for 10 minutes, resulting in gels with thicknesses of approximately 3 mm. Absorbance values were measured over the soft UV and visible light range (350 to 800 nm) using a SpectraMax M2 microplate reader and converted to transmittance through the Beer-Lambert Law. Hydrogel samples were equilibrated at either ambient temperature or 37° C. prior to measuring absorbance at the same temperature. Three samples were prepared for each group. Transmittance in 1-mm thick hydrogels was estimated by assuming that gel thickness is approximately equal to the optical path length in the Beer-Lambert Law.

Human fetal lung fibroblast (MRC-5) culture. Human fetal lung fibroblasts (MRC-5) were purchased from ATCC (CCL-171). MRC-5s were cultured in high glucose DMEM supplemented with 10% fetal bovine serum (FBS), 2 mM L-glutamine, and 1% penicillin/streptomycin. To generate the stable reporter cell line, the MRC-5s were first immortalized by retroviral transduction to constitutively express human telomerase (hTert). A subset of the cells was subsequently lentivirally transduced to express the fluorescent actin reporter (LifeAct-mTagBFP2; Addgene #101893) under control of the CMV promoter and selected for puromycin resistance. pLenti Lifeact-mTagBFP2 PuroR was deposited in the Addgene repository by Ghassan Mouneimne (http://n2t.net/addgene:101893). Both retrovirus and lentivirus were produced by transfecting HEK 293T cells (ATCC CRL-3216) with packaging plasmids complexed with Fugene6 (Promega) in Opti-MEM. Viruses were harvested by collecting culture supernatant 48 h post-transfection, filtered (0.45 μm), and mixed in a 1:2 ratio with fresh MRC-5 maintenance medium for viral transduction. Cells were passaged after reaching 90% confluency using 0.05% Trypsin-EDTA.

Cell encapsulation in hydrogels. After trypsinization, MRC-5 cells expressing a blue fluorescent protein (BFP) reporter (LifeAct-mTagBFP2) were resuspended to a concentration of $1\times10^6$ cells/mL in warm hydrogel precursor solution (9% w/v gelatin-norbornene, 3.9 mM CB[8], 7.7 mM FGGC peptide, 3.33 mM LAP photoinitiator in Live Cell Imaging Solution). Warm precursor solution with suspended MRC-5s was dispensed into 8-well chamber slides (100 μL/well). After equilibrating to room temperature, the wells were exposed to 365 nm light (<5 $mW/cm^2$) for 10 minutes. The wells were then filled with warm cell culture medium (FluoroBrite DMEM (Fisher A1896701) supplemented with 10% FBS, 2 mM L-glutamine, and 1% penicillin/streptomycin) and maintained in a 37° C., 5% $CO_2$ incubator. Half media changes were performed daily.

Viability following injection study. After trypsinization, MRC-5 cells were resuspended to a concentration of $1\times10^6$ cells/mL in warm hydrogel precursor solution (9% w/v gelatin-norbornene, 3.9 mM CB[8], 7.7 mM FGGC peptide, 3.33 mM LAP photoinitiator in Live Cell Imaging Solution). Warm precursor solution with suspended MRC-5s was sucked up into a 1 mL syringe. After equilibrating to room temperature, the syringe was exposed to 365 nm light (<5 $mW/cm^2$) for 10 minutes. The syringe was equilibrated to 37° C. and then hydrogels were injected at 37° C. into 8-well chamber slides. Well containing hydrogels were filled with warm cell culture medium (FluoroBrite DMEM (Fisher A1896701) supplemented with 10% FBS, 2 mM L-glutamine, and 1% penicillin/streptomycin) and maintained in a 37° C., 5% $CO_2$ incubator.

Characterization of encapsulated cell viability and morphology. The viability and morphology of fibroblasts encapsulated in the hydrogels was assessed 2 h, 2 days, and 7 days after encapsulation. At each time point, gels were stained with Live/Dead reagents (Thermo Fisher Scientific) diluted into unsupplemented FluoroBrite DMEM medium (1:2000 dilution for calcein-AM, 1:500 for ethidium homodimer) after washing once with 1×PBS, pH 7.4. After incubating in the dye solution for 30 minutes at 37° C., the gels were washed once with 1×PBS, pH 7.4. Wells were then filled with warm cell culture medium, and the gels were imaged on a Leica SPE confocal microscope. Images were processed using ImageJ software (NIH).

REFERENCES

1. Tibbitt, M. W.; Anseth, K. S. Hydrogels as extracellular matrix mimics for 3D cell culture. Biotechnol. Bioeng. 2009, 103, 655-663.
2. Lee, K. Y.; Mooney, D. J. Hydrogels for Tissue EngineeringSupramolecular guest-host hyaluronic acid hydrogels for epithelial cell delivery to the cornea. Chem. Rev. 2001, 101, 1869-1880.
3. Ratner, B. D.; Bryant, S. J. Biomaterials: where we have been and where we are going. Annu. Rev. Biomed. Eng. 2004, 6, 41-75.
4. Wang, H.; Heilshorn, S. C. Adaptable Hydrogel Networks with Reversible Linkages for Tissue Engineering. Adv. Mater. 2015, 27, 3717-3736.
5. Webber, M. J.; Appel, E. A.; Meijer, E. W.; Langer, R. Supramolecular biomaterials. Nat. Mater. 2016, 15, 13-26.
6. Rosales, A. M.; Anseth, K. S. The design of reversible hydrogels to capture extracellular matrix dynamics. Nat. Rev. Mater. 2016, 1, 1-15.
7. Zou, L.; Braegelman, A. S.; Webber, M. J. Dynamic Supramolecular Hydrogels Spanning an Unprecedented Range of Host-Guest Affinity. ACS Appl. Mater. Interfaces 2019, 11, 5695-5700.
8. Takashima, Y.; Sawa, Y.; Iwaso, K.; Nakahata, M.; Yamaguchi, H.; Harada, A. Supramolecular Materials Cross-Linked by Host-Guest Inclusion Complexes: The Effect of Side Chain Molecules on Mechanical Properties. Macromolecules 2017, 50, 3254-3261.
9. Chen, G.; Jiang, M. Cyclodextrin-based inclusion complexation bridging supramolecular chemistry and macromolecular self-assembly. Chem. Soc. Rev. 2011, 40, 2254-2266.
10. Connors, K. A. The Stability of Cyclodextrin Complexes in Solution. Chem. Rev. 1997, 97, 1325-1358.
11. Schneider, H.; Hacket, F.; Rudiger, V.; Ikeda, H. NMR Studies of Cyclodextrins and Cyclodextrin Complexes. Chem. Rev. 1998, 98, 1755-1786.
12. Eli, W.; Chen, W.; Xue, Q. The association of anionic surfactants with β-cyclodextrin. An isothermal titration calorimeter study. J. Chem. Thermodyn. 1999, 31, 1283-1296.
13. Charlot, A.; Heyraud, A.; Guenot, P.; Rinaudo, M.; Auzély-Velty, R. Controlled Synthesis and Inclusion Ability of a Hyaluronic Acid Derivative Bearing β-Cyclodextrin Molecules. Biomacromolecules 2006, 7, 907-913.
14. Wu, H.; Chen, H.; Tang, B.; Kang, Y.; Xu, J.; Zhang, X. Host-Guest Interactions between Oxaliplatin and Cucurbit[7]uril/Cucurbit[7]uril Derivatives under Pseudo-Physiological Conditions. Langmuir 2020, 36, 1235-1240.
15. Lagona, J.; Mukhopadhyay, P.; Chakrabarti, S.; Isaacs, L. The Cucurbit[n]uril Family. Angew. Chem. Int. Ed. 2005, 44, 4844-4870.
16. Rowland, M. J.; Appel, E. A.; Coulston, R. J.; Scherman, O. A. Dynamically crosslinked materials via recognition of amino acids by cucurbit[8]uril. J. Mater. Chem. B 2013, 1, 2904-2910.
17. Ding, Y.; Wei, J.; Li, S.; Pan, Y.; Wang, L.; Wang, R. Host-Guest Interactions Initiated Supramolecular Chitosan Nanogels for Selective Intracellular Drug Delivery. ACS Appl. Mater. Interfaces 2019, 11, 28665-28670.
18. Rowland, M. J.; Atgie, M.; Hoogland, D.; Scherman, O. A. Preparation and Supramolecular Recognition of Multivalent Peptide-Polysaccharide Conjugates by Cucurbit[8]uril in Hydrogel Formation. Biomacromolecules 2015, 16, 2436-2443.
19. Xu, W.; Song, Q.; Xu, J.; Serpe, M. J.; Zhang, X. Supramolecular Hydrogels Fabricated from Supramonomers: A Novel Wound Dressing Material. ACS Appl. Mater. Interfaces 2017, 9, 11368-11372.

20. Zou, L.; Su, B.; Addonizio, C. J.; Pramudya, I.; Webber, M. J. Temperature-Responsive Supramolecular Hydrogels by Ternary Complex Formation with Subsequent Photo-Cross-linking to Alter Network Dynamics. Biomacromolecules 2019, 20, 4512-4521.
21. Appel, E. A.; Loh, X. J.; Jones, S. T.; Biedermann, F.; Dreiss, C. A.; Scherman, O. A. Ultrahigh-Water-Content Supramolecular Hydrogels Exhibiting Multistimuli Responsiveness. J. Am. Chem. Soc. 2012, 134, 11767-11773.
22. Liu, J.; Tan, C. S. Y.; Lan, Y.; Scherman, O. A. Toward a versatile toolbox for cucurbit[n]uril-based supramolecular hydrogel networks through in situ polymerization. J. Polym. Sci. Pol. Chem. 2017, 55, 3105-3109.
23. Liu, J.; Tan, C. S. Y.; Yu, Z.; Li, N.; Abell, C.; Scherman, O. A. Tough Supramolecular Polymer Networks with Extreme Stretchability and Fast Room-Temperature Self-Healing. Adv. Mater. 2017, 29, 1605325.
24. Liu, J.; Tan, C. S. Y.; Yu, Z.; Lan, Y.; Abell, C.; Scherman, O. A. Biomimetic Supramolecular Polymer Networks Exhibiting both Toughness and Self-Recovery. Adv. Mater. 2017, 29, 1604951.
25. Mũnoz, Z.; Shih, H.; Lin, C. Gelatin hydrogels formed by orthogonal thiol-norbornene photochemistry for cell encapsulation. Biomater. Sci. 2014, 2, 1063-1072.
26. Jaipan, P.; Nguyen, A.; Narayan, R. J. Gelatin-based hydrogels for biomedical applications. MRS Communications 2017, 7, 416-426.
27. Kharkar, P. M.; Rehmann, M. S.; Skeens, K. M.; Maverakis, E.; Kloxin, A. M. Thiol-ene Click Hydrogels for Therapeutic Delivery. ACS Biomater. Sci. Eng. 2016, 2, 165-179.
28. Greene, T.; Lin, C. Modular Cross-Linking of Gelatin-Based Thiol-Norbornene Hydrogels for in Vitro 3D Culture of Hepatocellular Carcinoma Cells. ACS Biomater. Sci. Eng. 2015, 1, 1314-1323.
29. Burdick, J. A.; Chung, C.; Jia, X.; Randolph, M. A.; Langer, R. Controlled Degradation and Mechanical Behavior of Photopolymerized Hyaluronic Acid Networks. Biomacromolecules 2005, 6, 386-391.
30. Fairbanks, B. D.; Schwartz, M. P.; Halevi, A. E.; Nuttelman, C. R.; Bowman, C. N.; Anseth, K. S. A Versatile Synthetic Extracellular Matrix Mimic via Thiol-Norbornene Photopolymerization. Adv. Mater. 2009, 21, 5005-5010.
31. Feng, Q.; Wei, K.; Lin, S.; Xu, Z.; Sun, Y.; Shi, P.; Li, G.; Bian, L. Mechanically resilient, injectable, and bioadhesive supramolecular gelatin hydrogels crosslinked by weak host-guest interactions assist cell infiltration and in situ tissue regeneration. Biomaterials 2016, 101, 217-228.
32. Loessner, D.; Meinert, C.; Kaemmerer, E.; Martine, L. C.; Yue, K.; Levett, P. A.; Klein, T. J.; Melchels, F. P. W.; Khademhosseini, A.; Hutmacher, D. W. Functionalization, preparation and use of cell-laden gelatin methacryloyl-based hydrogels as modular tissue culture platforms. Nat. Protoc. 2016, 11, 727-746.
33. Hafidz, R.; Yaakob, C. M.; Amin, I.; Noorfaizan, A. Chemical and functional properties of bovine and porcine skin gelatin. Int. Food Res. J. 2011, 18, 813-817.
34. Eastoe, J. E. The amino acid composition of mammalian collagen and gelatin. Biochem. J. 1955, 61, 589.
35. Nguyen, Q.; Fanous, M. A.; Kamm, L. H.; Khalili, A. D.; Schuepp, P. H.; Zarkadas, C. G. A comparison of the amino acid composition of two commercial porcine skins (rind). J. Agric. Food Chem. 1986, 34, 565-572.
36. Rebers, L.; Granse, T.; Tovar, G. E.; Southan, A.; Borchers, K. Physical interactions strengthen chemical gelatin methacryloyl gels. Gels 2019, 5, 4.
37. Abbasi, M.; Faust, L.; Wilhelm, M. Comb and Bottlebrush Polymers with Superior Rheological and Mechanical Properties. Adv. Mater. 2019, 31, 1806484.
38. Paez, J. I.; Farrukh, A.; Valbuena-Mendoza, R.; Włodarczyk-Biegun, M. K.; del Campo, A. Thiol-Methylsulfone-Based Hydrogels for 3D Cell Encapsulation. ACS Appl. Mater. Interfaces 2020, 12, 8062-8072.
39. Das, D.; Assaf, K. I.; Nau, W. M. Applications of Cucurbiturils in Medicinal Chemistry and Chemical Biology. Front. Chem. 2019, 7.
40. Feng, Q.; Xu, J.; Zhang, K.; Yao, H.; Zheng, N.; Zheng, L.; Wang, J.; Wei, K.; Xiao, X.; Qin, L.; Bian, L. Dynamic and Cell-Infiltratable Hydrogels as Injectable Carrier of Therapeutic Cells and Drugs for Treating Challenging Bone Defects. ACS Cent. Sci. 2019, 5, 440-450.
41. Lin, C.; Ki, C. S.; Shih, H. Thiol-norbornene photoclick hydrogels for tissue engineering applications. J. Appl. Polym. Sci. 2015, 132, 41563.
42. Hui, E.; Gimeno, K. I.; Guan, G.; Caliari, S. R. Spatiotemporal Control of Viscoelasticity in Phototunable Hyaluronic Acid Hydrogels. Biomacromolecules 2019, 20, 4126-4134.
43. Webber, M. J.; Appel, E. A.; Vinciguerra, B.; Cortinas, A. B.; Thapa, L. S.; Jhunjhunwala, S.; Isaacs, L.; Langer, R.; Anderson, D. G. Supramolecular PEGylation of biopharmaceuticals. Proc. Natl. Acad. Sci. U.S.A. 2016, 113, 14189-14194.
44. Appel, E. A.; Biedermann, F.; Rauwald, U.; Jones, S. T.; Zayed, J. M.; Scherman, O. A. Supramolecular Cross-Linked Networks via Host-Guest Complexation with Cucurbit[8]uril. J. Am. Chem. Soc. 2010, 132, 14251-14260.
45. Appel, E. A.; Forster, R. A.; Koutsioubas, A.; Toprakcioglu, C.; Scherman, O. A. Activation Energies Control the Macroscopic Properties of Physically Cross-Linked Materials. Angew. Chem. Int. Ed. 2014, 53, 10038-10043.
46. Rana, V. K.; Tabet, A.; Vigil, J. A.; Balzer, C. J.; Narkevicius, A.; Finlay, J.; Hallou, C.; Rowitch, D. H.; Bulstrode, H.; Scherman, O. A. Cucurbit[8]uril-Derived Graphene Hydrogels. ACS Macro Lett. 2019, 8, 1629-1634.
47. Li, C.; Rowland, M. J.; Shao, Y.; Cao, T.; Chen, C.; Jia, H.; Zhou, X.; Yang, Z.; Scherman, O. A.; Liu, D. Responsive Double Network Hydrogels of Interpenetrating DNA and CB[8] Host-Guest Supramolecular Systems. Adv. Mater. 2015, 27, 3298-3304.
48. Rodell, C. B.; Dusaj, N. N.; Highley, C. B.; Burdick, J. A. Injectable and cytocompatible tough double-network hydrogels through tandem supramolecular and covalent crosslinking. Adv. Mater. 2016, 28, 8419-8424.
49. Tabet, A.; Mommer, S.; Vigil, J. A.; Hallou, C.; Bulstrode, H.; Scherman, O. A. Mechanical Characterization of Human Brain Tissue and Soft Dynamic Gels Exhibiting Electromechanical Neuro-Mimicry. Adv. Healthc. Mater. 2019, 8, 1900068.

While the present invention has been described with reference to the specific embodiments thereof, it should be understood by those skilled in the art that various changes may be made, and equivalents may be substituted without departing from the true spirit and scope of the invention.

What is claimed is:

1. A flowable biomaterial that forms a defined gel matrix on an ocular tissue area in situ, comprising a polymer that is crosslinked via non-covalent linkages that are reversible under shear in a supramolecular structure, wherein reactive groups of the first polymer are a Cucurbit[n]uril (CB[n], n=5-8 and 10) moiety and reactive groups of the second polymer are an adamantane (Ad) moiety; and further comprising cells encapsulated within the defined gel matrix.

2. The flowable biomaterial of claim 1, wherein the flowable biomaterial is provided as a single, self-healing solution, where the single solution can be injected into or onto a tissue site without the need for mixing.

3. The flowable biomaterial of claim 1, wherein the flowable biomaterial is provided as two solutions combined immediately prior to administration, or at the site of administration, wherein the supramolecular complex is formed.

4. The flowable material of claim 1, wherein the biopolymer is a protein selected from collagen, gelatin, elastin, or a combination thereof.

5. The flowable material of claim 1, wherein the biopolymer is a polysaccharide selected from hyaluronic acid, chondroitin sulfate, keratan sulfate, heparan sulfate, dermatan sulfate or related sulfonated glycosaminoglycans, alginate, cellulose, chitosan, dextran, derivatives and/or a combination thereof.

6. The flowable material of claim 1, where the biopolymer is polyethylene glycol (PEG), multi-arm PEG, poloxamers, or a combination thereof.

7. The flowable biomaterial of claim 1, further comprising cells encapsulated within the defined gel structure.

8. The flowable biomaterial of claim 7, wherein the cells are corneal mesenchymal stromal cells, functional keratocyte precursors, functional keratocytes, functional limbal epithelial cells, functional endothelial cells of the cornea, or stem cells.

9. The flowable biomaterial of claim 1, wherein the first and second solutions are combined in ratios of 1:1, 1:2, 2:1, 1:3, 3:1, 1:4, 4:1, 1:5, 5:1, 1:6, 6:1, 1:7, 7:1, 1:8, 8:1, 1:9, 9:1, 1:10, or 10:1.

10. A hydrogel formed from a flowable material of claim 1.

11. A flowable biomaterial that forms a defined gel matrix on an ocular tissue area in situ, comprising a polymer comprising:

cucurbit[8]uril (CB[8])-based crosslinks formed via thiol-ene reactions between preassembled CB[8]·peptide ternary complexes and norbornenes grafted to a biopolymer, wherein the crosslinks are reversible under shear; and further comprising cells encapsulated within the defined gel matrix.

12. The flowable material of claim 11, wherein the cucurbit[8]uril (CB[8])-based crosslinks are dynamic by virtue of the reversibility of the CB[8]·peptide ternary complexes.

13. The flowable material of claim 11, wherein light-initiated thiol-ene reactions between preassembled CB[8] peptide ternary complexes and grafted norbornenes are used to crosslink the cell-adhesive biopolymer into a supramolecular hydrogel.

14. A flowable biomaterial that forms a defined gel matrix on an ocular tissue area in situ, comprising:

cucurbit[8]uril (CB[8])-based crosslinks formed via thiol-ene reactions between preassembled CB[8]·peptide ternary complexes wherein the peptide comprises an N-terminal phenylalanine and a C-terminal cysteine, and norbornenes grafted to a biopolymer, wherein the crosslinks are reversible under shear;

wherein light-initiated thiol-ene reactions between preassembled CB [8] peptide ternary complexes and grafted norbornenes are used to crosslink the cell-adhesive biopolymer into a supramolecular hydrogel; and further comprising cells encapsulated within the defined gel matrix.

15. The flowable material of claim 14, wherein the peptide is PheGlyGlyCys.

* * * * *